(12) United States Patent
Chang et al.

(10) Patent No.: US 9,422,321 B2
(45) Date of Patent: Aug. 23, 2016

(54) PYRIMIDINE NUCLEOSIDE DERIVATIVES, SYNTHESIS METHODS AND USES THEREOF FOR PREPARING ANTI-TUMOR AND ANTI-VIRUS MEDICAMENTS

(75) Inventors: Junbiao Chang, Zhengzhou (CN); Haoyun An, Zhengzhou (CN); Xuejun Yu, Zhengzhou (CN); Xiaohe Guo, Zhengzhou (CN)

(73) Assignees: High & New Technology Research Center, Henan Academy of Sciences, Zhengzhou (CN); Zhengzhou Granlen Pharmatech Ltd., Zhengzhou (CN); Zhengzhou University, Zhengzhou (CN)

( * ) Notice: Subject to any disclaimer, the term of this patent is extended or adjusted under 35 U.S.C. 154(b) by 321 days.

(21) Appl. No.: 13/820,993

(22) PCT Filed: Sep. 2, 2011

(86) PCT No.: PCT/CN2011/079301
§ 371 (c)(1),
(2), (4) Date: May 15, 2013

(87) PCT Pub. No.: WO2012/031539
PCT Pub. Date: Mar. 15, 2012

(65) Prior Publication Data
US 2013/0303747 A1    Nov. 14, 2013

(30) Foreign Application Priority Data

Sep. 7, 2010  (CN) .......................... 2010 1 0274448
Aug. 25, 2011 (CN) .......................... 2011 1 0245782

(51) Int. Cl.
*C07H 19/00*  (2006.01)
*C07H 19/06*  (2006.01)
*C07H 19/14*  (2006.01)

(52) U.S. Cl.
CPC ............... *C07H 19/06* (2013.01); *C07H 19/14* (2013.01)

(58) Field of Classification Search
CPC ................................. C07H 19/14; C07H 19/06
See application file for complete search history.

(56) References Cited

U.S. PATENT DOCUMENTS 8,765,710 B2 *  7/2014  Sofia et al. ..................... 514/45
8,772,474 B2 *  7/2014  Beigelman et al. ......... 536/26.11
8,835,615 B2 *  9/2014  Chang ........................... 536/22.1

(Continued)

FOREIGN PATENT DOCUMENTS

CN    100532388 C    5/2008
CN    101177442 A    5/2008

(Continued)

OTHER PUBLICATIONS

Alexandrova, L.A. et al. (2007). "Furano- and Pyrrolo [2,3-D] Pyrimidine Nucleosides and Their 5'-O-Triphospates: Synthesis and Enzymatic Activity," *Nucleosides, Nucleotides and Nucleic Acids* 26(8-9):1083-1086.

(Continued)

*Primary Examiner* — Lawrence E Crane
(74) *Attorney, Agent, or Firm* — Morrison & Foerster LLP

(57) ABSTRACT

The present invention relates to the field of pharmacochemistry. Disclosed are fluorinated and azido-substituted pyrimidine nucleoside derivatives, particularly compounds of the formula shown below:

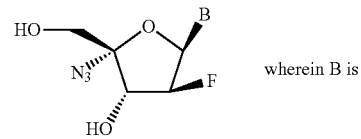

wherein B is

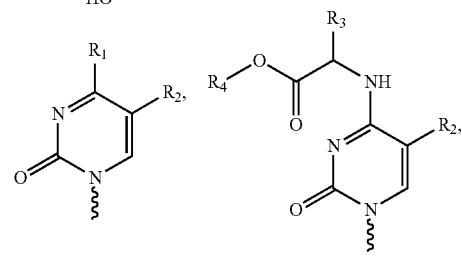

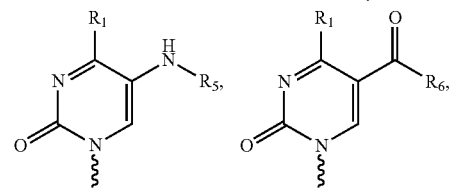

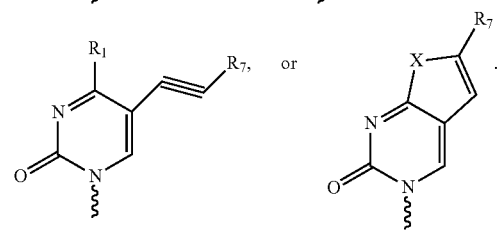

Also disclosed are methods of preparation and uses for these compounds. The compounds can be used for preparing medicaments for treating diseases such as tumors and viral infections, and can be used separately or in combination with other medicaments. The compounds also have effective activity against diseases such as tumors and viral infections, while having few side effects, and thus have potential application value.

20 Claims, No Drawings

(56) References Cited

U.S. PATENT DOCUMENTS 8,877,731 B2 * 11/2014 Beigelman et al. ............. 514/45
2010/0234584 A1   9/2010 Chang

FOREIGN PATENT DOCUMENTS

CN           102000103 A   4/2011
WO    WO-2009/067409 A1   5/2009

OTHER PUBLICATIONS

Ding, Y. et al. (Nov./Dec. 2003). "Synthesis of New 3'-, 5-, and N(4)-Modified 2'-O-Methylcytidine Libraries on Solid Support," *J. Combinatorial Chem.* 5(6):851-859.

International Search Report mailed on Dec. 8, 2011, for PCT Patent Application No. PCT/CN2011/079301, filed on Sep. 2, 2011, 3 pages.

World Health Organization (2009). "World Health Statistics 2009," 149 pages.

Written Opinion of the International Searching Authority mailed on Dec. 8, 2011, for PCT Patent Application No. PCT/CN2011/079301, filed on Sep. 2, 2011, 8 pages.

Extended European Search Report mailed on Dec. 20, 2013, for EP Application No. 11 823 062.2, filed on Sep. 2, 2011, five pages.

Jin, Y.H. et al. (1995). "Synthesis and Antiviral Activity of Fluoro Sugar Nucleosides 1: Studies on 4'-Azido-2'-Deoxy-2'-Fluoro-Arabinofura-Nosyl Nucleosides," *Arch. Pharm. Res.* 18(5):364-365.

Smith, D.B. et al. (May 14, 2009) "The Design, Synthesis, and Antiviral Activity of Monofluoro and Difluoro Analogues of 4'-Azidocytidine Against Hepatitis C Virus Replication: The Discovery of 4'-Azido-2'-Deoxy-2'-Fluorocytidine and 4'-Azido-2'-Dideoxy-2',2'-Difluorocytidine," *J. Med. Chem.* 52(9):2971-2978.

* cited by examiner

PYRIMIDINE NUCLEOSIDE DERIVATIVES, SYNTHESIS METHODS AND USES THEREOF FOR PREPARING ANTI-TUMOR AND ANTI-VIRUS MEDICAMENTS

CROSS-REFERENCE TO RELATED APPLICATIONS

This application is a filing under 35 U.S.C. §371 of International Patent Application No. PCT/CN2011/079301 having an International Filing Date of Sep. 2, 2011, which claims priority benefit of Chinese Application No. CN201010274448.4, filed Sep. 7, 2010, now abandoned, and Chinese Application No. CN201110245782.1, filed Aug. 25, 2011, now issued (CN102351931B, published on Jan. 22, 2014); both of which are hereby incorporated by reference herein, in their entirety.

TECHNICAL FIELD

The present invention relates to pyrimidine nucleoside derivatives, and preparation methods and uses thereof. In particular, the present invention relates to 4'-azido-2'-deoxy-2'-β-fluoropyrimidine nucleoside derivatives, preparation methods thereof, and uses thereof for preparing anti-tumor and anti-virus medicaments.

BACKGROUND ART

Cancer as one of the major diseases is still the most common and is seriously threatening the health of human beings, becoming the second biggest health killer. Current means for treating cancers include methods such as surgical removal, radiotherapy, chemotherapy, immunotherapy, interventional therapy, iontophoresis and the like, or combinations thereof. Among all the methods, chemotherapy is the most widely used and has been used for various types of cancers especially those which cannot be treated with other methods. Although many compounds with chemotherapeutic effects have been used clinically, most chemotherapeutic methods are only to delay the deterioration of the cancer instead of a real cure because of the lack of a sufficiently outstanding efficacy and the narrow therapeutic ranges. Tumors and metastasis thereof which have developed resistance to certain drugs usually cannot be treated with chemotherapy, and some tumors are intrinsically resistant to certain types of chemotherapeutic drugs. The resistance of tumors against a chemotherapeutic drug is gradually developed during the treatment. Therefore, the effects of current chemotherapeutic drugs in treating different kinds of tumors are seriously limited. Furthermore, many chemotherapeutic drugs in different categories for cancer treatment generate very serious side effects so that the chemotherapy can hardly proceed. Thus, it is still urgently desired to find new anti-cancer drugs with better efficacy and fewer side effects in order to safeguard the health of human beings.

A variety of viruses such as hepatitis B virus, hepatitis C virus and human immunodeficiency virus and so on have brought severe damage to the human society. At the time of the outbreak of bird flu, there was almost no medicament for it. Among the 6 billion people in the entire world, half of them live the high prevalence areas of hepatitis B virus (HBV), about 2 billion have been confirmed being infected by HBV, 0.3-0.4 billion have chronic HBV infection, and 15%-25% of them eventually will die from liver cirrhosis and liver cancer. In the worldwide top 10 causes of death related to a disease, hepatitis B is No. 7, causing around 1 million deaths annually and making it an important disease threatening the health of human beings. There are many challenges present in the development of a HBV medicament, such as drug resistance, undetermined drug target and drug resistance development et al. Therefore, researches to develop new anti-HBV drugs with high efficacy and low toxicity are still desired.

Hepatitis C is becoming a global epidemic and is the foremost cause of end-stage liver disease in western countries and Japan. According to a statistics coming from WHO in 2009, there were around 180 million people globally having hepatitis C and there were around 35 thousand emerging hepatitis C cases annually. The global death caused by live diseases associated with hepatitis C almost doubles every 10 years. The current death rate of hepatitis C is ranked the tenth among all the diseases worldwide and there is no vaccine for it yet. A commonly recognized routine treatment for chronic hepatitis C uses ribavirin developed by an American, Valeant, and PEGylated interferon in combination. The sustained virological response (SVR) of HCV is only 47%-54%. And there are some patients who may be forced to stop taking the mediation because of severe side effects, and for many patients there is even no effective medicament available for them. Consequently, it is extremely urgent to develop new anti-HCV drugs with high efficacy and low toxicity.

Human immunodeficiency virus (HIV) is a major disease that is seriously threatening human health. Although several nucleoside based medicaments have been used to alleviate the suffering of people with AIDS, most of them has low efficacy and severe toxic side effects, and induces drug resistance very easily. Therefore, researches on new nucleoside-based anti-AIDS medicament are still recognized as an important field for humans to defeat serious diseases.

The monomeric nucleoside from natural products, deoxy nucleic acid (DNA) and ribose nucleic acid (RNA), can be modified to produce natural product medicament which would have lower toxic side effect. Although over 70 nucleoside-based medicaments have been widely used so far in the treatment for diseases such as cancer and viral disease, there remain unmet medical needs and better nucleoside-based drugs are still needed to be developed. The most desirable medicament should be against virus and tumor at the same time and would make an important contribution to human's well-being.

THE CONTENT OF THE INVENTION

An object of the invention is to provide a class of 4'-azido-2'-deoxy-2'-β-fluoropyrimidine nucleoside derivatives having anti-tumor, anti-cancer, anti-virus, anti-infection and anti-proliferation activities. Another object is to provide the preparation method making the same. Yet another object is to provide uses thereof for preparing anti-virus and anti-tumor medicaments.

In order to achieve the purpose of the present invention, 4-position and 5-position substituted 4'-azido-2'-deoxy-2'-β-fluororibonucleoside derivatives and 4'-azido-2'-deoxy-2'-β-fluororibonucleoside derivatives with 4,5-cyclization, and epimers thereof, including pharmaceutical acceptable salts and derivatives thereof are synthesized in the invention by structurally modifying ribonucleoside. They have the following general structural formulae and include pharmaceutical acceptable salts, esters, prodrugs or metabolites thereof.

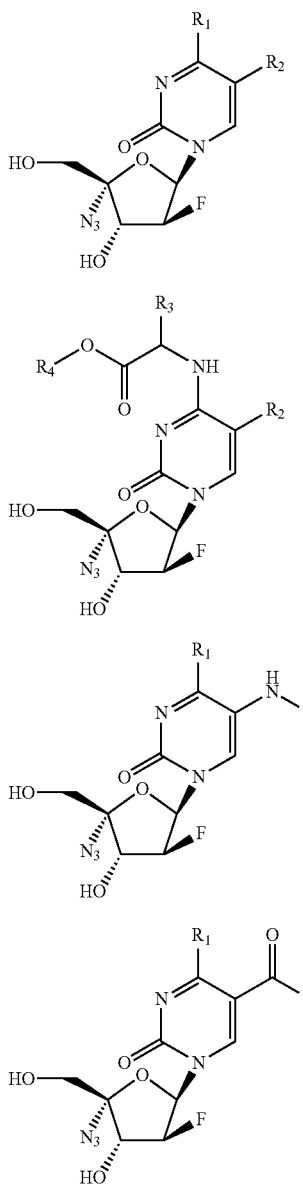

(1)

(2)

(3)

(4)

Wherein $R_1$ is selected from OH, NHOH, NHOCH$_3$, NHOEt, NHOR, NROH, NROR, NHR, NRR, NH(CH$_2$)$_n$OH, NH(CH$_2$)$_n$OR, NH(CH$_2$)$_n$SR, N[(CH$_2$)$_n$OH]$_2$, NHCH$_2$Ar, NHCH$_2$-Het, CN, COOH, CONH$_2$, COOR, CSNH$_2$, C(=NH)NH$_2$, C(=NH)OR, C(=NH)OH, NHNH$_2$, NHNHR, NRNH$_2$, NRNHR, NRNRR, NHNHC(=O)NH$_2$, NHNHC(=S)NH$_2$, NHNHC(=O)NHR, NHNHC(=S)NR, NHC(=O)NHR, NHC(=S)NHR, NHCH$_2$CONH$_2$, NHCH$_2$CONHR; alternatively, the two R groups on —NRR, NRNHR, NRNRR may join together to form a 3- to 10-membered cyclic group in which the heteroatoms are N and O or S; wherein, n=2-8; R is C$_1$-C$_8$ alkyl, C$_2$-C$_8$ alkenyl, C$_2$-C$_8$ alkalkenyl, C$_2$-C$_8$ alkenylalkyl, C$_2$-C$_8$ alkynyl, C$_2$-C$_8$ alkalkynyl, C$_2$-C$_8$ alkynylalkyl, C$_3$-C$_8$ cycloalkyl, C$_3$-C$_8$ cycloalkenyl, amino acid, substituted amino acid, C$_1$-C$_8$ hydroxyalkyl, C$_2$-C$_8$ sulfanylalkyl, C$_1$-C$_8$ cyanoalkyl, C$_1$-C$_8$ aminoalkyl, C$_1$-C$_8$ carboxyalkyl, methoxy, methylsulfanyl, C$_2$-C$_8$ alkoxy, C$_2$-C$_8$ alkylsulfanyl, C$_6$-C$_{12}$ aralkyl, C$_3$-C$_6$ heterocycloalkyl; or, R is H, F, Cl, Br, I, CF$_3$, OCF$_3$, O—C$_6$-C$_{12}$ aryl or a O—C$_3$-C$_6$ heterocyclic group; wherein Ar is conjugated C$_5$-C$_{10}$ monocyclic or bicyclic aryl; Het is conjugated C$_5$-C$_{10}$ monocyclic or bicyclic aryl containing 1-3 heteroatoms selected from N, O or S;

$R_2$ is selected from H, OH, NH$_2$, methyl, ethyl, C$_3$-C$_{10}$ alkyl, methoxy, methylsulfanyl, C$_2$-C$_{10}$ alkoxy, C$_2$-C$_{10}$ alkylsulfanyl, CH$_2$NH$_2$, CH$_2$OH or CH$_2$OR; or, a conjugated C$_5$-C$_{10}$ aromatic cyclic group with or without a R substituent mentioned above on the ring thereof, or a C$_3$-C$_6$ heterocycloalkyl group with or without a R substituent mentioned above on the ring thereof;

$R_3$ is selected from H, CH$_3$, CH$_2$CH$_3$, CH$_2$CH$_2$CH$_3$, CHMe$_2$, CH$_2$SH, CH$_2$CH$_2$SH, CH$_2$OH, CH$_2$C$_6$H$_5$, CH$_2$CONH$_2$, CH$_2$COOH, CH$_2$COOR, CH$_2$CH$_2$CONH$_2$, CH$_2$CH$_2$COOH, CH$_2$CH$_2$COOR, CH$_2$CH$_2$CH$_2$NHC(=NH)NH$_2$, CHMeCH$_2$CH$_3$, CH$_2$CHMe$_2$, CH$_2$CH$_2$CH$_2$CH$_2$NH$_2$, CH$_2$CH$_2$SCH$_3$, CH(OH)CH$_3$, CH$_2$C$_6$H$_4$OH-p, CH$_2$-imidazole, CH$_2$-indole; C$_{6-10}$ alkyl, C$_{2-10}$ hydroxyalkyl, C$_{4-10}$ sulfanylalkyl, Ar, CH$_2$Ar or CH$_2$-Het, wherein there may or may not be a R substituent mentioned above on the ring of said Ar and Het groups and Ar, Het and R groups have the same meanings as defined above;

$R_4$ is H, methyl, ethyl, C$_3$-C$_{10}$ alkyl, C$_6$-C$_{12}$ aralkyl or C$_3$-C$_6$ heterocycloalkyl;

$R_5$ is C$_1$-C$_{10}$ alkyl, C$_2$-C$_{10}$ alkenyl, C$_2$-C$_{10}$ alkalkenyl, C$_2$-C$_{10}$ alkenylalkyl, C$_2$-C$_{10}$ alkynyl, C$_2$-C$_{10}$ alkalkynyl, C$_2$-C$_{10}$ alkynylalkyl, C$_1$-C$_{10}$ cyanoalkyl, C$_1$-C$_{10}$ aminoalkyl or C$_1$-C$_{10}$ carboxyalkyl; (CH$_2$)$_n$OH, (CH$_2$)$_n$OR, (CH$_2$)$_n$SR, CH$_2$Ar, CH$_2$CH$_2$Ar, CH$_2$-Het or CH$_2$CH$_2$-Het, wherein there may or may not be a R substituent mentioned above on the ring of said Ar and Het groups and Ar, Het and R groups have the same meanings as defined above and wherein n=2-8;

$R_6$ is NHR, NRR, NH(CH$_2$)$_n$OH, NH(CH$_2$)$_n$OR, NH(CH$_2$)$_n$SR, N[(CH$_2$)$_n$OH]$_2$, NHCH$_2$Ar, NHAr, N(CH$_2$Ar)$_2$, NAr$_2$, NHCH$_2$-Het; cyclic amino groups having 3-8 carbon atoms with or without 1-2 carbon atoms in the ring thereof being substituted with O, S, NH, NR, Po or P(O)(OH)$_2$; wherein, R is C$_1$-C$_{15}$ alkyl, C$_2$-C$_{15}$ alkenyl, C$_2$-C$_{15}$ alkalkenyl, C$_2$-C$_{15}$ alkenylalkyl, C$_2$-C$_{15}$ alkynyl, C$_2$-C$_{15}$ alkalkynyl, C$_2$-C$_{15}$ alkynylalkyl, C$_3$-C$_{15}$ cycloalkyl, C$_3$-C$_{15}$ cycloalkenyl, C$_6$-C$_{12}$ aralkyl, C$_3$-C$_6$ heterocycloalkyl, hydroxyalkyl, sulfanylalkyl, cyanoalkyl, aminoalkyl or carboxyalkyl; wherein Ar, Het and R groups have the same meanings as defined above;

In addition, compounds with the following structural formulae (5) and (6) are synthesized and the pharmaceutically acceptable salts, esters, prodrugs or metabolites thereof are also included in the invention.

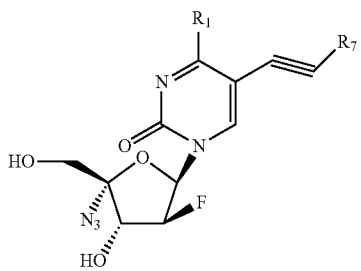

(5)

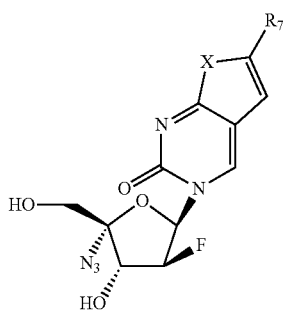

(6)

wherein R$_1$ is as defined above.

R$_7$ is C$_1$-C$_{18}$ alkyl, hydroxymethyl, hydroxyethyl, hydroxypropyl or C$_4$-C$_{10}$ hydroxyalkyl; CH$_2$OR, CH$_2$SR, Ar, Het, (CH$_2$)$_{1-12}$—Ar, (CH$_2$)$_{1-12}$-Het, or a C$_1$-C$_{18}$ alkyl group with 1-3 double bonds or triple bonds or 1-3 O or S atoms in the alkyl chain; wherein Ar and Het groups are as defined above.

X=NH, O, S, NR.

Among the substituents in the general formulae (1)-(6), some typical aryl (Ar) groups, heterocyclic groups (Het) and R$_5$, R$_7$ are preferably piperazinyl, piperidinyl, morpholinyl, thiomorpholinyl, phenyl, naphthyl, furyl, thienyl, pyrazolyl, pyrrolyl, imidazolyl, thiazolyl, oxazolyl, isoxazolyl, isothiazolyl, [1,2,4]oxadiazolyl, triazolyl, thiadiazolyl, pyridyl, pyridazinyl, pyrimidinyl, pyrazinyl, triazinyl, indolizinyl, indolyl, isoindolyl, isoquinolyl, quinazolinyl, benzofuryl, benzothienyl, indazolyl, benzoimidazolyl, benzothiazolyl, purinyl, quinolyl, isoquinolyl, cinnolinyl, phthalazinyl, quinolizinyl, quinoxalinyl, pyrazopyrimidinyl, naphthyridinyl, pteridinyl, phenazinyl, phenothiazinyl, benzoxadiazolyl, benzo[1,2,4]oxadiazolyl, and the like; wherein each group can be separately and independently substituted with one or more heteroatoms selected from O, N, S and halogens, or can be substituted with C$_{1-10}$ alkyl, C$_{3-10}$ cycloalkyl, C$_{2-10}$ alkenyl or alkynyl, aryl or heterocyclic groups, and such groups can each contain a heteroatom.

The invention comprises a formulation and the preparation method thereof, wherein said formulation uses a nucleoside compound encompassed in the above formulae (1)-(6) as the active ingredient. The preparation method of the formulation comprises: dissolving a compound encompassed in the present invention into a solvent such as water-soluble organic solvent, non-ionic surfactants, water-soluble lipids, various cyclodextrins, fatty acids, esters of fatty acid, phospholipids or the combination thereof to give a formulation solution; adding to the formulation solution physiological saline or 1-20% carbohydrate. The organic solvent includes polyethylene glycol (PEG), ethanol, propylene glycol or the combination thereof.

The term "alkyl" used herein refers to various saturated hydrocarbyl groups which are straight, branched or cyclic, and small alkyl groups with 10 or less carbon atoms are preferred. A few typical examples included in the definition are methyl, ethyl, propyl, isopropyl, butyl, sec-butyl, pentyl, hexyl etc. The term "alkenyl" used herein have a same definition as that above for "alkyl" except that at least one carbon-carbon double bond (C=C) must be included in the chain. Accordingly, the alkenyl used in the invention contains straight, branched or cyclic hydrocarbyl groups having two to ten carbon atoms and at least one carbon-carbon double bond, such as vinyl, acryl, butenyl and the like. Similarly, the "alkynyl" used in the invention is an alkyl or an alkynyl described above with at least one carbon-carbon triple bond. Thus, the alkynyl contains straight, branched or cyclic hydrocarbyl or alkynyl groups having two to ten carbon atoms and at least one carbon-carbon triple bond, such as ethynyl, propynyl, butynyl, pentynyl and the like. The carbon-carbon double bond or triple bond in the "alkenylalkyl" or "alkynylalkyl" described herein is on the distal end of the substituent and far away from the conjunction site between the substituent and the major structure of the molecule. Whereas in "alkalkenyl" or "alkalkynyl", the carbon-carbon double bond or triple bond is directly connected to the major structure of the molecule.

The "cycloalkyl" used herein is a cyclic hydrocarbyl group preferably having three to eight carbon atoms. Accordingly, cyclopropane, cyclobutane, cyclopentane, cyclohexane and cycloheptane are all typical examples included in the definition. If one or two carbon-carbon double bonds are contained in the ring, a cycloalkyl group becomes a "cycloalkenyl". There may also be alkyl, alkenyl, alkynyl or halogen atoms on a cycloalkyl group.

The "aryl" described herein is a conjugated aromatic ring system which may also have one or more non-carbon atoms (i.e., heteroatoms other than carbon, such as nitrogen, sulfur, phosphorus etc.) in the ring, for example, phenyl, naphthyl, pyridyl and the like. These aryl groups can further form "fused aryl groups" through two covalent bonds fused with other five- or six-membered aryl groups or heterocyclic groups.

The "heterocyclic group" or "heterocycloalkyl group" described herein refers to any conjugated or non-conjugated cyclic groups with at least one non-carbon atom which are formed through covalent bonding of multiple atoms. The heterocyclic group is preferably a five- or six-membered cyclic system containing a non-carbon atom like N, S or O, for example, imidazole, pyrrole, indole, pyridine, thiazole and the like. These heterocyclic groups can further be fused with a monocyclic, dicyclic or heterocyclic structure to form "fused heterocyclic groups".

The "alkoxy" described herein refers to alkyl oxides or alkyl-oxy groups formed by connecting an oxygen atom to a straight or branched alkyl hydrocarbyl group. The hydrocarbon portion of this group may contain any number of carbon atoms and may include one or two O, S or N atoms as well as double bond or triple bond. Examples of such alkoxy groups include methoxy, ethoxy, propoxy, isopropoxy, methoxyethoxy and the like. Similarly, the "alkylsulfanyl" refers to alkyl sulfides or alkyl-sulfanyl groups formed by connecting a sulfur atom to a straight or branched alkyl group. The hydrocarbon portion of this group may contain any number of carbon atoms and may include one or two O, S or N atoms as well as double bond or triple bond. Examples of such alkylsulfanyl groups include methylsulfanyl, ethylsulfanyl, propylsulfanyl, isopropylsulfanyl, methoxyethylsulfanyl and the like.

The "alkylamino" refers to straight or branched alkane-amino groups, wherein the amino nitrogen can contain one or two alkyl groups which may contain double bond or triple bond. The hydrocarbon portion of this group may contain any number of carbon atoms and may include one or two O, S or N atoms as well as double bond or triple bond. Examples of such alkylamino groups include methylamino, dimethylamino, ethylamino, diethylamino, and the like. While for an "aminoalkyl", the amino group is on the distal end of the alkyl group, for example, aminoethyl is H$_2$NCH$_2$CH$_2$—.

The "amino acid" in the invention refers to substituted natural or non-natural amino acids in a pure L- or D-configuration or in the form of a racemic mixture, and other groups derived from the amino group and the carboxyl group thereof.

It is worth further mentioning that the various substituents defined above also include the groups formed after they are further substituted, wherein the new substituents may as well comprise other groups. For example, new substituents belonging to the groups in each definition above can be formed by substituting the hydrogen atom in an alkyl group or aryl group with an amino group, a halogen or other groups.

Compounds encompassed by the formulae (1)-(6) in the invention and salts and prodrugs thereof can be used for the preparation of medicaments or medicament formulations for the treatment, prevention or alleviation of cancers or viral diseases, especially suitable for the treatment or alleviation of cancers caused by tumor cells in a human tissue or organ. The cancer is preferably colon cancer, liver cancer, lymphoma, lung cancer, esophageal cancer, breast cancer, central nervous system tumor, melanoma, ovarian cancer, cervical cancer, kidney cancer, leukemia, prostate cancer, pancreatic cancer, gastric cancer and the like. Compounds in formulae (1)-(6) in the invention can further be used for the treatment or prevention or alleviation of diseases caused by virus such as hepatitis B virus, hepatitis C virus, HIV, yellow fever virus (YFV), respiratory syncytial virus (RSV), herpes simplex virus (HSV), bovine viral diarrhea virus (BVDV), hepatitis G virus (HGV), GB virus-B (GBV-B), dengue virus (Dengue), human rhinovirus (HRV), polio virus (Poliovirus), varicella-zoster virus (VZV), Epstein-Barr virus (EBV), cytomegalovirus (CMV), and the like.

A salt form of the compounds in formulae (1)-(6) described herein can be formed through a reaction between the positively charged group (e.g. amino group) in the molecule and a pharmaceutically proper negative ion. The proper negative ion includes but not limited to fluoride, chloride, bromide, iodide, sulfate, nitrate, phosphate, tartrate, methanesulfonate, trifluoroacetate, maleate, acetate, and the like. A pharmaceutically acceptable salt can also be formed through a reaction between the negatively charged group (carboxyl group) in the molecule and a positive ion. The positively charged ions useful for the purpose of the invention are, for example, sodium, potassium, magnesium and calcium ions, and organic ammonium ions such as tetramethyl ammonium ion, tetrabutyl ammonium ion and other organic ions.

The innovative points and advantages of the invention are as follows: multiple series of novel 4'-azido-2'-deoxy-2'-β-fluoropyrimidine nucleoside derivatives with anti-tumor, anti-cancer, anti-virus, anti-infection and anti-proliferation activities are inventively synthesized by modifying the pyrimidine base in a nucleoside; the preparation method thereof is feasible; and the application thereof in medicaments for the treatment of viral disease and cancer is promising.

DETAILED DESCRIPTION OF THE INVENTION

The invention is further illustrated through the following specific examples.

EXAMPLES

Example 1

The key intermediate compound 3 of the pyrimidine nucleoside derivatives encompassed in the invention can be synthesized according the following procedure: the synthesis of the key intermediate 2'-deoxy-2'-β-fluoro-4'-azido-3'-O-benzoyl-5'-O-(m-chlorobenzoyl)uridine (3) can be found in the description of CN 100532388C. The present invention has modified the last two steps of the synthesis process to be as follows: adding benzoyl chloride with stirring to compound 1 dissolved in DMF followed by the addition of mCPBA/mCBA separately, reacting in room temperature for 8 h before filtration, removing the solvent under reduced pressure (below 50° C.) and purifying with column chromatography to give compound 3 (71.3%). Reference can be made to Scheme A.

Scheme A. Synthesis of the key intermediate 3

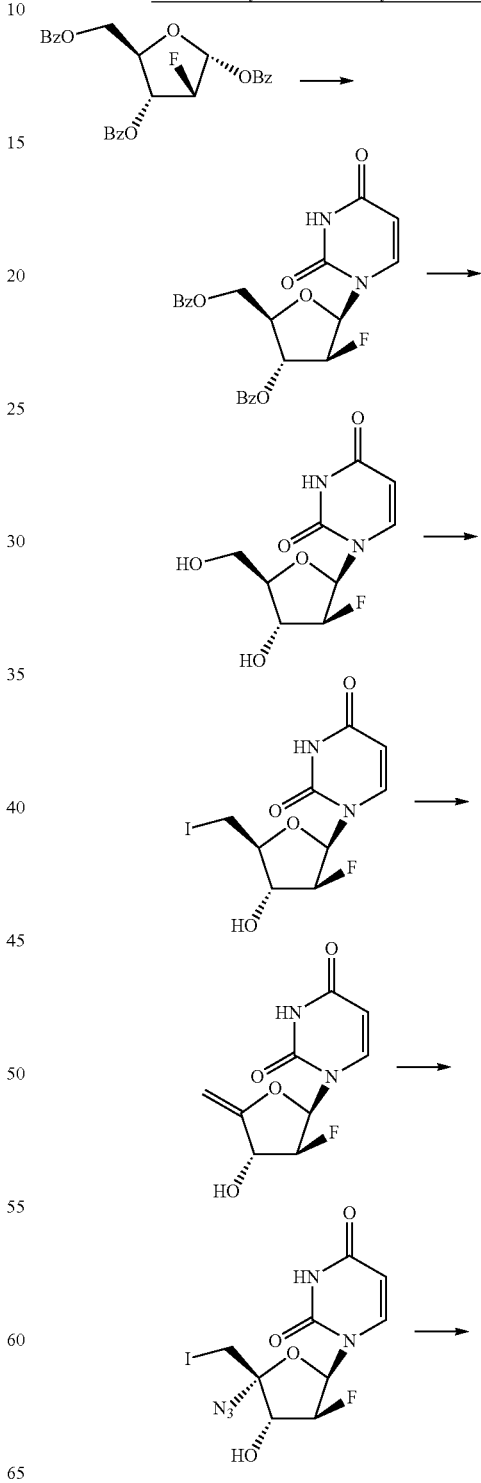

1

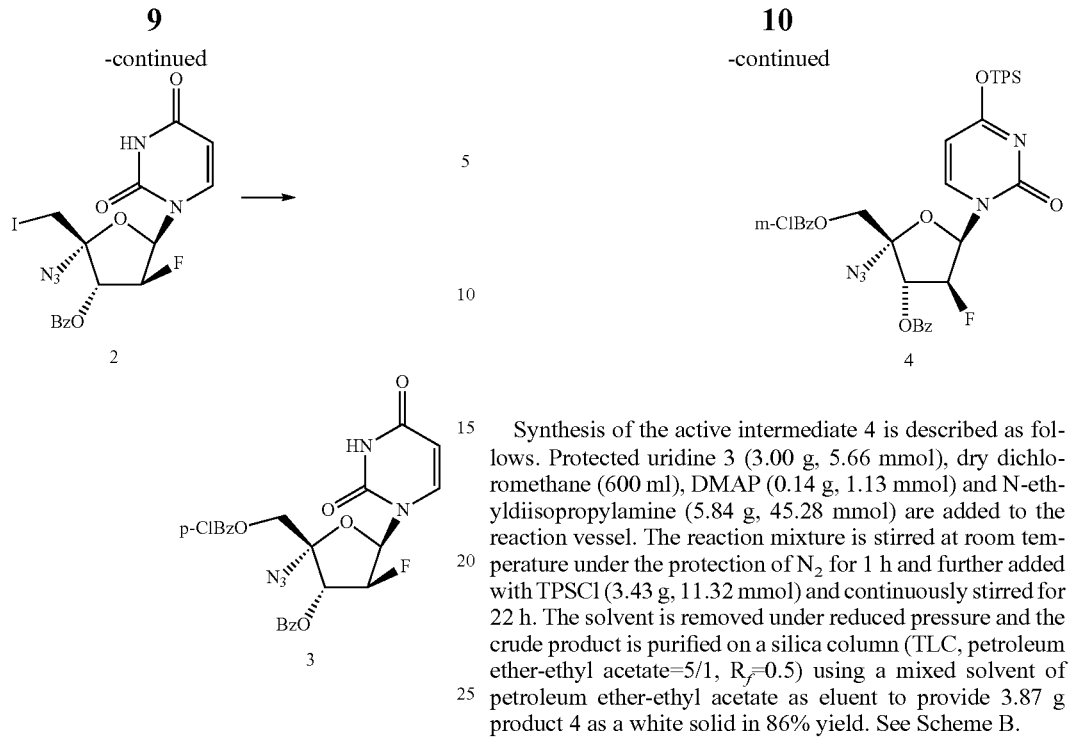

Example 2

The pyrimidine nucleoside derivative of formula 1 described in the invention is synthesized with a method comprising the following steps:

activating position 4 of the key intermediate 3 at first (Ding, Y.; Habib, Q.; Shaw, S. W.; Li, D. Y.; Abt, J. W.; Hong, Z.; An, H. J. Combinatorial Chem. 2003, 5, 851-859);

reacting compound 4 with a building block molecule selected from different kinds of substituted amines, hydroxyamine, hydrazine etc.;

performing a deprotection reaction to produce the desired product.

Synthesis of the active intermediate 4 is described as follows. Protected uridine 3 (3.00 g, 5.66 mmol), dry dichloromethane (600 ml), DMAP (0.14 g, 1.13 mmol) and N-ethyldiisopropylamine (5.84 g, 45.28 mmol) are added to the reaction vessel. The reaction mixture is stirred at room temperature under the protection of $N_2$ for 1 h and further added with TPSCl (3.43 g, 11.32 mmol) and continuously stirred for 22 h. The solvent is removed under reduced pressure and the crude product is purified on a silica column (TLC, petroleum ether-ethyl acetate=5/1, $R_f$=0.5) using a mixed solvent of petroleum ether-ethyl acetate as eluent to provide 3.87 g product 4 as a white solid in 86% yield. See Scheme B.

Example 3

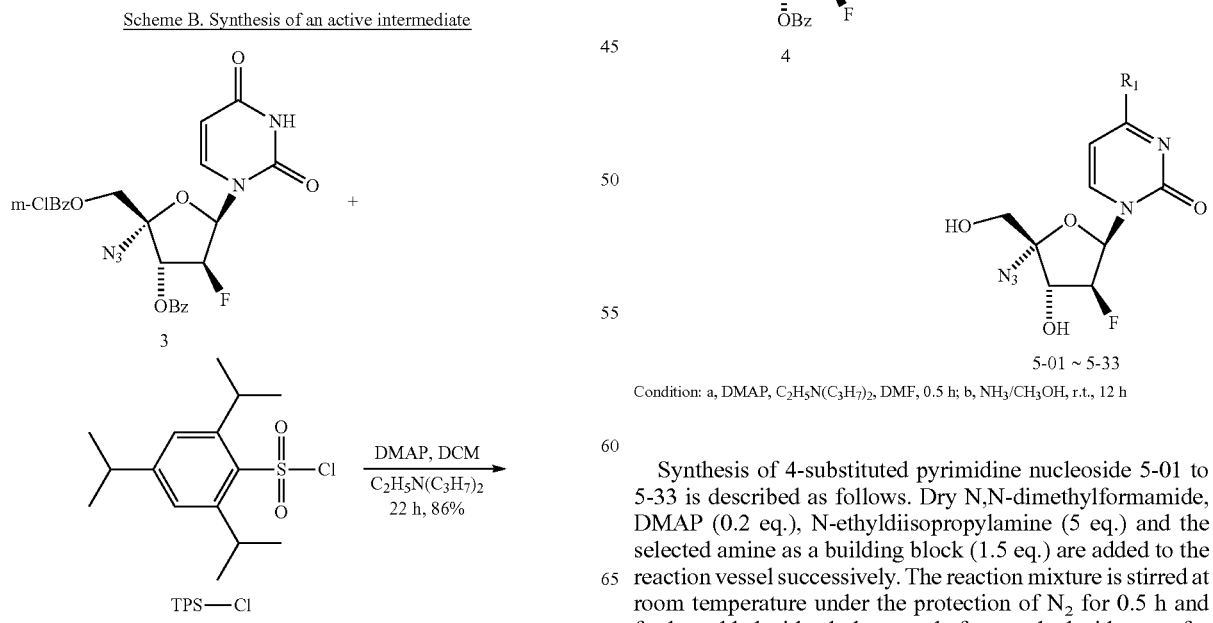

Condition: a, DMAP, $C_2H_5N(C_3H_7)_2$, DMF, 0.5 h; b, $NH_3/CH_3OH$, r.t., 12 h Synthesis of 4-substituted pyrimidine nucleoside 5-01 to 5-33 is described as follows. Dry N,N-dimethylformamide, DMAP (0.2 eq.), N-ethyldiisopropylamine (5 eq.) and the selected amine as a building block (1.5 eq.) are added to the reaction vessel successively. The reaction mixture is stirred at room temperature under the protection of $N_2$ for 0.5 h and further added with ethyl acetate before washed with water for three times and dried over anhydrous sodium sulfate. The solvent is removed under reduced pressure. Then the crude product and the methanol solution saturated with ammonia gas are allowed to react in a sealed reaction vessel at room temperature with stirring for 12 h. The solvent is removed under reduced pressure and the crude product is purified with a preparative silica chromatoplate to produce products 5-01~5-33 as white solids. See Scheme C. Structures of $R_1$ in the products are shown in Table 1.

TABLE 1

| entry | $R_1$ | Yield (%) |
|---|---|---|
| 5-01 | EtNH | 90 |
| 5-02 | NHCH$_2$CH$_2$NH$_2$ | 85 |
| 5-03 | 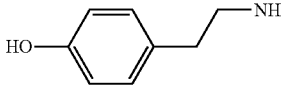 | 91 |
| 5-04 | NEt$_2$ | 80 |
| 5-05 |  | 82 |
| 5-06 | 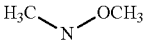 | 76 |
| 5-07 | NHOCH$_3$ | 59 |
| 5-08 | NHOEt | 93 |
| 5-09 | 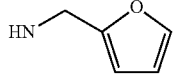 | 92 |
| 5-10 | 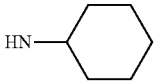 | 94 |
| 5-11 | 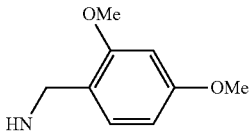 | 71 |
| 5-12 | 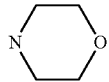 | 71 |
| 5-13 | 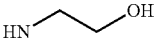 | 88 |
| 5-14 | 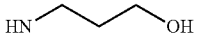 | 84 |
| 5-15 | 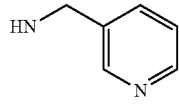 | 75 |
| 5-16 | 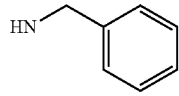 | 85 |
| 5-17 | NHOH | 90 |
| 5-18 | 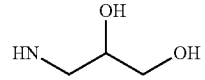 | 78 |
| 5-19 | 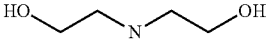 | 91 |
| 5-20 | 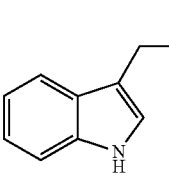 | 40 |
| 5-21 | N(CH$_3$)$_2$ | 68 |
| 5-22 |  | 41 |
| 5-23 | 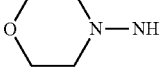 | 75 |
| 5-24 | NH(CH$_2$)$_4$CH$_3$ | 75 |
| 5-25 | NH(CH$_2$)$_5$CH$_3$ | 85 |
| 5-26 | NH(CH$_2$)$_6$CH$_3$ | 90 |
| 5-27 | NH(CH$_2$)$_7$CH$_3$ | 95 |
| 5-28 | NHCH$_3$ | 35 |
| 5-29 | 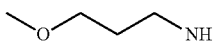 | 87 |
| 5-30 |  | 52 |
| 5-31 | CH$_3$NHNH | 50 |
| 5-32 |  | 85 |
| 5-33 |  | 85 |

Data from the NMR spectra and mass spectra of typical compounds listed in the above table are shown below.

Compound 5-01: $^1$HNMR (300 MHz, DMSO$_{d6}$) δ1.10 (t, 3H, J=6.0 Hz, CH$_3$), 3.25 (m, 2H, CH$_3$CH$_2$), 3.6-3.8 (m, 2H, 5'-CH$_2$), 4.49 (d, 1H, J=24 Hz, 3'-H), 5.24 (d, 1H, J=54 Hz, 2'-H), 5.77 (d, 1H, J=12.0 Hz, 5-H), 6.40 (d, 1H, J=12.0 Hz, 1'-H), 7.51 (d, 1H, J=9.0 Hz, 6-H), 7.92 (t, 1H, J=6.0 Hz, NH).

Compound 5-03: HRMS (ESI) calcd for C$_{17}$H$_{19}$FN$_6$O$_5$Na [M+Na]$^+$429.1299. found 429.1276; calcd for C$_{17}$H$_{20}$FN$_6$O$_5$ [M+H]$^+$407.1479. found 407.1456.

Compound 5-04: $^1$HNMR (300 MHz, DMSO$_{d6}$) δ1.40 (m, 6H, 2×CH$_3$), 3.15 (m, 4H, 2×CH$_3$CH$_2$), 3.65 (m, 2H, 5'-CH$_2$), 4.72 (d, 1H, J=6.0 Hz, 3'-H), 5.21 (d, 1H, J=54 Hz, 2'-H), 5.79 (s, 1H, 3'-OH), 5.92 (d, 1H, J=6.0 Hz, 5-H), 6.28 (s, 1H, 5'-OH), 6.55 (d, 1H, J=9.0 Hz, 1'-H), 7.82 (d, 1H, J=6.0 Hz, 6-H).

Compound 5-05: $^1$HNMR (300 MHz, DMSO$_{d6}$) δ3.55 (m, 4H, 2×CH$_2$), 3.77 (m, 2H, 5'-CH$_2$), 3.95 (m, 4H, 2×CH$_2$), 4.74 (d, 1H, J=21 Hz, 3'-H), 5.30 (d, 1H, J=54 Hz, 2'-H), 5.90 (d, 1H, J=6.0 Hz, 5-H), 6.55 (d, 1H, J=6.0 Hz, 1'-H), 7.97 (d, 1H, J=9.0 Hz, 6-H).

Compound 5-06: HRMS (ESI) calcd for C$_{11}$H$_{15}$FN$_6$O$_5$Na [M+Na]$^+$353.0986. found 353.0981; calcd for C$_{11}$H$_{16}$FN$_6$O$_5$ [M+H]$^+$331.1166. found 331.1166.

Compound 5-07: HRMS (ESI) calcd for $C_{10}H_{13}FN_6O_5Na$ [M+Na]$^+$ 339.0829. found 339.0831.

Compound 5-08: HRMS (ESI) calcd for $C_{11}H_{15}FN_6O_5Na$ [M+Na]$^+$ 353.0986. found 353.0986.

Compound 5-09: HRMS (ESI) calcd for $C_{14}H_{15}FN_6O_5Na$ [M+Na]$^+$ 389.0986. found 389.0995; calcd for $C_{14}H_{16}FN_6O_5$ [M+H]$^+$ 367.1166. found 367.1167.

Compound 5-10: HRMS (ESI) calcd for $C_{15}H_{21}FN_6O_4Na$ [M+Na]$^+$ 391.1506. found 391.1517; calcd for $C_{15}H_{22}FN_6O_4$ [M+H]$^+$ 369.1687. found 369.1695.

Compound 5-11: HRMS (ESI) calcd for $C_{18}H_{21}FN_6O_6Na$ [M+Na]$^+$ 459.1404. found 459.1405; calcd for $C_{18}H_{22}FN_6O_6$ [M+H]$^+$ 437.1585. found 437.1593.

Compound 5-12: HRMS (ESI) calcd for $C_{13}H_{17}FN_6O_5Na$ [M+Na]$^+$ 379.1142. found 379.1123; calcd for $C_{13}H_{18}FN_6O_5$ [M+H]$^+$ 357.1323. found 357.1304.

Compound 5-13: HRMS (ESI) calcd for $C_{11}H_{15}FN_6O_5Na$ [M+Na]$^+$ 353.0986. found 353.0966; calcd for $C_{11}H_{16}FN_6O_5$ [M+H]$^+$ 331.1166. found 331.1149.

Compound 5-14: HRMS (ESI) calcd for $C_{12}H_{17}FN_6O_5Na$ [M+Na]$^+$ 367.1142. found 367.1126; calcd for $C_{12}H_{18}FN_6O_5$ [M+H]$^+$ 345.1323. found 345.1308.

Compound 5-15: HRMS (ESI) calcd for $C_{15}H_{16}FN_7O_4Na$ [M+Na]$^+$ 400.1145. found 400.1129; calcd for $C_{15}H_{17}FN_7O_4$ [M+H]$^+$ 378.1326. found 378.1306.

Compound 5-16: HRMS (ESI) calcd for $C_{16}H_{17}FN_6O_4Na$ [M+Na]$^+$ 399.1193. found 399.1179; calcd for $C_{16}H_{18}FN_6O_4$ [M+Na]$^+$ 377.1374. found 377.1365.

Compound 5-17: $^1$HNMR (300 MHz, DMSO$_{d6}$) δ 3.74 (m, 2H, 5'-CH$_2$), 4.45 (d, 1H, J=24 Hz, 3'-H), 5.28 (d, 1H, J=54 Hz, 2'-H), 5.68 (d, 1H, J=30 Hz, 5-H), 6.34 (m, 1H, 1'-H), 6.85 (d, 1H, J=9.0 Hz, 6-H). HRMS (ESI) calcd for $C_9H_{11}FN_6O_5Na$ [M+Na]$^+$ 325.0673. found 325.0672.

Compound 5-18: HRMS (ESI) calcd for $C_{12}H_{17}FN_6O_6Na$ [M+Na]$^+$ 383.1091. found 383.1068; calcd for $C_{12}H_{18}FN_6O_6$ [M+H]$^+$ 361.1272. found 361.1124.

Compound 5-19: HRMS (ESI) calcd for $C_{13}H_{19}FN_6O_6Na$ [M+Na]$^+$ 397.1248. found 397.1229; calcd for $C_{13}H_{20}FN_6O_6$ [M+H]$^+$ 375.1428. found 375.1408.

Compound 5-20: HRMS (ESI) calcd for $C_{19}H_{20}FN_7O_4Na$ [M+Na]$^+$ 452.1459. found 452.1454; calcd for $C_{19}H_{21}FN_7O_4$ [M+H]$^+$ 430.1639. found 430.1636.

Compound 5-21: HRMS (ESI) calcd for $C_{11}H_{15}FN_6O_4Na$ [M+Na]$^+$ 337.1037. found 337.1036; calcd for $C_{11}H_{16}FN_6O_4$ [M+H]$^+$ 315.1217. found 315.1213.

Compound 5-22: HRMS (ESI) calcd for $C_{13}H_{18}FN_7O_5Na$ [M+Na]$^+$ 394.1251. found 394.1258; calcd for $C_{13}H_{19}FN_7O_5$ [M$^+$+H] 372.1432. found 372.1442.

Compound 5-23: HRMS (ESI) calcd for $C_{13}H_{19}FN_6O_5Na$ [M+Na]$^+$ 381.1299. found 381.1322; calcd for $C_{13}H_{20}FN_6O_5$ [M+H]$^+$ 359.1479. found 359.1500.

Compound 5-24: HRMS (ESI) calcd for $C_{14}H_{21}FN_6O_4Na$ [M+Na]$^+$ 379.1506. found 379.1508; calcd for $C_{14}H_{22}FN_6O_4$ [M+H]$^+$ 357.1687. found 357.1697.

Compound 5-25: HRMS (ESI) calcd for $C_{15}H_{23}FN_6O_4Na$ [M+Na]$^+$ 393.1663. found 393.1658; calcd for $C_{15}H_{24}FN_6O_4$ [M+H]$^+$ 371.1843. found 371.1841.

Compound 5-26: HRMS (ESI) calcd for $C_{16}H_{25}FN_6O_4Na$ [M+Na]$^+$ 407.1819. found 407.1807; calcd for $C_{16}H_{26}FN_6O_4$ [M+H]$^+$ 385.2000. found 385.1990.

Compound 5-27: HRMS (ESI) calcd for $C_{17}H_{27}FN_6O_4Na$ [M+Na]$^+$ 421.1976. found 421.1962; calcd for $C_{17}H_{28}FN_6O_4$ [M+H]$^+$ 399.2156. found 399.2147.

Compound 5-28: HRMS (ESI) calcd for $C_{10}H_{13}FN_6O_4Na$ [M+Na]$^+$ 323.0880. found 323.0878; calcd for $C_{10}H_{14}FN_6O_4$ [M$^+$+H] 301.1061. found 301.1067.

Compound 5-29: $^1$HNMR (300 MHz, DMSO$_{d6}$) δ 2.68 (m, 4H, 2×SCH$_2$), 3.88 (m, 2H, 5'-CH$_2$), 4.05 (m, 4H, 2×NCH$_2$), 4.67 (d, 1H, J=21 Hz, 3'-H), 5.25 (d, 1H, J=54 Hz, 2'-H), 6.24 (d, 1H, J=9.0 Hz, 5-H), 6.57 (d, 1H, J=12 Hz, 1'-H), 7.82 (d, 1H, J=9.0 Hz, 6-H); $^{13}$C NMR (75 MHz, DMSO$_{d6}$) δ 27.7 (2×CH$_2$), 63.4 (3×CH$_2$), 76.3 (3'-CH, d, J=24.8 Hz), 84.2 (1'-CH, d, J=17.3 Hz), 92.5 (5-CH), 96 (2'-CH, d, $J_{FC}$=192 Hz), 98.3 (4'-C, d, J=7.5 Hz), 143.2 (6-CH), 156.8 (4-C), 163.6 (CO). HRMS (ESI) calcd for $C_{13}H_{17}FN_6O_4SNa$ [M+Na]$^+$ 395.0914. found 395.0913; calcd for $C_{13}H_{18}FN_6O_4S$ [M+H]$^+$ 373.1094. found 373.1093.

Compound 5-30: $^1$H NMR (300 MHz, CD$_4$O): δ 3.85 (2H, s, 5'-CH$_2$), 4.49 (1H, dd, J=21.8 and 4.7, 3'-H), 5.21 (1H, d, J=53.6, 2'-H), 5.93 (1H, s, 5-H), 6.47 (1H, dd, J=11.9 and 4.9, 1'-H), 7.61 (1H, s, 6-H); $^{13}$C NMR (75 MHz, CD$_4$O): δ 63.4 (5'-CH$_2$), 76.4 (3'-CH, d, J 24.9), 84.6 (1'-CH), 92.6 (5-CH), 96.2 (2'-CH, d, $J_{FC}$ 192.4), 98.6 (4'-C), 144.1 (6-CH), 156.7 (4-C), 161.9 (CO); HRMS (ESI) calcd for $C_{10}H_{13}FN_8O_5Na$ [M+Na]$^+$ 367.0891. found 367.0912 (calcd for $C_{13}H_{20}FN_6O_6$ [M+H]$^+$ 345.1071. found 345.1103).

Compound 5-32: $^1$H NMR (300 MHz, CD$_4$O): δ 2.01 (2H, m, NHCH$_2$CH$_2$CH$_2$NH$_2$), 3.15 (2H, t, J=6.4, NHCH$_2$CH$_2$CH$_2$NH$_2$), 3.43 (2H, t, J=5.8, NHCH$_2$CH$_2$CH$_2$NH$_2$), 3.85 (2H, s, 5'-CH$_2$), 4.52 (1H, dd, J=22.1 and 4.6, 3'-H), 5.31 (1H, dt, J=53.6 and 5.0, 2'-H), 5.93 (1H, d, J=7.6, 5-H), 6.49 (1H, dd, J=11.8 and 5.0, 1'-H), 7.68 (1H, d, J=7.6, 6-H); $^{13}$C NMR (75 MHz, CD$_4$O): δ 33.0, 35.1, 40.0 and 63.4 (all CH$_2$), 76.4 (3'-CH, d, J 25.1), 84.5 (1'-CH, d, J 17.4), 96.2 (2'-CH, d, $J_{FC}$ 192.3), 97.2 (5-CH), 98.6 (4'-C, d, J 7.4), 141.5 (6-CH), 158.2 (4-C), 166.1 (CO); HRMS (ESI) calcd for $C_{12}H_{18}FN_7O_4Na$ [M+Na]$^+$ 366.1302. found 366.1339 (calcd for $C_{12}H_{19}FN_7O_4$ [M+H]$^+$ 344.1483. found 344.1526).

Compound 5-33: $^1$H NMR (300 MHz, CD$_4$O): δ 2.63 (2H, m, NHCH$_2$CH(OH)CH$_2$NH$_2$), 3.25 (2H, m, NHCH$_2$CH(OH)CH$_2$NH$_2$), 3.75 (1H, m, NHCH$_2$CH(OH)CH$_2$NH$_2$), 3.86 (2H, s, 5'-CH$_2$), 4.52 (1H, dd, J=22.0 and 4.7, 3'-H), 5.22 (1H, dt, J=53.8 and 4.9, 2'-H), 5.99 (1H, d, J=7.6, 5-H), 6.49 (1H, dd, J=11.8 and 5.2, 1'-H), 7.70 (1H, dd, J=7.6 and 0.9, 6-H); $^{13}$C NMR (75 MHz, CD$_4$O): δ 39.8, 42.7 and 63.3 (all CH$_2$), 73.1 (NHCH$_2$CH(OH)CH$_2$NH$_2$), 76.3 (3'-CH, d, J 24.8), 84.5 (1'-CH, d, J 17.0), 96.2 (2'-CH, d, $J_{FC}$ 192.1), 97.3 (5-CH), 98.5 (4'-C, d, J 8.1), 141.6 (6-CH), 158.1 (4-C), 166.2 (CO); HRMS (ESI) calcd for $C_{12}H_{18}FN_7O_5Na$ [M+Na]$^+$ 382.1251. found 382.1290 (calcd for $C_{12}H_{19}FN_7O_5$ [M+H]$^+$ 360.1432. found 360.1468).

Example 4

Synthesis of amino acid methyl ester hydrochloride is described as follows. Amino acid is placed into a 50 ml one-port flask and added with 2.0 eq. TMSCl dropwise before adding 5 mL of dry methanol as the solvent. The reaction mixture is sealed and allowed to react at room temperature with stirring for 24 h. Upon completion of the reaction, the solvent is evaporated and methanol (3×10 mL) is further added to co-evaporate the residual hydrochloride. Ethyl ether is then added to the oily product obtained after the evaporation and a white solid is precipitated and further recrystallized with methanol-ethyl ether. Experimental data for the products are shown in the table below.

TABLE 2

| Entry | Starting material | Yield | Product |
|---|---|---|---|
| E1 | $NH_2CH_2COOH$ | 90% | $NH_2CH_2COOCH_3 \cdot HCl$ |
| E2 | HOOC-CH(NH$_2$)-COOH | 90% | $H_3COOC$-CH(NH$_2 \cdot HCl$)-COOCH$_3$ |
| E3 | (CH$_3$)$_2$CH-CH(NH$_2$)-COOH | 75% | (CH$_3$)$_2$CH-CH(NH$_2 \cdot HCl$)-COOCH$_3$ |
| E4 | CH$_3$S-CH$_2$CH$_2$-CH(NH$_2$)-COOH | 68% | CH$_3$S-CH$_2$CH$_2$-CH(NH$_2 \cdot HCl$)-COOCH$_3$ |
| E5 | HO-CH$_2$-CH(NH$_2$)-COOH | 83% | HO-CH$_2$-CH(NH$_2 \cdot HCl$)-COOCH$_3$ |
| E6 | HS-CH$_2$-CH(NH$_2$)-COOH | 70% | HS-CH$_2$-CH(NH$_2 \cdot HCl$)-COOCH$_3$ |
| E7 | Ph-CH$_2$-CH(NH$_2$)-COOH | 92% | Ph-CH$_2$-CH(NH$_2 \cdot HCl$)-COOCH$_3$ |

The NMR data of typical products listed in the above table are shown below.

Product E2: $^1$H NMR (300 MHz) δ 8.78 (s, 2H), 4.33 (t, 1H, J=6.0 Hz), 3.73 (s, 3H), 3.65 (s, 3H), 3.03 (q, 2H, J=3.0 Hz).

Product E3: $^1$H NMR (300 MHz) δ 8.55 (s, 1H), 3.87 (d, 1H, J=3.0 Hz), 3.76 (s, 3H), 2.18 (dd, 1H, J=12.0 Hz, J=6.0 Hz), 0.96 (q, 6H, J=6.0 Hz).

Product E4: $^1$H NMR (300 MHz) δ 8.87 (s, 2H), 4.08 (t, 1H, J=6.0 Hz), 3.76 (s, 3H), 3.00 (d, 1H, J=9.0 Hz), 2.53-2.50 (m, 1H), 2.14 (m, 1H), 2.11 (q, 2H, J=6.0 Hz), 2.06 (s, 3H).

Product E5: $^1$H NMR (300 MHz) δ 5.64 (s, 1H), 4.09 (d, 1H, J=3.0 Hz), 3.84 (d, 2H, J=3.0 Hz), 3.74 (s, 3H).

Product E6: $^1$H NMR (300 MHz) δ 4.36 (d, 1H, J=6.0 Hz), 3.77 (s, 3H), 3.02 (dd, 2H, J=6.0 Hz, J=3.0 Hz).

Product E7: $^1$H NMR (300 MHz) δ 8.70 (s, 2H), 7.37-7.23 (m, 5H), 4.26 (s, 1H), 3.66 (s, 3H), 3.12 (dd, 2H, J=18.0 Hz, J=12.0 Hz).

Example 5

Synthesis of pyrimidine nucleoside derivatives substituted with amino acid and corresponding building blocks is shown in Scheme D.

Scheme D. Synthesis of a pyrimidine nucleoside derivative with amino acid substitution at position 4.

4 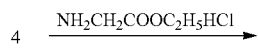

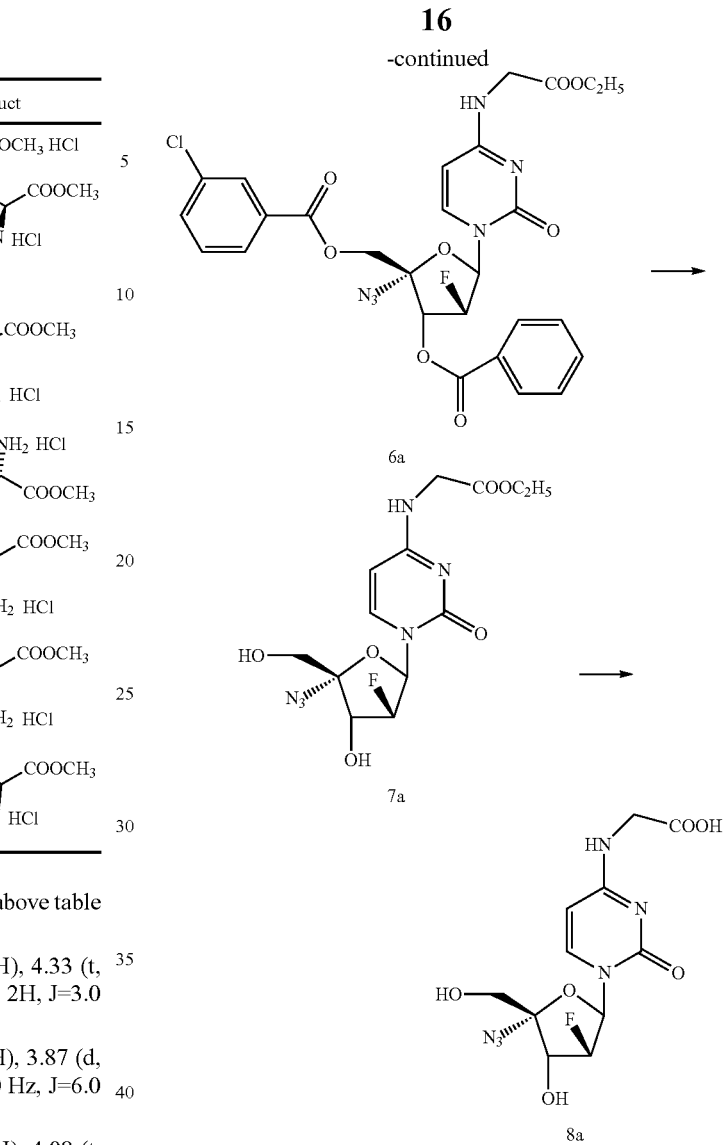

Synthesis of compound 6a: Glycine ethyl ester hydrochloride (17.0 mg, 0.12 mmol, 2.0 eq.), diisopropylethylamine (14.0 mg, 0.12 mmol, 2.0 eq.) and catalytic amount of DMAP are added to compound 4 (50.0 mg, 0.06 mmol, 1.0 eq.) dissolved in 15 mL dry DMF and the obtained colorless and clear solution is stirred at room temperature for 3 h. The reaction process is monitored by TLC. Upon completion, the reaction solution is added with water and extracted with ethyl acetate. Dry the organic phase over anhydrous sodium sulfate, filtrate and remove the solvent. The crude product is purified on a silica column using ethyl acetate:petroleum ether=2:3 ($R_f$=0.35) as the eluent. The obtained light yellow oily product 6a is weighed 16 mg corresponding to a yield of 45%.

Synthesis of compound 7a: Lithium hydroxide (16.0 mg, 0.38 mmol, 6.0 eq.) is added to compound 6a (29 mg, 0.06 mmol, 1.0 eq.) dissolved in a mixture of 7 mL THF, 1 mL H$_2$O and 1 mL CH$_3$OH. The reaction solution is directly evaporated after being stirred for two hours. The crude product is purified with TLC plate using DCM:CH$_3$OH=2.2:1 ($R_f$=0.3) as the developing agent. $^1$H NMR (300 MHz) δ 7.95 (s, 1H), 7.58 (s, 1H), 7.51 (d, 1H, J=9.0 Hz), 6.38 (q, 1H, J=6.0 Hz), 6.07 (d, 1H, J=6.0 Hz), 5.27-5.05 (dt, 1H, J=54 Hz, J=6.0 Hz), 4.49 (dd, 1H, J=24 Hz, J=6.0 Hz), 3.73 (dd, 2H, J=12 Hz, J=18 Hz), 3.58 (d, 2H, J=6.0 Hz), 1.06 (t, 3H, J=7.5 Hz).

Synthesis of compound 8a: The pyrimidine derivative 8a with amino acid substitution at position 4 is obtained through the hydrolysis of compound 7a by potassium hydroxide.

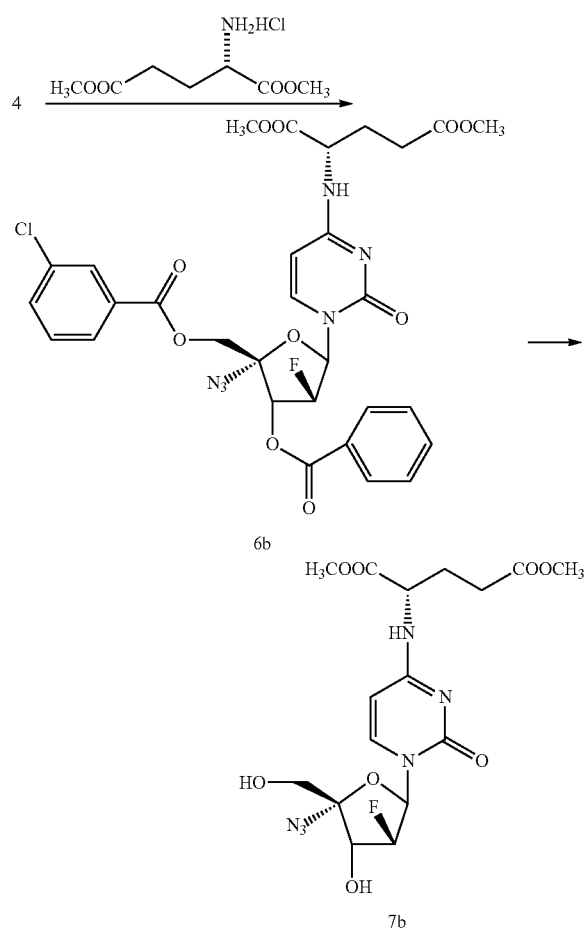

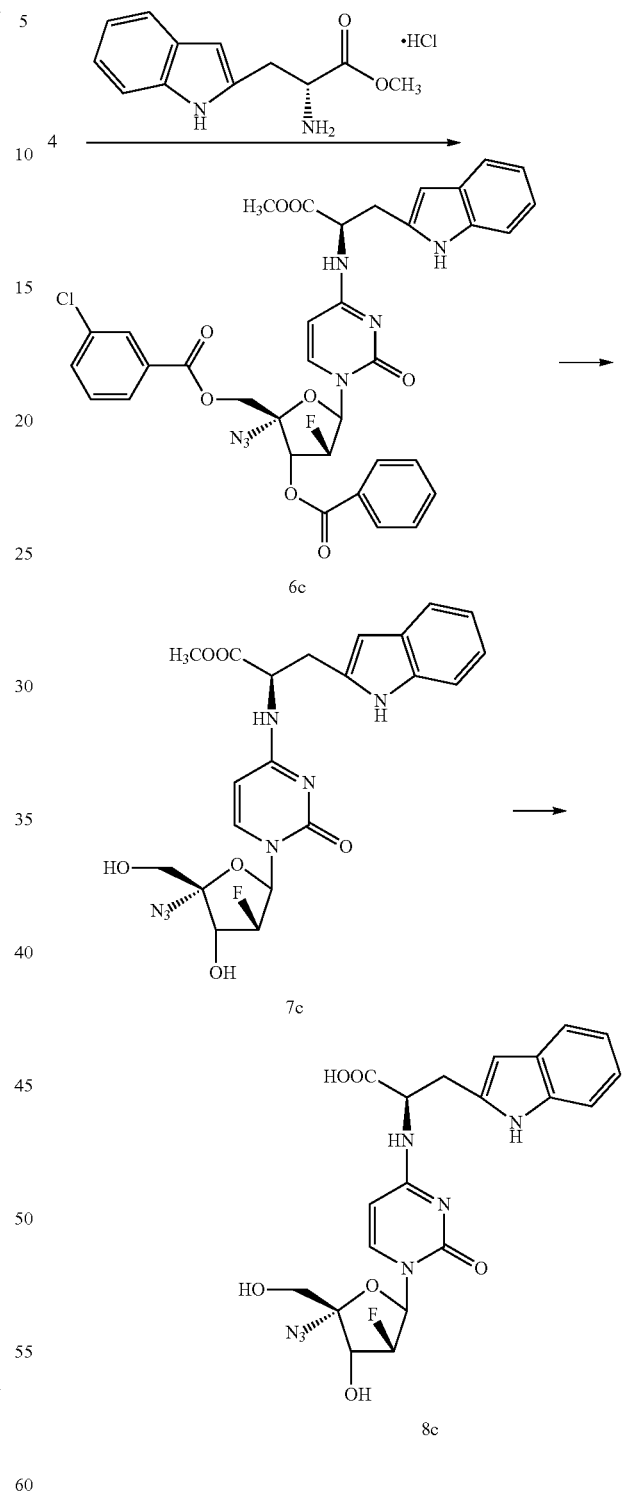

Synthesis of compound 6b: Under the protection of $N_2$, 5 mL dry acetonitrile and diisopropylethylamine (96.6 mg, 0.75 mmol, 3.0 eq.) are added to compound 4 (200.0 mg, 0.25 mmol, 1.0 eq.), L-glutamic acid dimethyl ester hydrochloride (76.8 mg, 0.30 mmol, 1.2 eq.) and catalytic amount of DMAP (15.0 mg, 0.13 mmol, 0.5 eq.) placed in a 50 mL one-port flask, and the obtained colorless and clear solution is stirred to react at room temperature overnight, giving a light yellow solution. The reaction process is monitored by TLC. Upon completion, the reaction solution is added with water giving a white suspension which is then extracted with ethyl acetate for three times. Dry the organic phase over anhydrous sodium sulfate, filtrate and remove the solvent. The crude product is purified on a silica column using ethyl acetate:petroleum ether=1:1 ($R_f$=0.4) as the eluent. The obtained light yellow oily product 6b is weighed 125 mg corresponding to a yield of 72%.

Synthesis of compound 7b is performed in a similar manner as described above.

Synthesis of compound 6c: Under the protection of $N_2$, 5 mL dry acetonitrile is added to compound 4 (200.0 mg, 0.25 mmol, 1.0 eq.), D-tryptophan methyl ester hydrochloride (76.8 mg, 0.30 mmol, 1.2 eq.) and catalytic amount of DMAP (15.0 mg, 0.13 mmol, 0.5 eq.) placed in a 50 mL one-port flask. The solid does not dissolve until diisopropylethylamine (96.6.0 mg, 0.75 mmol, 3.0 eq.) is further added dropwise.

The obtained colorless and clear solution is stirred to react at room temperature overnight. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate: petroleum ether=2:1 ($R_f$=0.5). The obtained light yellow oily product 6c is weighed 105 mg corresponding to a yield of 57%.

Synthesis of compound 7c: Lithium hydroxide (27.7 mg, 0.66 mmol, 6.0 eq.) is added to compound 6c (80 mg, 0.11 mmol, 1.0 eq.) dissolved in a mixture of 7 mL THF, 1 mL $H_2O$ and 1 mL $CH_3OH$. The reaction solution is allowed to react for two hours with stirring before the following work-up procedure: adjusting the pH of the solution to around 3 with diluted HCl; performing extraction with ethyl acetate for three times, then drying over anhydrous sodium sulfate and purification on TLC plate using DCM:$CH_3OH$=3:1 ($R_f$=0.3). Product 7c is thus obtained.

Synthesis of compound 8c is performed in a similar manner as described above.

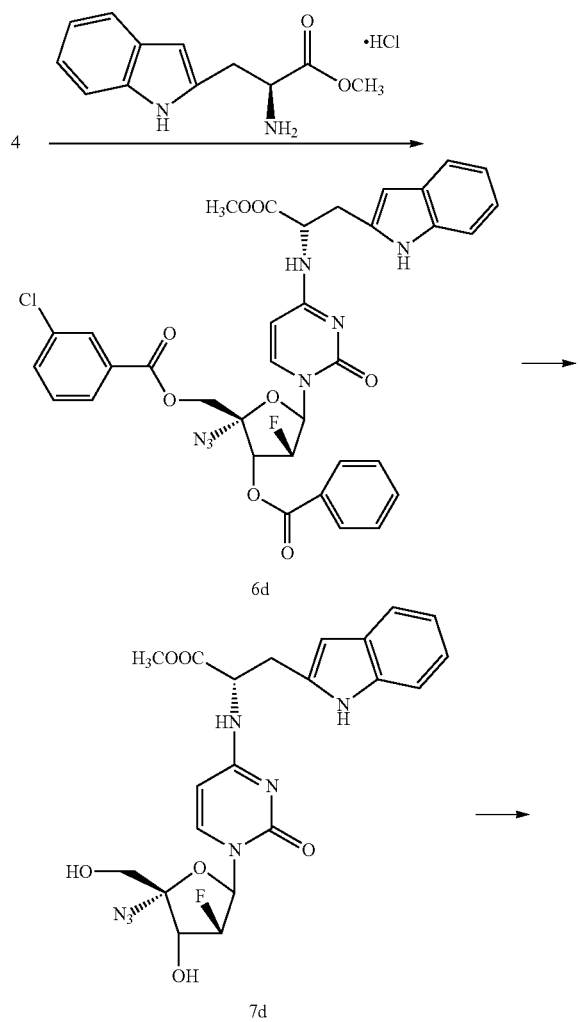

Scheme G. Synthesis of a pyrimidine nucleoside derivative with amino acid substitution at position 4.

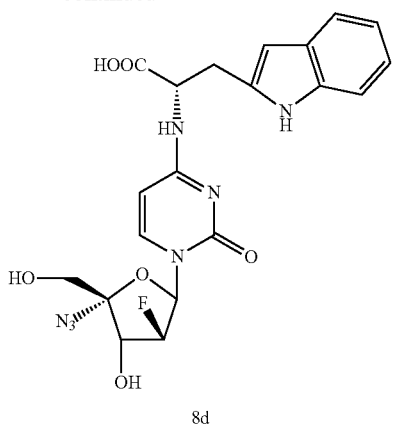

8d

Synthesis of compound 6d: DMAP (15.0 mg, 0.13 mmol, 0.5 eq.) and L-tryptophan methyl ester hydrochloride (76.8 mg, 0.30 mmol, 1.2 eq.) are added to compound 4 (200.0 mg, 0.25 mmol, 1.0 eq.) dissolved in 15 mL dry acetonitrile and do not dissolve until diisopropylethylamine (96.60 mg, 0.75 mmol, 3.0 eq.) is further added to the solution. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate:petroleum ether=2:1 ($R_f$=0.5). The obtained light yellow oily product 6d is weighed 165 mg corresponding to a yield of 90%.

Synthesis of compound 7d: Lithium hydroxide (90.7 mg, 2.16 mmol, 9.0 eq.) is added to compound 6d (175 mg, 0.24 mmol, 1.0 eq.) dissolved in a mixture of 14 mL THF, 2 mL $H_2O$ and 2 mL $CH_3OH$. The reaction solution is allowed to react for two hours with stirring before the following work-up procedure: adjusting the pH of the solution to around 3 with diluted HCl; performing extraction with ethyl acetate for three times, then drying over anhydrous sodium sulfate and purification on TLC plate using DCM:$CH_3OH$=3:1 ($R_f$=0.3). Product 7d is thus obtained.

Synthesis of compound 8d: Compound 8d is synthesized in a similar manner as described above.

Scheme H. Synthesis of a pyrimidine nucleoside derivative with amino acid substitution at position 4.

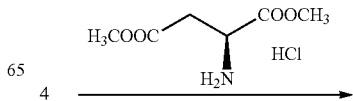

4

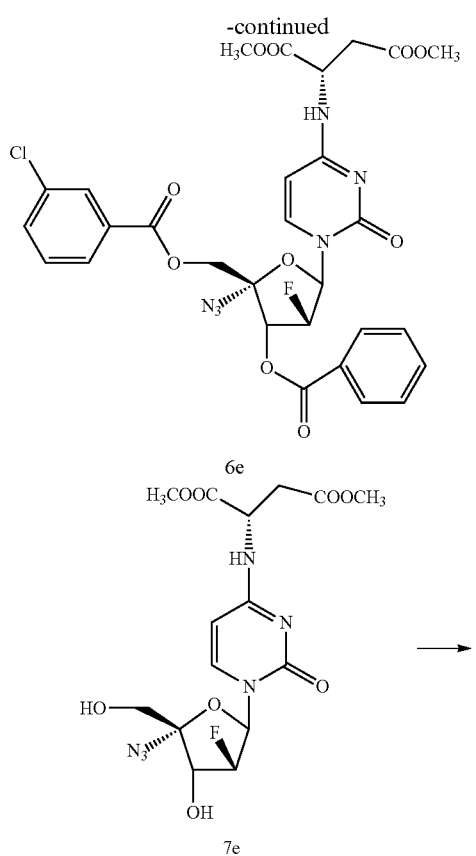

6e

7e

8e

Synthesis of compound 6e: Catalytic amount of DMAP, L-aspartic acid methyl ester hydrochloride (120.0 mg, 0.72 mmol, 2.0 eq.) and diisopropylethylamine (139.0 mg, 1.08 mmol, 3.0 eq.) are added to compound 4 (300 mg, 0.36 mmol, 1.0 eq.) dissolved in 15 mL dry DMF and dissolve completely. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. Use a gradient elution of ethyl acetate:petroleum ether=1:1-2:1 (Rf=0.5) to run the column. The obtained light yellow oily product 6e is weighed 130 mg corresponding to a yield of 54%.

Synthesis of compound 7e: Compound 7e is synthesized in a similar manner as described above.

Synthesis of compound 8e: Compound 8e is synthesized in a similar manner as described above.

Scheme I. Synthesis of a pyrimidine nucleoside derivative with amino acid substitution at position 4.

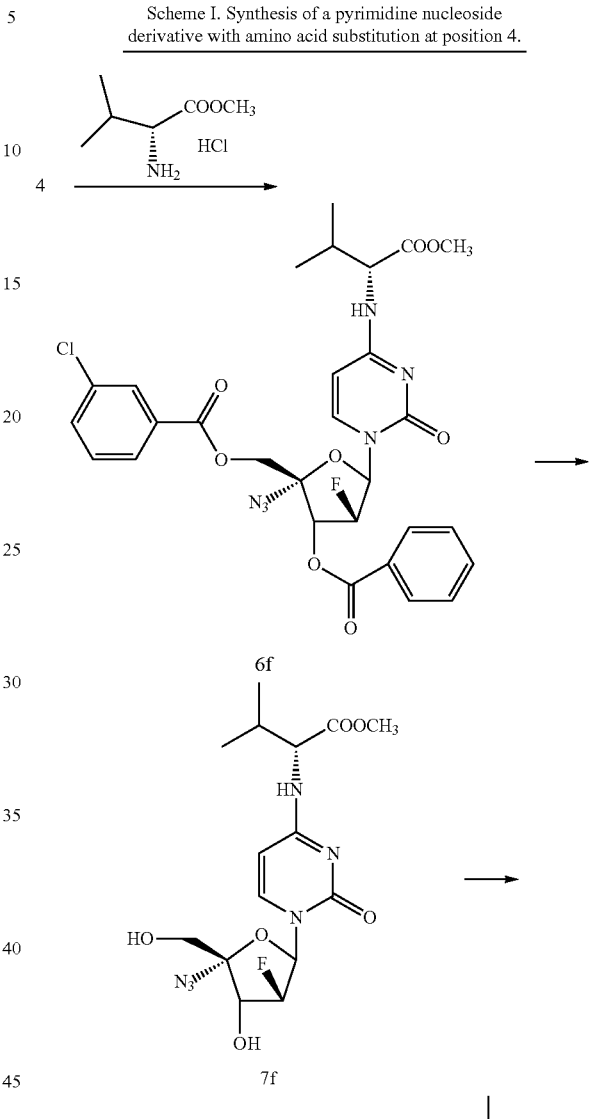

6f

7f

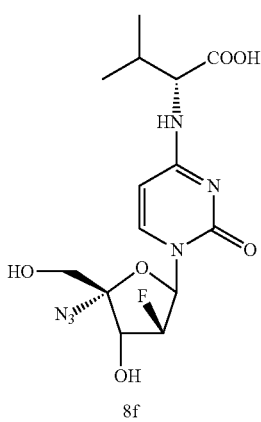

8f

Synthesis of compound 6f: DMAP (15.0 mg, 0.13 mmol, 0.5 eq.) and D-3-methyl-2-aminobutyric acid methyl ester hydrochloride (49.0 mg, 0.38 mmol, 1.5 eq.) are added to compound 4 (200.0 mg, 0.25 mmol, 1.0 eq.) dissolved in 15 mL dry acetonitrile and do not dissolve. The solids remain undissolved after the addition of diisopropylethylamine (129.0 mg, 1.00 mmol, 4.0 eq.) and even after the further addition of 10 mL DMF. The obtained white suspension is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate:petroleum ether=2:3 ($R_f$=0.5). The obtained light yellow oily product 6f is weighed 52 mg corresponding to a yield of 32%. $^1$HNMR (300 MHz) δ 8.19 (d, 1H, J=9.0 Hz), 8.04 (d, 2H, J=6.0 Hz), 7.88 (d, 2H, J=3.0 Hz), 7.76-7.71 (m, 3H), 7.57 (t, 2H, J=7.5 Hz), 7.49 (t, 1H, J=7.5 Hz), 6.63 (d, 1H, J=9.0 Hz), 6.17 (d, 1H, J=21 Hz), 6.07 (d, 1H, J=6.0 Hz), 5.90-5.70 (m, 1H, J=54 Hz, J=6.0 Hz), 4.93 (dd, 2H, J=12 Hz, J=15 Hz), 4.51 (q, 1H, J=6.0 Hz), 3.67 (s, 3H), 2.13 (dd, 1H, J=7.5 Hz, J=15.0 Hz), 0.95 (t, 6H, J=7.5 Hz).

Synthesis of compound 7f: Compound 7f is synthesized in a similar manner as described above.

Synthesis of compound 8f: Compound 8f is synthesized in a similar manner as described above.

Scheme J.
Synthesis of a pyrimidine nucleoside derivative with amino acid substitution at position 4.

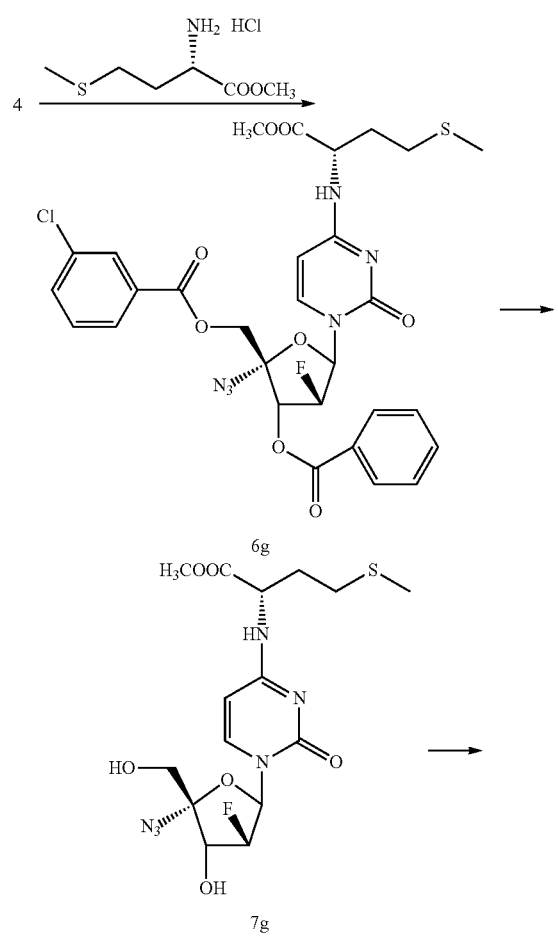

Synthesis of compound 6g: DMAP (15.0 mg, 0.13 mmol, 0.5 eq.) and L-methionine methyl ester hydrochloride (55.3 mg, 0.28 mmol, 1.1 eq.) are added to compound 4 (200.0 mg, 0.25 mmol, 1.0 eq.) dissolved in 15 mL dry acetonitrile and do not dissolve. The solids remain undissolved after the addition of diisopropylethylamine (130.0 mg, 1.00 mmol, 4.0 eq.) and only dissolve until 2 mL DMF is added. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate: petroleum ether=1:2 ($R_f$=0.1). The product 6g is thus obtained.

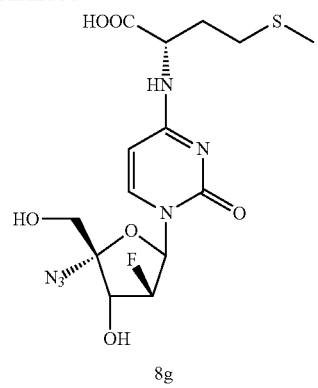
8g

Synthesis of compound 7g: Compound 7g is synthesized in a similar manner as described above.

Synthesis of compound 8g: Compound 8g is synthesized in a similar manner as described above.

Scheme K.
Synthesis of a pyrimidine nucleoside derivative with amino acid substitution at position 4.

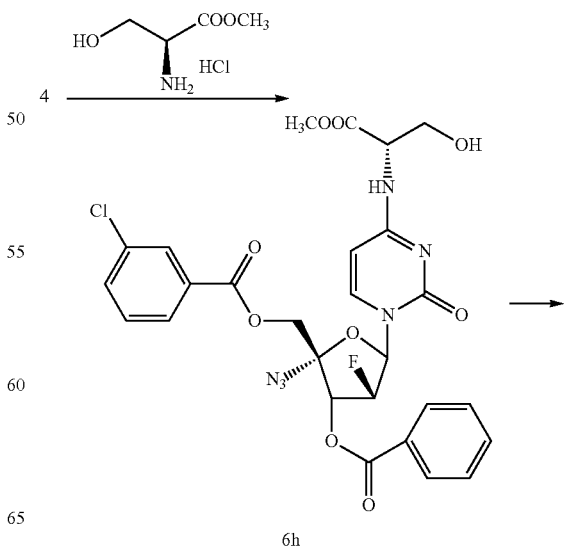

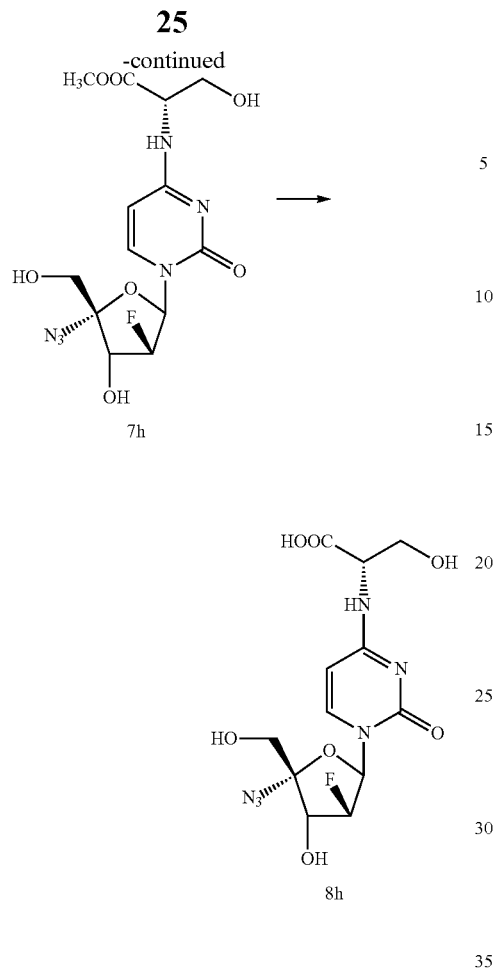

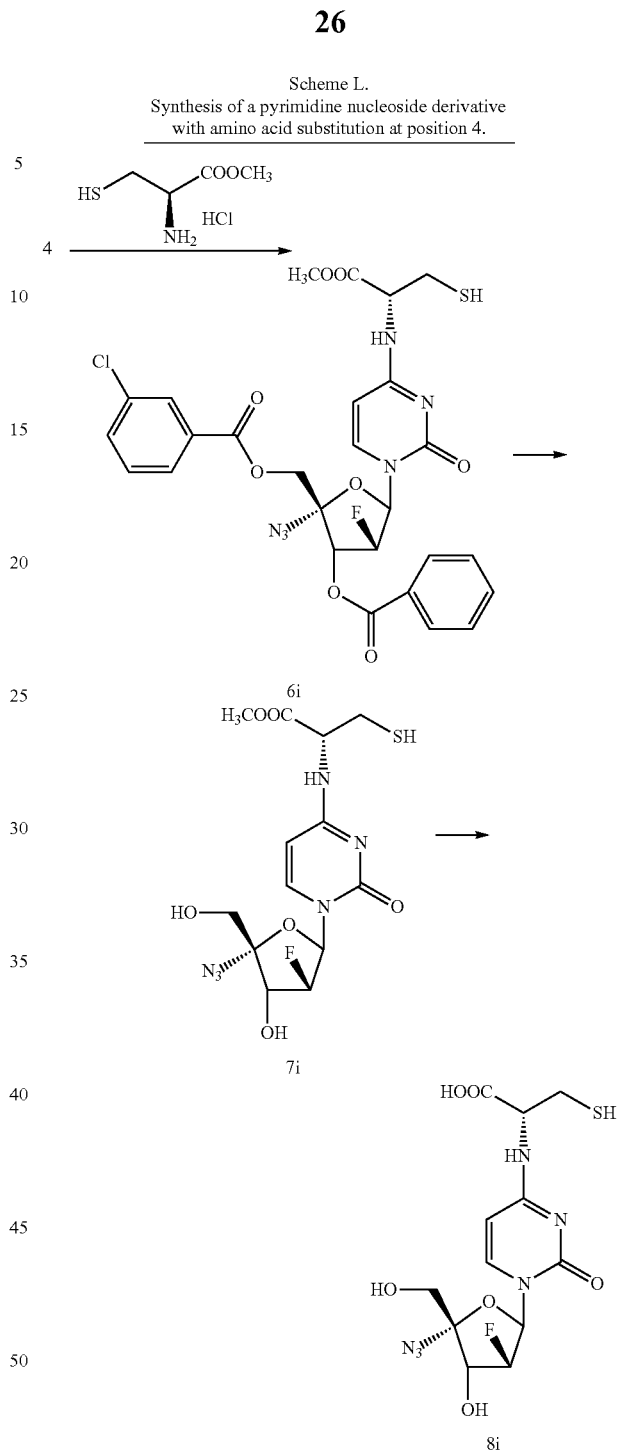

Scheme L.
Synthesis of a pyrimidine nucleoside derivative with amino acid substitution at position 4.

Synthesis of compound 6h: DMAP (15.0 mg, 0.13 mmol, 0.5 eq.) and L-serine methyl ester hydrochloride (60.0 mg, 0.40 mmol, 1.5 eq.) are added to compound 4 (200.0 mg, 0.25 mmol, 1.0 eq.) dissolved in 15 mL dry acetonitrile and do not dissolve. The solids remain undissolved after the addition of diisopropylethylamine (134.0 mg, 1.04 mmol, 4.0 eq.) and even after the further addition of 10 mL DMF. The color of the white suspension gradually darkens and at the end, an orange suspension is obtained, which is stirred to react at room temperature overnight. The reaction process is monitored by TLC. Upon completion, the reaction solution is added with water giving a yellow suspension which is then extracted with ethyl acetate for three times. Both layers are clear. The organic phase is dried over anhydrous sodium sulfate and used for further purification with a TLC method. The developing agent used is ethyl acetate: petroleum ether=2:1 ($R_f$=0.5). The obtained light yellow oily product 6h is weighed 79 mg corresponding to a yield of 50%. $^1$H NMR (300 MHz) δ 8.33 (d, 1H, J=9.0 Hz), 8.03 (t, 2H, J=4.5 Hz), 7.86 (t, 2H, J=3.0 Hz), 7.74-7.71 (m, 3H), 7.60-7.49 (m, 3H), 6.62 (t, 1H, J=6.0 Hz), 6.17 (d, 1H, J=21 Hz), 6.10 (d, 1H, J=9.0 Hz), 5.90-5.69 (dt, 1H, J=54 Hz, J=6.0 Hz), 5.22 (t, 1H, J=4.5 Hz), 4.93 (dd, 2H, J=12 Hz, J=15 Hz), 4.72-4.66 (m, 1H), 3.84-3.75 (m, 2H), 3.65 (s, 3H).

Synthesis of compound 7h: Compound 7h is synthesized in a similar manner as described above.

Synthesis of compound 8h: Compound 8h is synthesized in a similar manner as described above.

Synthesis of compound 6i: DMAP (7.7 mg, 0.06 mmol, 0.5 eq.) and L-cysteine methyl ester hydrochloride (32.4 mg, 0.19 mmol, 1.5 eq.) are added to compound 4 (100.0 mg, 0.13 mmol, 1.0 eq.) dissolved in 15 mL dry acetonitrile and do not dissolve until diisopropylethylamine (65.0 mg, 0.50 mmol, 4.0 eq.) is further added to the solution. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate:petroleum ether=2:1 ($R_f$=0.6). The product 6i is thus obtained.

Synthesis of compound 7i: Compound 7i is synthesized in a similar manner as described above.

Synthesis of compound 8i: Compound 8i is synthesized in a similar manner as described above.

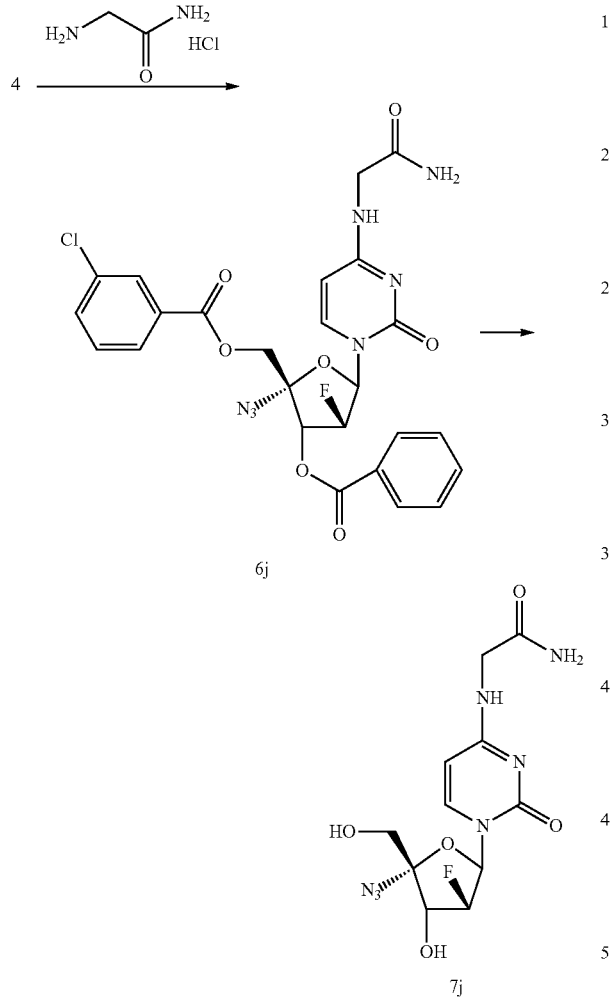

Synthesis of compound 6j: Catalytic amount of DMAP, glycinamide hydrochloride (56.0 mg, 0.48 mmol, 2.0 eq.) and diisopropylethylamine (97.0 mg, 0.75 mmol, 3.0 eq.) are added to compound 4 (200.0 mg, 0.25 mmol, 1.0 eq.) dissolved in 15 mL dry DMF and dissolve completely. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. Run the column with a gradient by using ethyl acetate first to flush out the impurities and then using ethyl acetate added with a small amount of methanol and triethylamine. The obtained product 6j as a purple solid is weighed 88 mg corresponding to a yield of 60%.

Synthesis of compound 7j: Compound 7j is synthesized in a similar manner as described above.

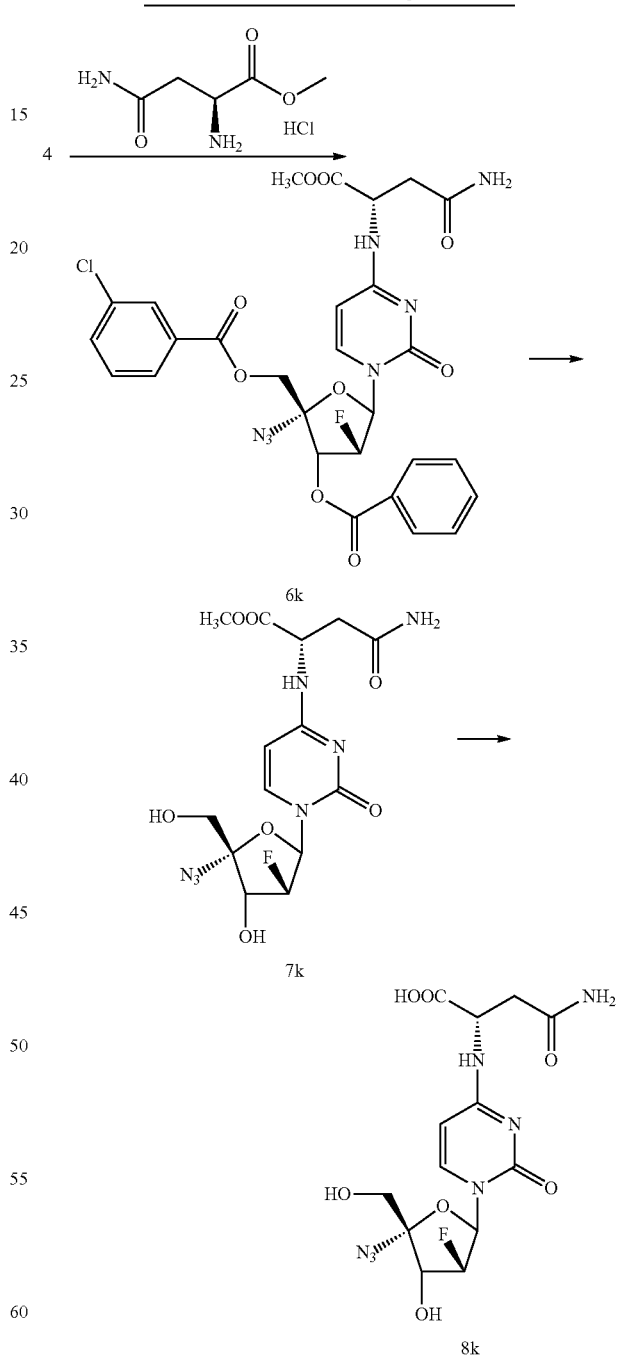

Synthesis of compound 6k: DMAP (7.7 mg, 0.06 mmol, 0.5 eq.) and L-asparagine methyl ester hydrochloride (60.0 mg, 0.13 mmol, 1.5 eq.) are added to compound 4 (100.0 mg, 0.13 mmol, 1.0 eq.) dissolved in 15 mL dry DMF and do not dissolve. The solids remain undissolved after the addition of diisopropylethylamine (67.6.0 mg, 0.52 mmol, 4.0 eq.). The obtained white suspension is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method to afford product 6k.

Synthesis of compound 7k: Compound 7k is synthesized in a similar manner as described above.

Synthesis of compound 8k: Compound 8k is synthesized in a similar manner as described above.

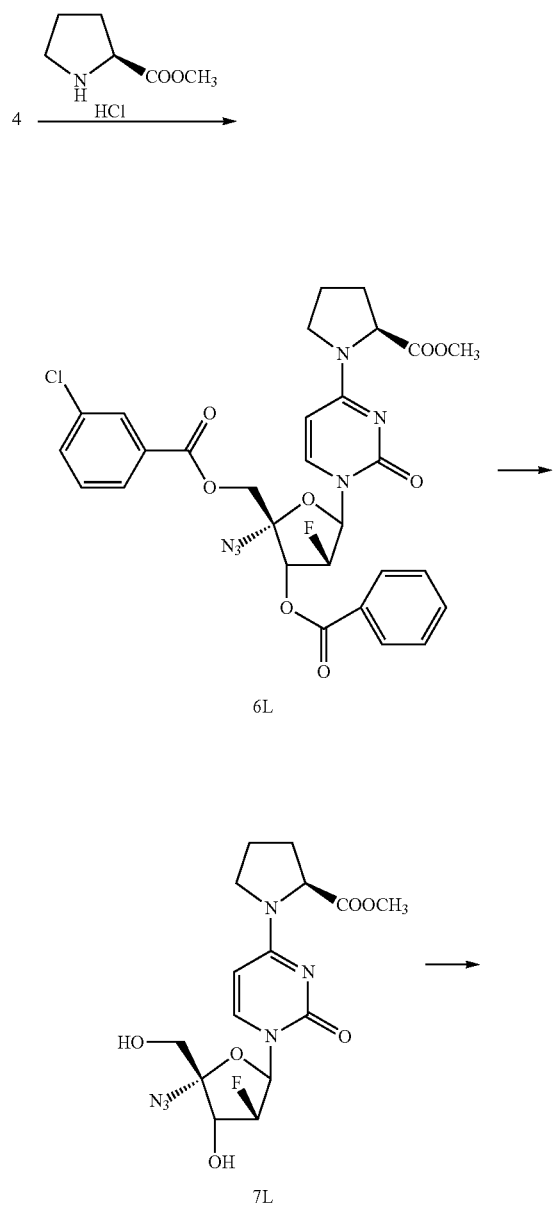

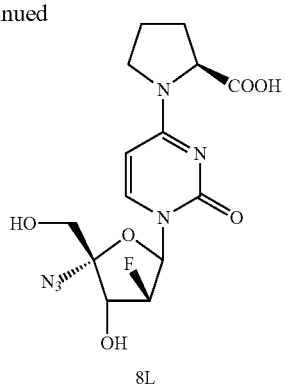

Synthesis of compound 6L: Catalytic amount of DMAP, L-proline methyl ester hydrochloride (120.0 mg, 0.72 mmol, 2.0 eq.) and diisopropylethylamine (139.0 mg, 1.08 mmol, 3.0 eq.) are added to compound 4 (300.0 mg, 0.36 mmol, 1.0 eq.) dissolved in 15 mL dry DMF. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. Run the column with a gradient elution of ethyl acetate:petroleum ether=1:1-2:1 ($R_f$=0.5). The obtained product 6L as a white solid is weighed 200 mg corresponding to a yield of 87%.

Synthesis of compound 7L: Compound 7L is synthesized in a similar manner as described above.

Synthesis of compound 8L: Compound 8L is synthesized in a similar manner as described above.

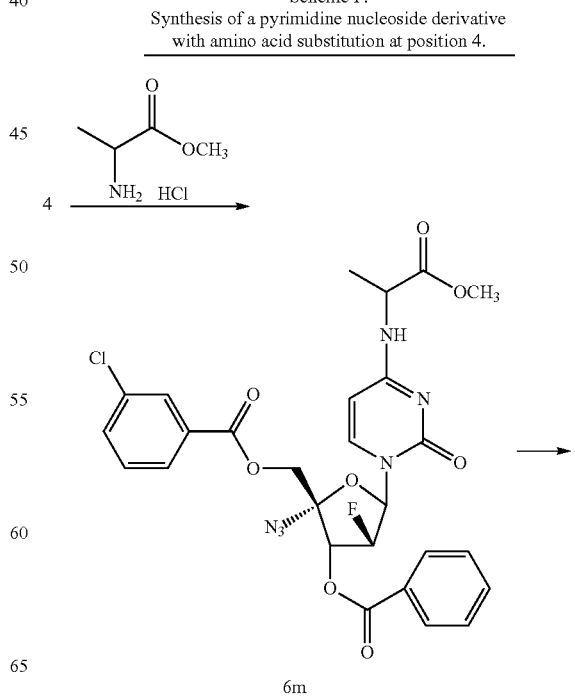

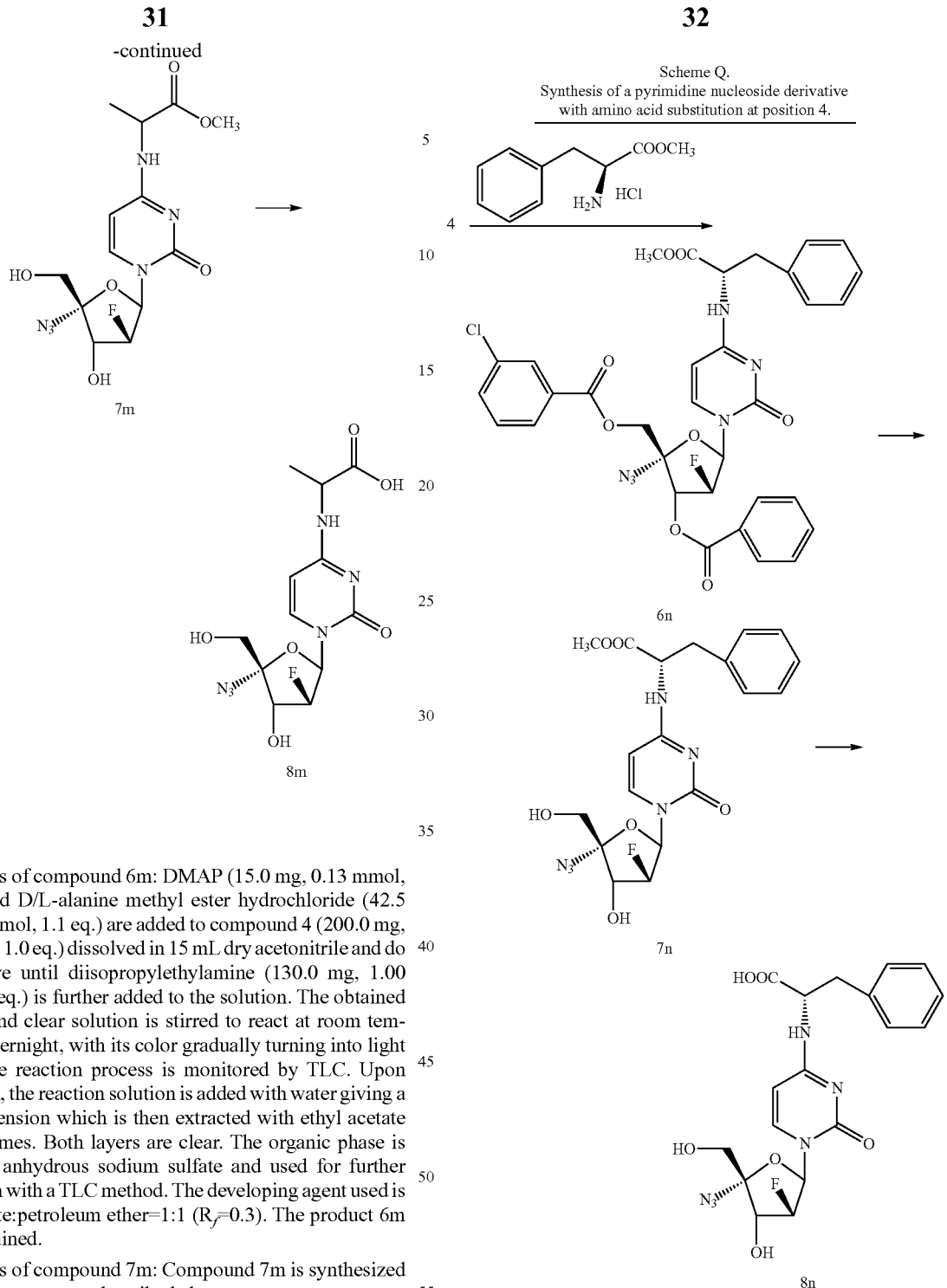

Scheme Q.
Synthesis of a pyrimidine nucleoside derivative with amino acid substitution at position 4.

Synthesis of compound 6m: DMAP (15.0 mg, 0.13 mmol, 0.5 eq.) and D/L-alanine methyl ester hydrochloride (42.5 mg, 0.28 mmol, 1.1 eq.) are added to compound 4 (200.0 mg, 0.25 mmol, 1.0 eq.) dissolved in 15 mL dry acetonitrile and do not dissolve until diisopropylethylamine (130.0 mg, 1.00 mmol, 4.0 eq.) is further added to the solution. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate:petroleum ether=1:1 ($R_f$=0.3). The product 6m is thus obtained.

Synthesis of compound 7m: Compound 7m is synthesized in a similar manner as described above.

Synthesis of compound 8m: Compound 8m is synthesized in a similar manner as described above. m.p 168-170° C. $^1$H NMR (DMSO-$d_6$): δ 8.26 (d, 1H, J=7.0 Hz), 7.60 (d, 1H, J=7.5 Hz), 6.40 (d, 1H, J=3.6 Hz), 6.36 (d, 1H, J=5.4 Hz), 5.90 (d, 1H, J=7.6 Hz), 5.68 (s, 1H), 5.17 (dt, 1H, J=52.3 Hz, J=3.5 Hz), 4.55-4.38 (m, 2H), 3.73 (s, 2H), 3.65 (d, 3H, J=1.6 Hz); $^{13}$C (75 MHz, DMSO-$d_6$): δ 173.1, 163.1, 154.4, 141.3, 97.0 (J=5.1 Hz), 94.7, 94.6 (J=191.9 Hz), 82.2 (J=16.6 Hz), 74.9 (J=24.0 Hz), 62.3, 52.1, 48.4, 17.1; HRMS m/z: for $C_{14}H_{19}FN_6NaO_6$ (M+Na)$^+$: calcd. 395.11. found 395.1140, (M+H)$^+$: calcd. 373.13. found 373.1313.

Synthesis of compound 6n: DMAP (15.0 mg, 0.13 mmol, 0.5 eq.) and L-phenylalanine methyl ester hydrochloride (59.7 mg, 0.28 mmol, 1.1 eq.) are added to compound 4 (200.0 mg, 0.25 mmol, 1.0 eq.) dissolved in 15 mL dry acetonitrile and do not dissolve until diisopropylethylamine (130.0 mg, 1.00 mmol, 4.0 eq.) is further added to the solution. The obtained colorless and clear solution is stirred to react at room temperature overnight, with its color gradually turning into light yellow. The reaction process is monitored by TLC. Upon completion, the reaction solution is added with water giving a white suspension which is then extracted with ethyl acetate for three times. Both layers are clear. The organic phase is dried over anhydrous sodium sulfate and used for further purification with a TLC method. The developing agent used is ethyl acetate:petroleum ether=1:2 ($R_f$=0.1). The product 6n is thus obtained.

Synthesis of compound 7n: Compound 7n is synthesized in a similar manner as described above.

Synthesis of compound 8n: Compound 8n is synthesized in a similar manner as described above.

Example 6

Pyrimidine nucleosides with furanyl substitution at position 5 are synthesized according to the following process.

5.85-5.78 (dd, 1H, $J_1$=1.4 Hz, $J_2$=1.4 Hz, 3'-H), 5.53-5.35 (qq, 1H, 2'-H), 4.96-4.84 (m, 2H, 5'-H); $^{13}$C NMR (75 MHz, CDCl$_3$) δ164.70, 164.47, 159.13, 149.44, 144.43, 135.01, 134.35, 133.91, 130.33, 130.16, 130.12, 128.80, 127.66, 95.64, 94.32, 91.74, 84.00, 83.78, 68.86, 65.05; ESI-MS: m/z 678.0 [M+Na]$^+$.

Synthesis of compound 10: Compound 9 (0.6 g, 0.92 mmol) is weighed into a 50 mL round-bottom flask and added successively with (PPh$_3$)$_2$PdCl$_2$ (0.014 g, 0.018 mmol), anhydrous 1,4-dioxane (25 mL), and 2-(tributylstannyl)furan (1.5 g, 4.14 mmol) to react at 80° C. for 6 h. The solvent is removed under reduced pressure to give a crude product that is purified on a silica column (TLC, ethyl acetate:petroleum ether=1:1, $R_f$=0.57) using a mixed solvent of ethyl acetate: petroleum

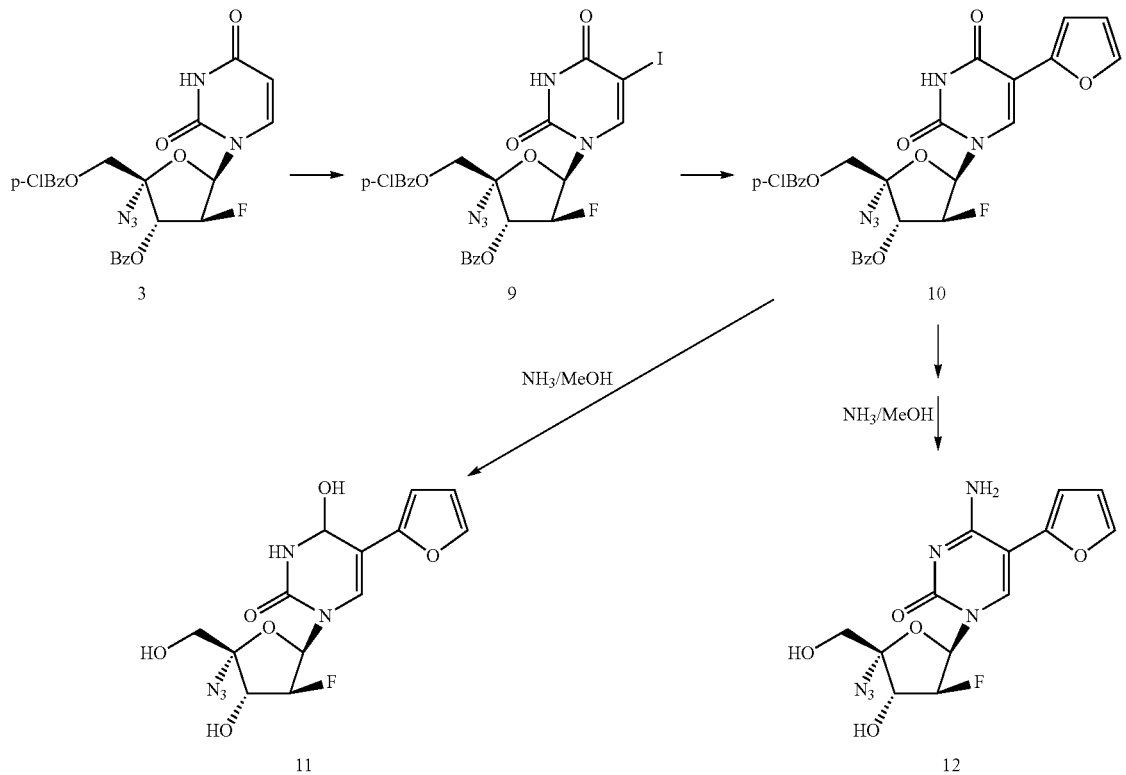

Scheme R.
Synthesis of pyrimidine nucleoside derivatives with furan substitution at position 5.

Synthesis of compound 9: Compound 3 (1.0 g, 1.89 mmol), anhydrous acetonitrile (35 mL), NaN$_3$ (0.614 g, 9.45 mmol) and ICl (0.921 g, 5.67 mmol) in 7 mL anhydrous acetonitrile are added to a 100 mL round-bottom flask to dissolve the solid. The reaction mixture is heated to 50° C. with stirring and allowed to continuously react for 3 days under this condition. Then the reaction mixture is cooled down to room temperature and added with the saturated aqueous solution of sodium sulfite till the solution color fades, and then is extracted with dichloromethane for three times. Dry the organic phase, filtrate and evaporate to dry. The residue is purified on a silica column with ethyl acetate: petroleum ether=1:1 as the eluent ($R_f$=0.566) and compound 9 as a white powder is thus obtained (1.2 g, yield: 97.6%). $^1$H NMR (300 MHz, CDCl$_3$) δ8.80 (s, 1H, NH), 8.10-7.73 (m, 10H, Ar— and 6-H), 6.63-6.55 (dd, 1H, $J_1$=3.4 Hz, $J_2$=3.4 Hz, 1'-H), ether as the eluent. Compound 10 that is slightly yellow is thus obtained (0.6 g, yield: 98%). $^1$H NMR (300 MHz, CDCl$_3$) δ 8.89 (bs, 1H, NH), 8.12-7.26 (m, 10H, Ar— and 6-H), 7.05-7.03 (m, 2H, 5-furan), 6.75-6.67 (dd, $J_1$=3.6 Hz, $J_2$=3.6 Hz, 1H, 1'-H), 6.40-6.39 (m, 1H, 5-furan), 5.94-5.86 (dd, 1H, $J_1$=1.6 Hz, $J_2$=1.6 Hz, 3'-H), 5.60-5.342 (qq, 1H, 2'-H), 4.92-4.89 (m, 2H, 5'-H); $^{13}$C NMR (75 MHz, CDCl$_3$) δ164.74, 164.42, 159.38, 149.00, 144.96, 141.46, 134.82, 134.29, 133.69, 133.28, 130.52, 130.17, 130.11, 129.88, 128.78, 127.99, 111.72, 110.02, 107.58, 95.52, 95.48, 94.52, 91.94, 84.06, 83.83, 65.88. ESI-MS: m/z 618.1 [M+Na]$^+$.

Synthesis of compound 11: Compound 10 (98.6 mg, 0.17 mmol) is weighed into a 50 mL round-bottom flask and added with saturated ammonia methanol solution (20 mL) to react at room temperature for 24 h. Use the dry method to load the reaction solution on a column and run the column with dichloromethane: methanol=10:1 ($R_f$=0.45) to give compound 11 (34.6 mg, 0.098 mmol, yield: 59.3%). $^1$H NMR (300 MHz, CD$_3$OD) δ 8.21 (s, 1H, 6-H), 7.47 (s, 1H, 5-furan), 6.94 (s, 1H, 5-furan), 6.95 (s, 1H, 5-furan), 6.58-6.53 (dd, J$_1$=5.6 Hz, J$_2$=5.6 Hz, 1H, 1'-H), 6.48-6.46 (m, 1H, 5-furan), 5.39-5.18 (tt, 1H, 3'-H), 4.66-4.59 (dd, 1H, J$_1$=5.4 Hz, J$_2$=5.4 Hz, 2'-H), 3.32-3.30 (m, 2H, 5'-H); $^{13}$C NMR (75 MHz, CD$_3$OD) δ162.09, 151.16, 147.49, 142.81, 135.98, 112.55, 110.03, 108.00, 98.44, 98.32, 97.429, 94.85, 83.74, 83.51, 75.93, 62.63.

Synthesis of compound 12: Triazole (0.282 g) and pyridine (330 μL) are added successively with stirring into compound 10 (0.221 g, 0.371 mmol) and anhydrous dichloromethane (5 mL) in a reaction vessel. While being cooled in an ice bath, the resulted mixture is added with POCl$_3$ (173 μL) slowly. Stir for two hours and additional triazole (0.282 g) and POCl$_3$ (173 μL) are further added. Continue to stir overnight. Then the reaction is quenched by adding water. The mixture is extracted with dichloromethane for four times. Dry the organic phase and then evaporate the solvent. Tetrahydrofuran (20 mL) and aqueous ammonia (20 mL) are added. Stir for one hour. Then evaporate the solvent again and add ammonia methanol solution (40 mL) to stir over night. Run a large plate with CH$_2$Cl$_2$: CH$_3$OH=9:1 ($R_f$=0.32) to give compound 12 (18.6 mg, yield: 14.24%). $^1$H NMR (300 MHz, CD$_3$OD) δ 8.17 (s, 1H, 6-H), 7.61 (s, 1H, 5-furan), 6.60-6.51 (s, 3H, 1'-H and 5-furan), 5.38-5.17 (tt, 1H, 3'-H), 4.58-4.49 (dd, 1H, J$_1$=5.14 Hz, J$_2$=5.15 Hz, 2'-H), 3.86-3.80 (m, 2H, 5'-H); HRMS (FAB) m/z 353.1028 (M+H)$^+$ (C$_{13}$H$_{14}$FN$_6$O$_5$ requires 353.1010), 375.0848 (M+Na)$^+$ (C$_{13}$H$_{13}$FN$_6$NaO$_5$ requires 375.0829).

Example 7

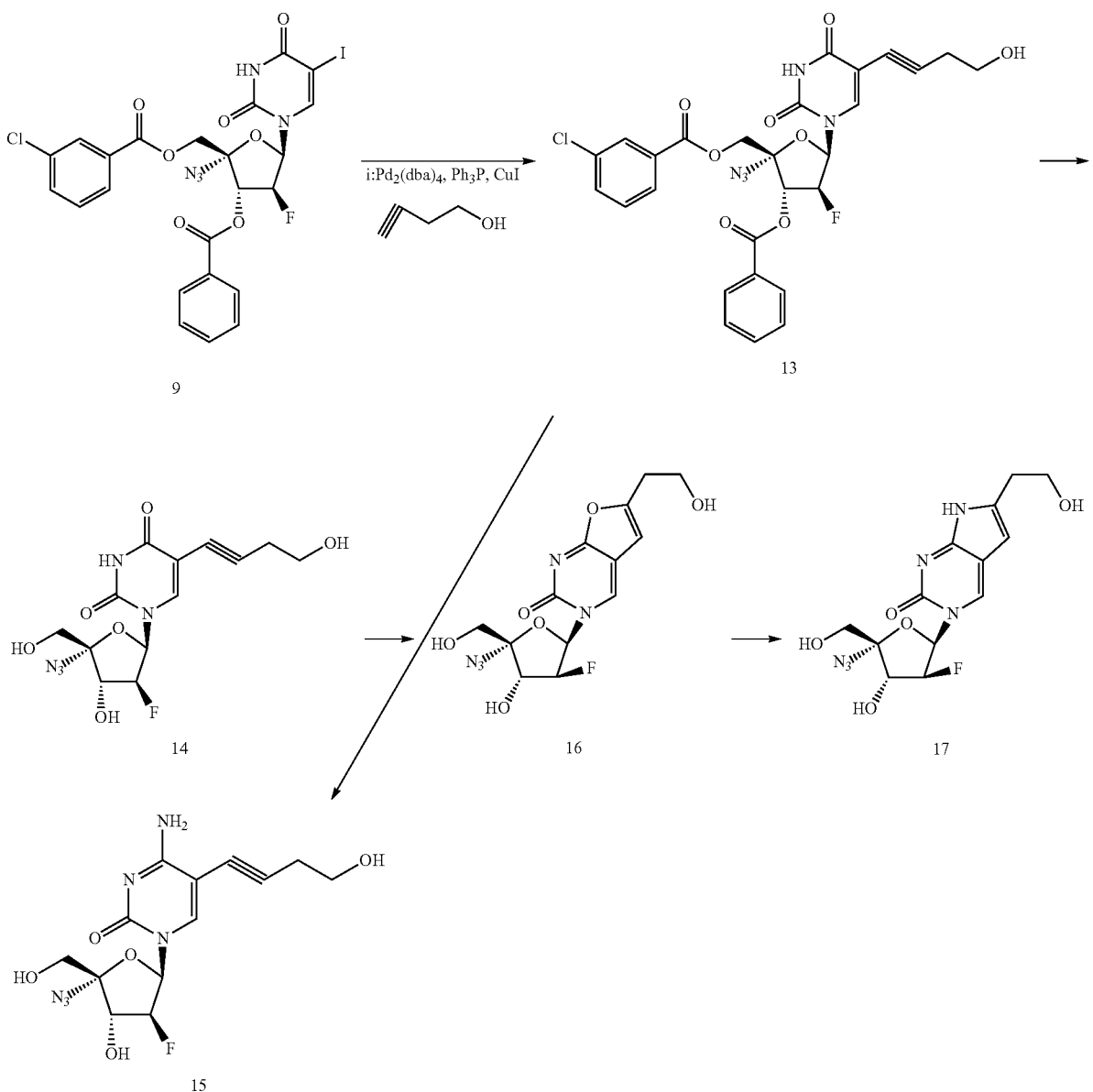

Scheme S.
Synthesis of 5-substituted and bicyclic pyrimidine nucleoside derivatives.

Synthesis of compound 13: Compound 9 (1.5 g, 2.29 mmol) dissolved DMF (anhydrous, 25 mL) is added successively with Et$_3$N (2.4 mL), 3-butyne-1-ol (0.33 g, 4.58 mmol), Pd$_2$(dba)$_4$ (46.8 mg), CuI (22.8 mg) and PPh$_3$ (0.228 g) to react at 35° C. under N2 protection for 30 h. The reaction mixture is evaporated and loaded on a column with dry method. Run the column with ethyl acetate: petroleum ether=1.5:1 (R$_f$=0.45, dichloromethane: methanol=25:1) to give compound 13 (474 mg, 0.79 mmol, yield: 34.59%); $^1$H NMR (300 MHz, CDCl$_3$) δ 8.72 (s, 1H, NH), 8.10-7.41 (m, 10H, Ar— and 6-H), 6.64-6.57 (dd, 1H, J$_1$=3.48 Hz, J$_2$=3.33 Hz, 1'-H), 5.83-5.77 (m, 1H, 3'-H), 5.53-5.30 (m, 1H, 2'-H), 4.99-4.79 (m, 2H, 5'-H), 3.80-3.76 (t, 2H, —CH$_2$CH$_2$OH), 2.66-2.62 (t, 2H, —CH$_2$CH$_2$OH); $^{13}$C NMR (75 MHz, CDCl$_3$) δ164.62, 161.31, 148.83, 141.94, 135.01, 134.89, 134.33, 133.80, 130.38, 130.16, 130.02, 128.49, 127.96, 127.65, 101.04, 95.60, 94.24, 92.83, 91.67, 84.10, 83.88, 72.31, 65.47, 60.69, 24.05; HRMS (FAB) m/z 620.0980 (M+Na)$^+$ (C$_{27}$H$_{21}$ClFN$_5$NaO$_8$ requires 620.0960).

Synthesis of compound 14: Compound 14 is synthesized under a condition similar to that of the synthesis for compound 11.

Synthesis of compound 15: Compound 15 is synthesized under a condition similar to that of the synthesis for compound 12.

Synthesis of compounds 16 and 17: Compound 14 is cyclized under different conditions to produce bicyclic compounds 16 and 17 (see the reference: Nucleosides, Nucleotides and Nucleic Acids, 2007, 26, 1083-1086).

Synthesis of compound 18: The solution of compound 9 (27.5 mg, 0.5 mmol) and 2-aminoethanol (305 mg, 5 mmol) in ethanol (5 mL) is heated at 60° C. for 24 h and is subjected to the solvent removal under reduced pressure. Then pyridine (12 mL) and acetic anhydride (1.663 mL, 1.53 g, 15 mmol) are added. The reaction mixture is stirred at room temperature for 5 h until the reaction is complete (TLC, R$_f$=0.55, petroleum ether:ethyl acetate=1:1). Then the mixture is extracted with dichloromethane for three times and washed with water. The organic phase is dried over anhydrous sodium sulfate, filtrated and azeotroped with toluene to remove the solvent under reduced pressure. The crude product is purified on a silica column (petroleum ether:ethyl acetate=4:1) to provide compound 18 (15 mg, 0.03178 mmol, yield 6.36%); $^1$H NMR (300 MHz, CDCl$_3$) δ 7.78 (br, 1H, 3-NH), 6.61 (s, 1H, 6-H), 6.57-6.49 (dd, J$_1$=3.58 Hz, J$_2$=3.6 Hz, 1H, 1'-H), 5.51-5.43 (dd, 1H, J$_1$=2.26 Hz, J$_2$=2.28 Hz, 3'-H), 5.38-5.19 (qq, 1H, 2'-H), 4.58-4.42 (m, 2H, 5'-H). 4.27-4.23 (t, 2H, 5-NHCH$_2$CH$_2$), 3.26-3.24 (t, 2H, 5-NHCH$_2$CH$_2$), 2.11 (br, 1H, 5-NH), 2.09 (s, 9H, CH$_3$); HRMS (FAB) m/z 472.14 (M+H)$^+$.

Compound 19 is synthesized with a method similar to the synthesis of compound 11.

Compound 20 is synthesized with a method similar to the synthesis of compound 12.

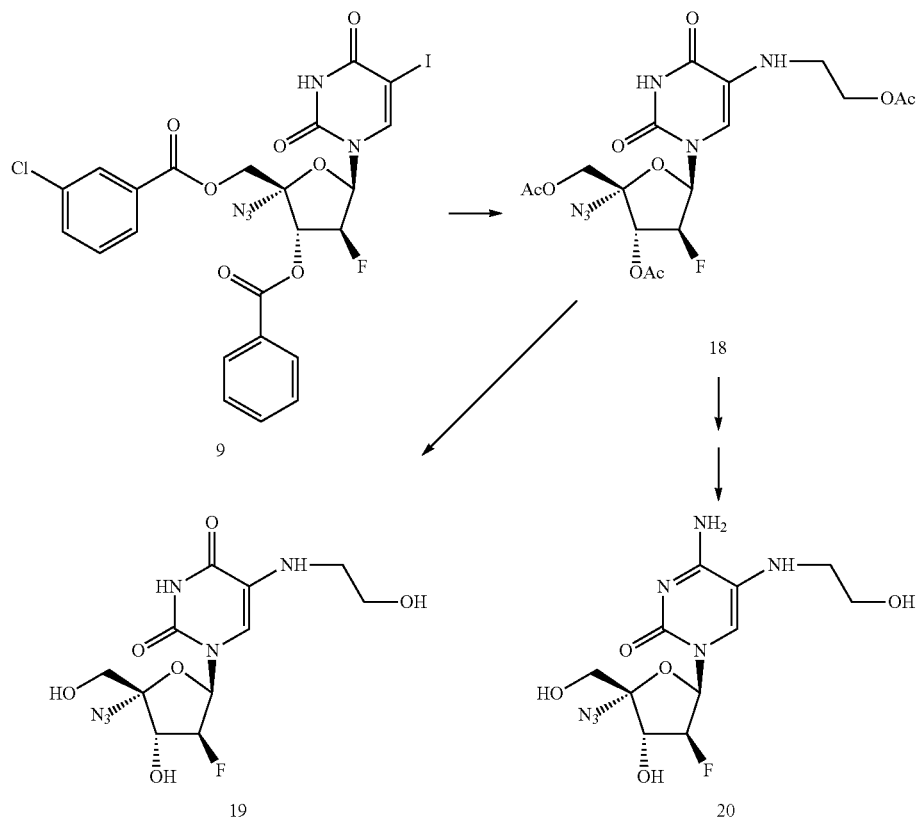

Scheme T.
Synthesis of a pyrimidine nucleoside derivative with amino substitution at position 5.

Example 9

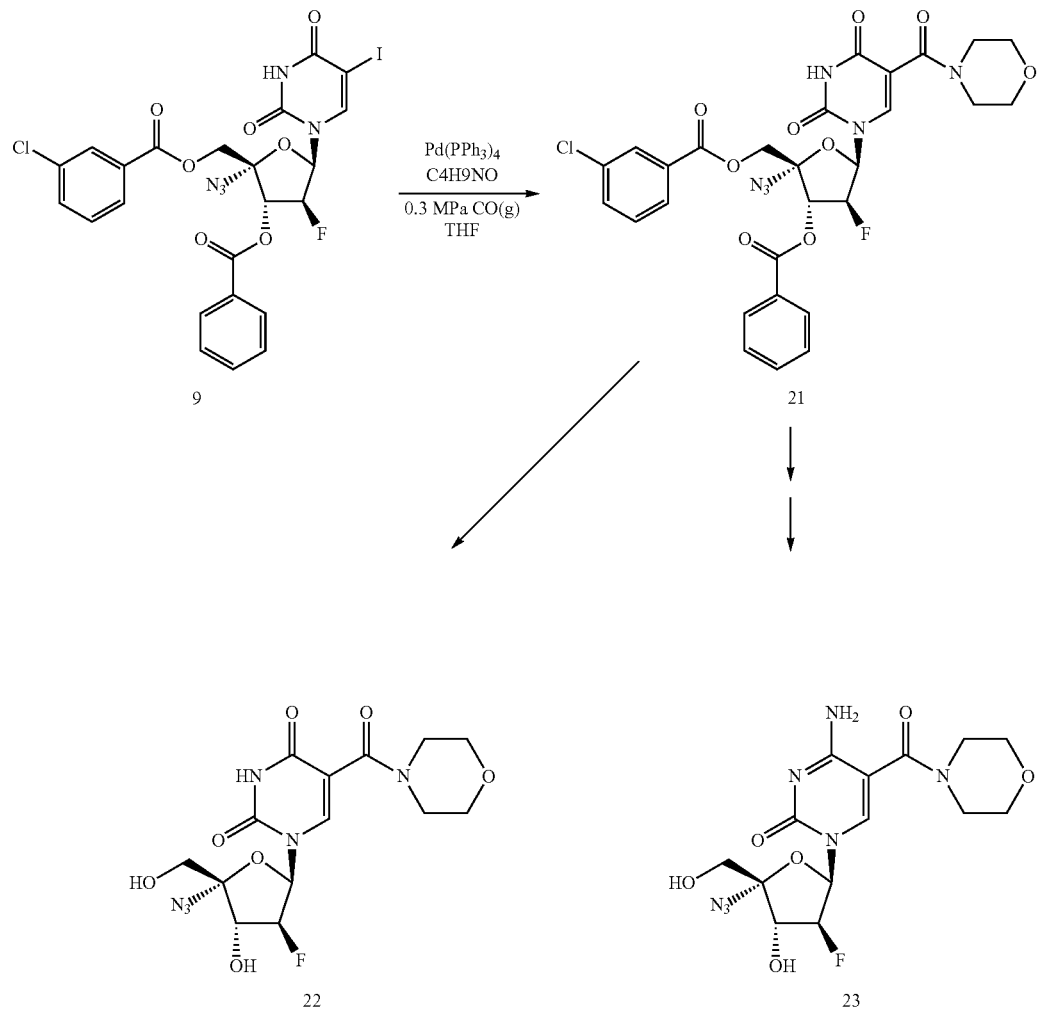

Scheme U.
Synthesis of a pyrimidine nucleoside derivative with amidation at position 5.

Synthesis of compound 21: The solution of compound 9 (0.2 g, 0.31 mmol) in THF (10 mL) is added with morpholin (0.27 g, 3.1 mmol) and Pd(PPh$_3$)$_4$ (0.04 g, 10% mol) under N$_2$ protection. The reaction mixture is allowed to react at 0.3 MPa CO (g) and 50° C. for 28 h, by when the reaction is substantially complete as indicated by TLC ($R_f$=0.2, ethyl acetate:petroleum ether=1:1). Then the mixture is filtered through celatom, the filtrate is concentrated and purified on a silica column (ethyl acetate:petroleum ether=3:1) to give Compound 21 (0.12 g, 59%).

Synthesis of compound 22: Compound 21 (77 mg) in NH$_3$/CH$_3$OH(20 ml) is stirred for 24 h under sealed conditions. After the complete consumption of the starting material as indicated by TLC ($R_f$=0.3, dichloromethane:methanol=10:1), the reaction mixture is purified on a silica column (dichloromethane:methanol=10:1) to give Compound 22 (30 mg, 63%). $^1$H NMR (300 MHz, CD$_3$OD) δ8.07 (s, 6-H), 6.50-6.45 (m, 1'-H), 5.36-5.14 (tt, 2'-H), 4.59-4.50 (dd, 1H, J$_1$=5.05 Hz, J$_2$=50.8 Hz, 3'-H), 3.85 (s, 2H, 5'-H), 3.69-3.30 (m, 8H, Morpholine-H); HRMS (FAB) m/z 400.114 (M+H)$^+$ (C$_4$H$_{17}$FN$_6$O$_7$, calculated 401.121).

Compound 23 is synthesized with a method similar to the synthesis of compound 12.

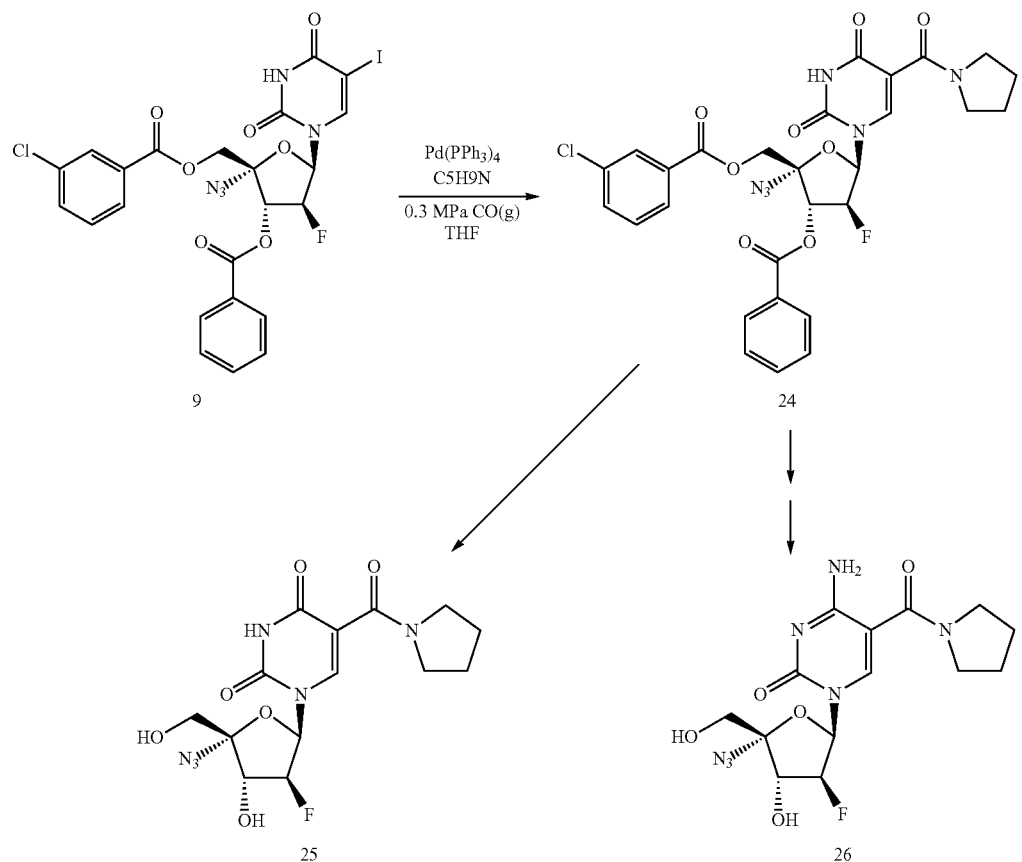

Scheme V.
Synthesis of a pyrimidine nucleoside derivative with amidation at position 5.

Synthesis of compound 24: The solution of compound 9 (0.5 g, 0.76 mmol) in THF (20 mL) is added with pyrrolidine (0.54 g, 7.6 mmol) and Pd(PPh$_3$)$_4$ (0.09 g, 10% mol) under N$_2$ protection. The reaction mixture is allowed to react at 0.4 MPa CO (g) and 50° C. with stirring for 28 h, by when the reaction is substantially complete as indicated by TLC (R$_f$=0.2, ethyl acetate:petroleum ether=1:1). Then the mixture is filtered through celatom, the filtrate is concentrated and the crude product is purified with column chromatography (ethyl acetate:petroleum ether=3:1) to give Compound 24 (0.21 g, 44%). $^1$H NMR (300 MHz, CDCl$_3$) δ 10.66 (brs, 1H, NH), 8.29 (s, 6-H), 8.07-7.36 (m, 9H, Ar), 6.64 (m, 1H, 1'-H), 5.89 (m, 1H, 3'-H), 5.52 (m, 1H, 2'-H), 4.97-4.80 (m, 2H, 5'-H), 3.45-3.45 (m, 4H, Pyrrolidine-H), 1.92-1.90 (m, 4H, Pyrrolidine-H); HRMS (FAB) m/z 626.133 (M+H)$^+$ (C$_{28}$H$_{24}$FN$_6$O$_6$, 627.145).

Compounds 25 and 26 are synthesized with methods similar to the synthesis of compounds 11 and 12.

Compound 27 is synthesized following the synthesis method and procedure for compound 22 by reacting compound 9 with thiomorpholine followed by a deprotection of the hydroxy group.

Compounds synthesized in the present invention as an active ingredient useful for anti-tumor and anti-virus medicaments can be used alone or in combination with other anti-tumor/anti-virus medicament. The combination therapy indicated in the invention comprises the employment of at least one of the compounds of the invention and the derivatives thereof with one or more other anti-tumor/anti-virus medicaments in order to enhance the overall efficacy. The dosing amount and drug administration time in a combination therapy are determined by the most reasonable therapeutic effect achievable under a specific condition.

The compatible medicament covered by the invention comprises an effective dosage of compounds of general formulae (1)-(6). The compatible medicament can comprise an effective anti-tumor/anti-virus chemical component and pharmaceutical formulation. The "effective dosage" used herein refers to the amount of the compound needed to provide a therapeutic effect in the subject being treated. The effective dosage or dosage may vary according to the suggestions of one experienced made in different situations. For example, the dosage can change if the type of the tumor and virus being treated is different, or the administration method is different, or if other treatment such as other anti-tumor or anti-virus medicament is involved etc. The concerted application of medicament can be prepared into any available dosage forms. If some of them have a basic or acidic compound that can form non-toxic acid or salt, then the salt form of the compound can be used. Pharmaceutically acceptable organic salts include physiologically acceptable anion salts such as p-toluenesulfonate, methanesulfonate, acetate, benzoate, citrate, tartrate, maleate, succinate, ascorbate, glycerophosphate and the like. The useful inorganic salts include chloride, bromide, fluoride, iodide, sulfate, nitrate, bicarbonate, carbonate, phosphate and the like. Said salt form can be formed by a basic compound such an amine with a proper acid. And carboxylic acids can from useful salts with an alkali or alkaline earth metal.

In general, compounds encompassed in general formulae (1)-(6) in the invention are soluble in organic solvent, water-soluble solvent and mixed solvent of organic solvent and water-soluble solvent with water. Water-soluble solvent is preferably alcohols, poly (ethylene glycol), N-methyl-2-pyrrolinone, N,N-dimethylacetamide, N,N-dimethylformamide, dimethylsulfoxide, acetonitrile and the combination thereof. The alcohol is preferably methanol, ethanol, isopropanol, glycerol or ethylene glycol. Compounds of the invention can be mixed with common carriers to form a formulation. A formulation prepared by dissolving the compound into water-soluble organic solvent, aprotic solvent, water-soluble lipid, cyclodextrin, fatty acid, phospholipid or a mixed solvent thereof to afford a medicament solution and adding physiological saline or 1-20% carbohydrate such as an aqueous solution of glucose to the medicament solution, is stable and used in animals and clinical applications.

The medicament product prepared using a compound of formulae (1)-(6) as the active ingredient can be administrated orally or parenterally, or otherwise though an implantable drug pump and other methods. The parenteral administration herein refers to injections or infusions conducted subcutaneously, intradermally, intramuscularly, intravenously, intraarterially, intraatrially, intrasynovially, intrasternally, intrathecally, intracranially or in a wound site. The desired medicament formulation can be prepared through mixing at a certain ratio commonly known in the field by an artisan, and can be in a dosage form of tablet, capsule, emulsion, powder, injection for intravenous administration, infusion solution, lyophilized powder, pill, emulsion suspension, aqueous suspension, aqueous solution, colloid, colloidal solution, sustained release formulation, nano-preparation or other forms, useful for animals or clinical applications.

The compound of formulae (1)-(6) can be used in the preparation of anti-cancer medicaments for the treatment or alleviation of cancers of a certain tissue or organ. The cancers include but are not limited to colon cancer, liver cancer, lymphoma, lung cancer, esophageal cancer, breast cancer, central nervous system tumor, melanoma, ovarian cancer, kidney cancer, leukemia, prostate cancer, pancreatic cancer, and the like.

The compound of formulae (1)-(6) can be used in the preparation medicaments for the treatment or prevention or alleviation of viral diseases caused by some kind of virus. The viruses include but are not limited to hepatitis B virus (HBV), hepatitis C virus (HVC), human immunodeficiency virus (HIV), yellow fever virus (YFV), respiratory syncytial virus (RSV), herpes simplex virus (HSV), bovine viral diarrhea virus (BVDV), hepatitis G virus (HGV), GB virus-B (GBV-B), dengue virus (Dengue), human rhinovirus (HRV), polio virus (Poliovirus), varicella-zoster virus (VZV), Epstein-Barr virus (EBV), cytomegalovirus (CMV), and the like.

Anti-Virus and Anti-Tumor Activity

Compounds encompassed by the invention have anti-virus and anti-tumor activities, said anti-virus including anti-HIV-1, anti-HBV and anti-HCV. Some of the examples are listed below for the purpose of illustration.

1. Determination of the Activity Against HIV-1 Replication:

The effect of the compounds encompassed by the invention on HIV-1 replication was determined. The example compounds of the invention and 293T cells (obtained from ATCC) were incubated for 15 min then added with VSVG/HIV-luc (NL4-3) virus strain and cultivated at 37° C. for 48h. The degree of infection of HIV-1 was determined using luciferase as the reporter gene and Zidovudine (AZT) (Xiamen Mike Pharmaceutical Co., Ltd.) as the positive control.

Culture medium: DMEM medium (Gibco Co., USA), RPMI-1640, FBS; preparation method: RPMI-1640/DMEM+10% FBS. Experimental medium: dimethylsulfoxide (Sigma, USA).

Experimental Methods

1. Preparation of test samples and control samples: test samples were weighed and dissolved in DMSO, concentration of stock solution: 10 mmol/L; control samples: Zidovudine was weighed and dissolved in DMSO, concentration of stock solution: 10 mmol/L.

2. Procedures 2.1 Preparation of wild-type HIV-1 recombinant pseudovirus: 293ET cells were inoculated to a 100 mm culture dish with a density of $2.2 \times 10^6$ cells one day before co-transfection with VSV-G plasmid (3 μg) and wild-type HIV-1 core gene (8 μg) using the modified calcium phosphate precipitation method. Sixteen hours after transfection, the cells were rinsed with PBS and changed into a fresh medium to continue cultivating for 32 h. The supernatant was collected and filtered through a 0.45 μm membrane to provide the wild-type HIV-1 recombinant virion VSVG/HIV-WT.

2.2 Determination of the p24 antigen of HIV-1 recombinant pseudo virus: The wild-type virus stock solution was diluted into a series of virus solutions with different dilution ratios. 450 μL of each solution was taken to mix with 50 μL lysis buffer. The concentration of p24 antigen in the wild-type recombinant virus stock solution was determined and calculated according to the instructions of the ELISA kit for p24 antigen (ZeptoMetrix, Cat: 0801111).

2.3 Test of the inhibition of HIV-1 by the medicament: 293T cells were seeded to a 24-well plate at a density of $6 \times 10^4$ cells/well one day before the infection. The test compound was dissolved in DMSO and added to the cell cultures 15 min before the infection. Solvent DMSO was used as the blank control. To infect, 0.5 mL virus solution (the virus stock was diluted according to p24 concentration thereof to 0.1-0.5 ng p24/ml) was added. Forty-eight hours later, the supernatant was removed and 50 μL cell lysis buffer (Promega) was added to each well. Further, 20 μL cell lysate was added to 30 μL luciferase substrate (Promega). The relative activity of luciferase was determined with a FB15 fluorescence detector (Sirius) apparatus. The half inhibitory concentration of the compound on wild-type HIV-1 replication was calculated using DMSO as a blank control.

2.4 MTS method for the test of effects of the compound on cell survival: 293T cells in logarithmic growth phase were seeded to a 96-well plate at 8000-10000 cells/well, 100 μL per well and cultivated in an incubator at 37° C. with 5% $CO_2$ for 24 h, then added with the test compound and DMSO as the blank control (final concentration 0.1%) and continuously cultivated in the incubator at 37° C. with 5% $CO_2$ for 44 h. Then, 20 μL freshly prepared mixture of MTS/PMS was added to each well and after 4 h incubation in the incubator at 37° C. with 5% $CO_2$, the color was developed. The light absorption (OD) of each well at wavelengths 490 nm and 650 nm (background) was detected on an enzyme linked immuno analyzer, and the survival rate of cells was calculated.

The activity against HIV-1 ($EC_{50}$) and cytotoxicity ($CC_{50}$) determined are listed in the following table.

| ID | | EC$_{50}$ (μM) VSVG/HIV-luc (NL4-3) | CC$_{50}$ (μM) (293T) |
|---|---|---|---|
| 5-02 | (structure) | 0.093 ± 0.067 | ≥25 |
| 5-03 | (structure) | 5.7 ± 0.2 | ≥25 |
| 5-09 | (structure) | 0.7 ± 0.1 | ≥25 |
| 5-11 | (structure) | 5.2 ± 0.3 | ≥25 |

-continued
| ID | | EC$_{50}$ (μM) VSVG/HIV-luc (NL4-3) | CC$_{50}$ (μM) (293T) |
|---|---|---|---|
| 5-15 | 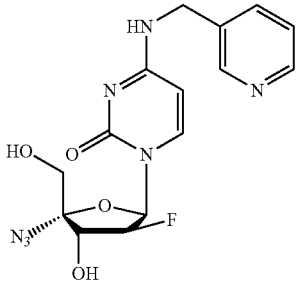 | 1.3 ± 0.1 | ≥25 |
| 5-17 | 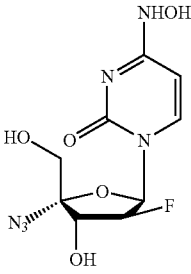 | 0.7 ± 0.2 | ≥25 |
| 5-19 | 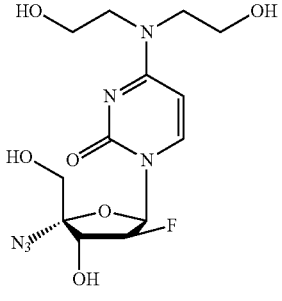 | 0.8 ± 0.7 | ≥25 |
| 5-20 | 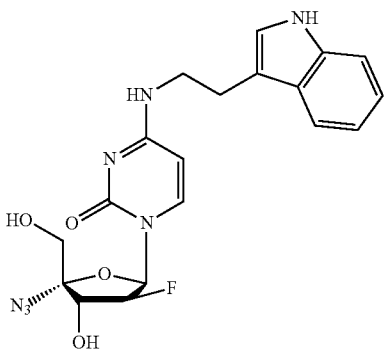 | 5.8 ± 2.6 | ≥25 |
| 5-21 | 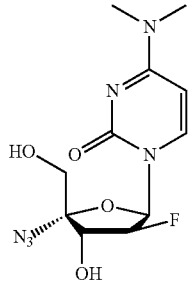 | 13 ± 6 | ≥25 |

-continued

| ID | | EC$_{50}$ (μM) VSVG/HIV-luc (NL4-3) | CC$_{50}$ (μM) (293T) |
|---|---|---|---|
| 5-28 | [structure: cytidine analog with NHCH$_3$ at C4, 2'-F, 4'-N$_3$, 3'-OH, 5'-CH$_2$OH] | 6.7 ± 4.7 | ≥25 |
| 8a | [structure: N4-(carboxymethyl)amino cytidine analog with 2'-F, 4'-N$_3$, 3'-OH, 5'-CH$_2$OH] | 5.1 ± 1.1 | ≥25 |
| 8d | [structure: N4-tryptophan-conjugated cytidine analog with 2'-F, 4'-N$_3$, 3'-OH, 5'-CH$_2$OH] | 0.7 ± 0.1 | ≥25 |
| 8e | [structure: N4-(dimethyl aspartate)-conjugated cytidine analog with 2'-F, 4'-N$_3$, 3'-OH, 5'-CH$_2$OH] | 12 ± 2.8 | ≥25 |

-continued

| ID | | EC$_{50}$ (μM) VSVG/HIV-luc (NL4-3) | CC$_{50}$ (μM) (293T) |
|---|---|---|---|
| 8f | (structure) | 4.7 ± 0.1 | ≥25 |
| 8h | (structure) | 6.2 ± 0.6 | ≥25 |
| 8g | (structure) | 8.1 ± 5.5 | ≥25 |
| 8m | (structure) | 0.5 ± 0.3 | ≥25 |

-continued

| ID | | EC$_{50}$ (μM) VSVG/HIV-luc (NL4-3) | CC$_{50}$ (μM) (293T) |
|---|---|---|---|
| 8n | [structure] | 5.4 ± 3.0 | ≥25 |
| 7b | [structure] | 0.7 ± 0.1 | ≥25 |
| 7c | [structure] | 0.5 ± 0 | ≥25 |
| 7j | [structure] | 10 ± 7 | ≥25 |

-continued
| ID | | EC$_{50}$ (μM) VSVG/HIV-luc (NL4-3) | CC$_{50}$ (μM) (293T) |
|---|---|---|---|
| 7m | 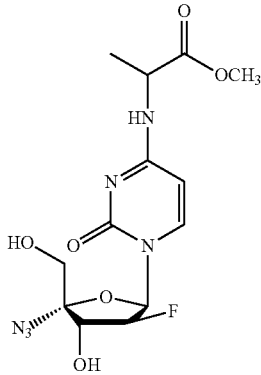 | 10 ± 6.6 | ≥25 |
| Zidovudine | AZT | 0.084 ± 0.0026 | |
| | | Inhibitory activity at 10 μM |
|---|---|---|
| 10 | 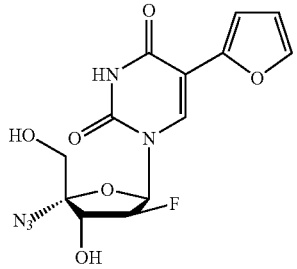 | 15.1 ± 0.8 |
| 12 | 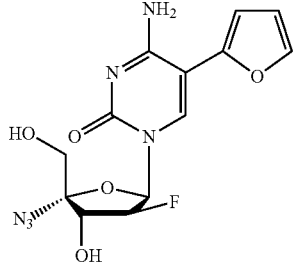 | 15.8 ± 4.4 |
| 14 | 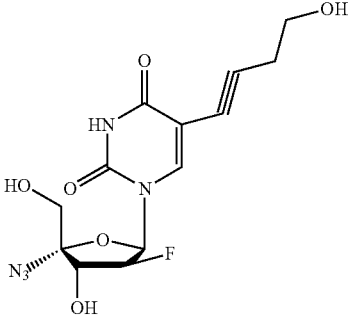 | 10.0 ± 5.9 |

| ID | EC$_{50}$ (μM) VSVG/HIV-luc (NL4-3) | CC$_{50}$ (μM) (293T) |
|---|---|---|
| 15 | 27.0 ± 4.7 | |
| 16 | 9.9 ± 0.8 | |
| 22 | 0 ± 8.2 | |
| 25 | 16.8 ± 1.2 | |
| 27 | 4.8 ± 1.8 | |

-continued
| ID | | EC$_{50}$ (μM) VSVG/HIV-luc (NL4-3) | CC$_{50}$ (μM) (293T) |
|---|---|---|---|
| 5-01 | 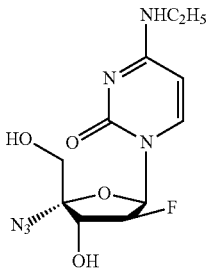 | 21.6 ± 1.3 | |
| 5-04 | 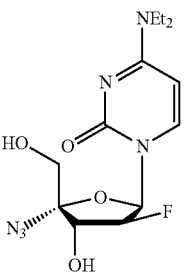 | 8.6 ± 7.5 | |
| 5-05 | 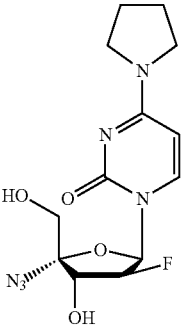 | 31.6 ± 3.6 | |
| 5-06 | 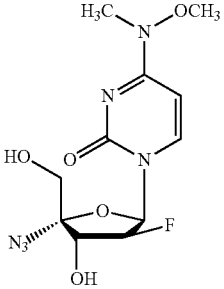 | 32.2 ± 10.5 | |
| 5-07 | 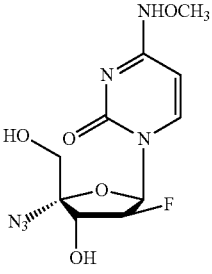 | 29.4 ± 5.1 | |

-continued

| ID | | EC$_{50}$ (μM) VSVG/HIV-luc (NL4-3) | CC$_{50}$ (μM) (293T) |
|---|---|---|---|
| 5-08 | [structure: cytidine analog with NHOEt at C4 of pyrimidine, 3'-azido, 2'-fluoro ribose] | 15.6 ± 1.3 | |
| 5-10 | [structure: cytidine analog with N-cyclohexylamino at C4, 3'-azido, 2'-fluoro ribose] | 1.9 ± 2.2 | |
| 5-12 | [structure: cytidine analog with morpholino at C4, 3'-azido, 2'-fluoro ribose] | 3.0 ± 6.9 | |
| 5-13 | [structure: cytidine analog with NH-CH$_2$CH$_2$OH at C4, 3'-azido, 2'-fluoro ribose] | 41.7 ± 1.8 | |

-continued

| ID | | EC$_{50}$ (μM) VSVG/HIV-luc (NL4-3) | CC$_{50}$ (μM) (293T) |
|---|---|---|---|
| 5-14 | *[structure]* | 6.3 ± 3.2 | |
| 5-16 | *[structure]* | 31.3 ± 4.0 | |
| 5-18 | *[structure]* | 17.8 ± 0.6 | |
| 5-22 | *[structure]* | 14.2 ± 5.1 | |
| 5-23 | *[structure]* | 10.4 ± 3.5 | |

-continued

| ID | structure | EC$_{50}$ (μM) VSVG/HIV-luc (NL4-3) | CC$_{50}$ (μM) (293T) |
|---|---|---|---|
| 5-24 | | 33.8 ± 1.0 | |
| 5-25 | | 35.0 ± 1.7 | |
| 5-26 | | 33.9 ± 0.5 | |
| 5-27 | | 32.3 ± 3.2 | |
| 5-29 | | 11.6 ± 0.5 | |

| ID | | EC$_{50}$ (μM) VSVG/HIV-luc (NL4-3) | CC$_{50}$ (μM) (293T) |
|---|---|---|---|
| 5-30 | (structure) | 38.6 ± 5.7 | |
| 5-31 | (structure) | 22.8 ± 3.5 | |
| 5-32 | (structure) | 0.9 ± 0.8 | |
| 5-33 | (structure) | 14.1 ± 2.2 | |
| 7c | (structure) | 38.8 ± 3.3 | |

| ID | Structure | EC$_{50}$ (μM) VSVG/HIV-luc (NL4-3) | CC$_{50}$ (μM) (293T) |
|---|---|---|---|
| 7L | (structure: pyrrolidine-COOCH$_3$ substituted cytidine analog with N$_3$, F, OH) | 5.1 ± 4.6 | |

2. In Vitro Biological Activity Test Against Hepatitis B Virus (HBV)

2.1 Cell Recovery and Culturing

A tube of frozen HepG2.2.15 cells taken from a liquid nitrogen tank was quickly placed into a water bath at 42° C. and shaken to thaw. DMEM complete medium (fetal bovine serum 10%, G418 380 μg/mL, Penicillin 100 U/ml, Streptomycin 100 U/ml) was used for cell culturing at conditions of 37° C. and 5% CO$_2$. The number of cell passage in normal growing cells was once per 2-3 days.

2.2 MTT Method for the Test of Cytotoxicity of the Compound on HepG2.2.15 Cells Cytotoxicity of the compound on HepG2.2.15 cells was tested with the MTT colorimetric assay established by Mosmann. After continuous incubation for 72 h, 10 μL MTT was added to each well. Four hours later, the supernatant was discarded and 200 μL DMSO was added to each well. The OD value in each well was read using a microplate reader (measurement wavelength 490 nm, reference wavelength 630 nm). The result was recorded and the percentage inhibition of HepG2.2.15 cells by each compound was calculated:

$$\text{Percentage inhibition} = \frac{OD_{blankcontrol} - OD_{medicament}}{OD_{blankcontrol}} \times 100\%$$

The half toxic concentration (TC$_{50}$) of the medicament on cells was calculated according to the percentage inhibition of the cell by the medicament.

2.3 In Vitro Inhibition of HBV by the Compound

The effect of a compound on HBV surface antigen s and antigen e in the cell culture was detected using a screening concentration lower than the half toxic concentration of the compound. HepG2.2.15 cells in logarithmic growth phase were selected and digested with trypsin into single cell suspension, and were seeded to a 24-well plate at a concentration of 2×10$^4$/mL, 1 mL per well. Media of different medicament concentrations were added, three wells for each concentration, and cells added with complete medium were set as normal control. Cell supernatants and cells at day 3, day 6 and day 9 were collected and kept under −20° C. The intracellular and extracellular expressions of e antigen and surface antigen at day 3, day 6 and day 9 were determined by ELISA.

2.4 Effect of the Compound on HBeAg and HBsAg in HepG2.2.15 Cell Supernatant Detected by ELISA The instructions of the kit were followed;

Measurement: OD value of each well was read from microplate reader using dual wavelength 450/630 nm.

Result determination: The Cutoff value was first calculated according to equation: COV=average OD of negative control×2.1. Then, if a sample had OD≥COV, the result was determined as positive, or if a sample had OD≤COV, the result was determined as negative.

| Compounds entry | Structure | IC$_{50}$ (μM) (HBsAg) | IC$_{50}$ (μM) (HBeAg) | CC$_{50}$ (μM) (HepG2. 2. 15) |
|---|---|---|---|---|
| 5-02 | (structure: cytidine analog with HN-CH$_2$CH$_2$-NH$_2$, N$_3$, F, OH) | 8.05 | — | ≥25 |

-continued

| Compounds entry | Structure | IC$_{50}$ (μM) (HBsAg) | IC$_{50}$ (μM) (HBeAg) | CC$_{50}$ (μM) (HepG2.2.15) |
|---|---|---|---|---|
| 5-03 | 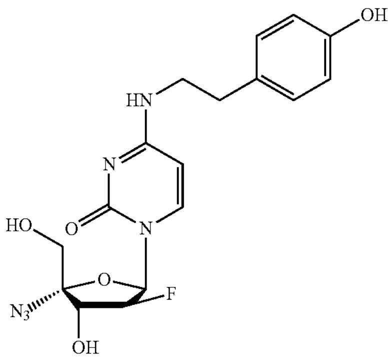 | <0.1 | — | 833.88 |
| 5-07 | 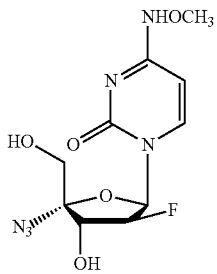 | <0.01 | >1.0 | 417.83 |
| 5-08 | 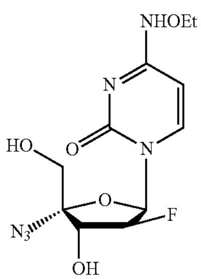 | 0.12 | >1.0 | 572.43 |
| 5-09 | 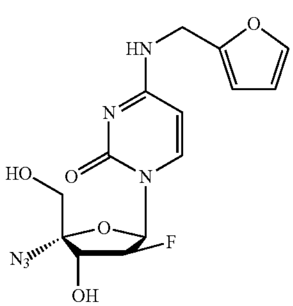 | 0.19 | — | ≥25 |
| 5-10 | 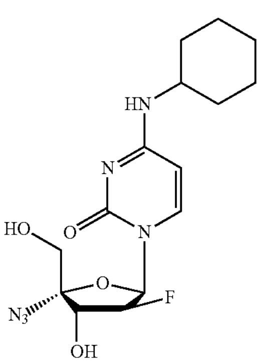 | <0.1 | — | 653.86 |

-continued
| Compounds entry | Structure | $IC_{50}$ (μM) (HBsAg) | $IC_{50}$ (μM) (HBeAg) | $CC_{50}$ (μM) (HepG2.2.15) |
|---|---|---|---|---|
| 5-11 | 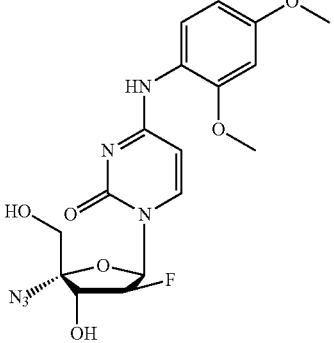 | 0.06 | — | 722.29 |
| 5-12 | 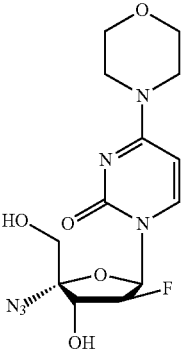 | <0.1 | >1 | 699.83 |
| 5-14 | 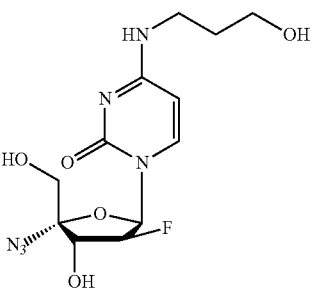 | 2.46 | — | 668.43 |
| 5-15 | 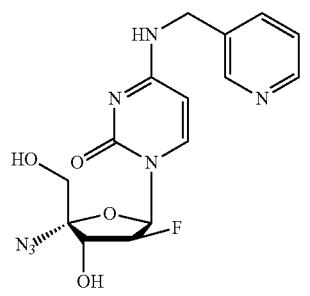 | 0.09 | 0.16 | ≥25 |
| 5-17 | 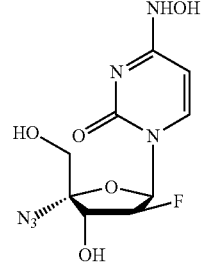 | 0.07 | 0.11 | 950.53 |

-continued

| Compounds entry | Structure | IC$_{50}$ (μM) (HBsAg) | IC$_{50}$ (μM) (HBeAg) | CC$_{50}$ (μM) (HepG2.2.15) |
|---|---|---|---|---|
| 5-19 | 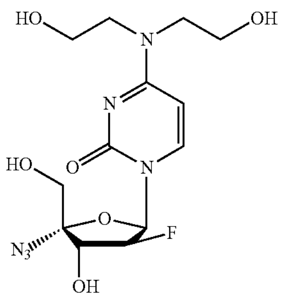 | 0.009 | — | >1250 |
| 5-20 | 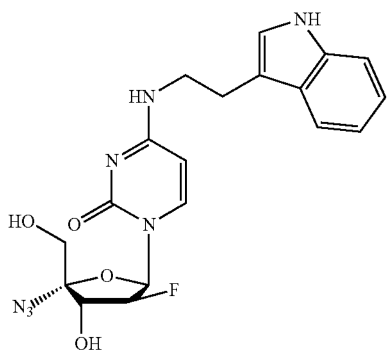 | — | — | >250 |
| 5-21 | 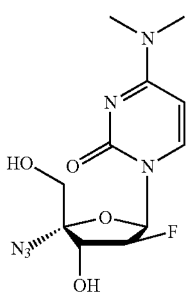 | — | 15.52 | >250 |
| 5-28 | 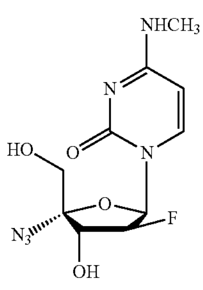 | 6.26 | 14.29 | >250 |
| 7b | 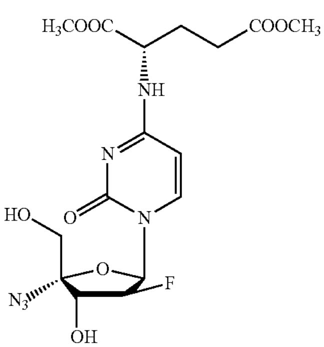 | 0.02 | 6.16 | >1250 |

-continued

| Compounds entry | Structure | IC$_{50}$ (μM) (HBsAg) | IC$_{50}$ (μM) (HBeAg) | CC$_{50}$ (μM) (HepG2.2.15) |
|---|---|---|---|---|
| 7c | 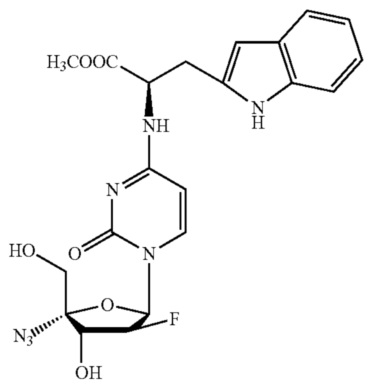 | 0.20 | 0.32 | ≥280 |
| 7j | 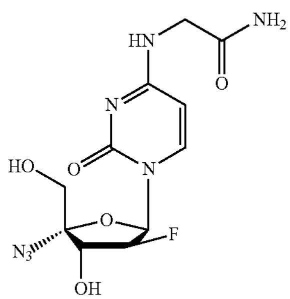 | — | 6.16 | 239.31 |
| 7L | 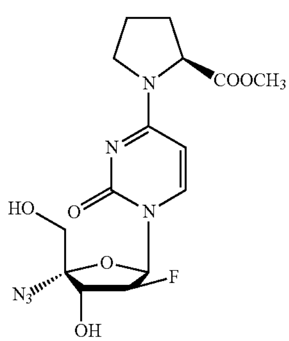 | 0.02 | — | 596.14 |
| 7m | 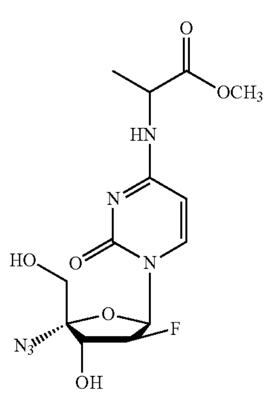 | 1.89 | 21.24 | 311.02 |

-continued

| Compounds entry | Structure | IC$_{50}$ (μM) (HBsAg) | IC$_{50}$ (μM) (HBeAg) | CC$_{50}$ (μM) (HepG2.2.15) |
|---|---|---|---|---|
| 8a | 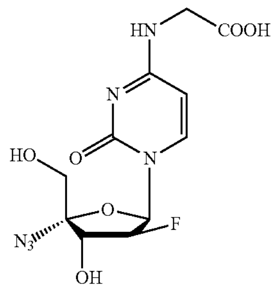 | 13.81 | 16.67 | >250 |
| 8d | 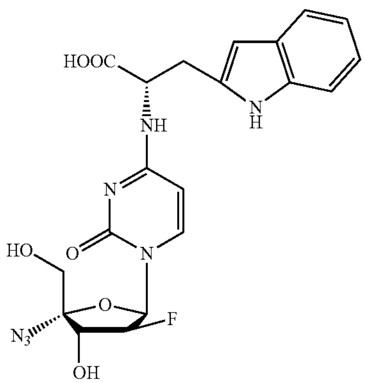 | 0.03 | 0.36 | ≥25 |
| 8e | 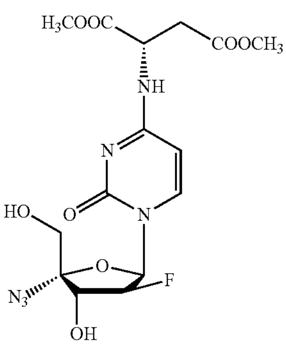 | 20.53 | 12.84 | 231.20 |
| 8f | 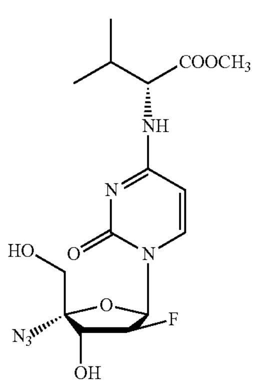 | 0.26 | — | >250 |

-continued

| Compounds entry | Structure | IC$_{50}$ (μM) (HBsAg) | IC$_{50}$ (μM) (HBeAg) | CC$_{50}$ (μM) (HepG2.2.15) |
| --- | --- | --- | --- | --- |
| 8g | (methionine methyl ester conjugated to cytosine nucleoside with 3'-azido, 2'-fluoro, 3'-OH) | 19.61 | — | >250 |
| 8h | (serine methyl ester conjugated to cytosine nucleoside with 3'-azido, 2'-fluoro, 3'-OH) | 0.07 | — | >250 |
| 8n | (phenylalanine methyl ester conjugated to cytosine nucleoside with 3'-azido, 2'-fluoro, 3'-OH) | — | 4.41 | >250 |
| 22 | (5-morpholinocarbonyl uracil nucleoside with 3'-azido, 2'-fluoro, 3'-OH) | 2.14 | — | 643.57 |
| 27 | (5-thiomorpholinocarbonyl uracil nucleoside with 3'-azido, 2'-fluoro, 3'-OH) | <0.10 | — | 584.57 |

3. Activities Against Hepatitis C Virus (HCV)

Compounds encompassed by the invention have anti-HCV effects. Experiments for in vitro anti-HCV activities were performed as follows:

3.1 Cell Culturing

HCV replication cells (Avva.5) were cultivated in Dulbecco's modified Eagle medium containing 10% fetal calf serum and 1 mg/mL G418. 293-Sip-L cells were cultivated in Dulbecco's modified Eagle medium containing 10% fetal calf serum, 250 μg/mL G418 and 150 μg/mL hygromycin B.

3.2 HCV Infection Determination (RT-PCR Method)

Cells in a Φ60 mm Petri dish were incubated in positive medium containing 100 μL HCV for 12 h, then in fresh medium free of HCV that was replaced every day. When being tested for HCV-RNA seven days after the infection, cells were trypsinized and washed with Dulbecco's modified Eagle medium twice through a centrifugation method. The upper layer from the second wash (as a control) and the washed cells were collected in pairs and used for RNA extraction and RT-PCR test. The β-actin mRNA was determined simultaneously as a control.

3.3 Quantitative Determination of HCV-RNA

The quantitative determination of HCV-RNA was performed using automatic PCR enzyme-linked immunoassay (version 2.0, Roche Diagnostics, Branchburg, N.J.).

Compound 5-02 exhibited inhibitory effect at concentrations 6, 0.6 and 0.06 μg/mL (see the table below). The levels of HCV-RNA were determined using automatic PCR enzyme-linked immunoassay.

| | Concentration of compound 5-02 in the culture | | | |
|---|---|---|---|---|
| | 0 μg/mL | 0.06 μg/mL | 0.6 μg/mL | 6 μg/mL |
| Exp 1 | $5.3 \times 10^2$ | $4.5 \times 10^2$ | $0.90 \times 10^2$ | $1.0 \times 10^2$ |
| Exp 2 | $4.0 \times 10^2$ | $4.2 \times 10^2$ | $0.70 \times 10^2$ | $0.80 \times 10^2$ |

4. Anti-Tumor Activity 4.1 Cell and Cell Culturing

Cell culturing: Raji cells in RPMI1640 culture solution containing 10% fetal calf serum were incubated in an incubator at 37° C. with 5% $CO_2$ for 2-3 days. Cells in logarithmic growth phase were used for the experiment.

4.2 Inhibition Rate of Cell Growth Detected by Thiazolyl Blue Tetrazolium Bromide (MTT) Reduction Cells in logarithmic growth phase were taken and after the cell density was adjusted to $5 \times 10^4$ cells/mL, they were seeded to three 96-well plates separately, 100 μL per well. The culture solution was replaced after 24 h cell culturing. The experimental group was added with 0.3, 1.5, 3, 6, 12, 24 μmol/L N—Cu separately, 200 μL per well and one medicament concentration per group. The blank group (for zeroing) was only added with RPMI1640 culture solution containing 10% fetal calf serum and no cell was added. The control group was added with an equal volume of RPMI1640 culture solution containing 10% fetal calf serum. Each group had 5 replicates. After cells were incubated for 24 h, 48 h and 72 h separately, 20 μL MTT solution (5 mg/mL) was added to each well followed by a 4 h incubation. The supernatant was removed by sucking it out and discarded. 150 μL DMSO was added per well, vortexed about 5 min to mix evenly. After the crystal was completely dissolved, the absorption (A) value at 570 nm of each well was tested within 20 min on enzyme-linked immuno analyzer. The experiment was repeated 3 times and the average was taken to calculate the inhibition rate of cell growth by the following equation.

Inhibition rate of cell growth=(1−average $A$ value of experimental group/average $A$ value of control group)×100%

Compounds encompassed by the invention exhibited anti-tumor effects. Inhibitory effects of typical compounds on human lymphoma Raji cells are shown below:

| Compound entry | Structure | Inhibitory activity, $IC_{50}$ (μM) |
|---|---|---|
| 5-02 | 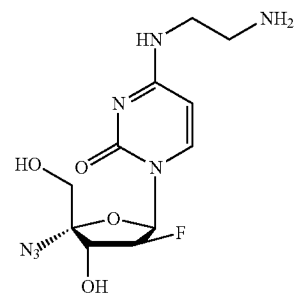 | 45.0 |
| 5-15 | 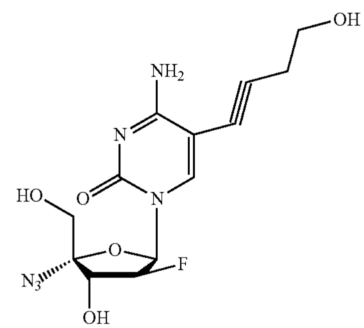 | 0.20 |
| 5-19 | 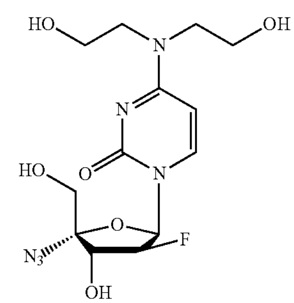 | 1.60 |
| 7b | 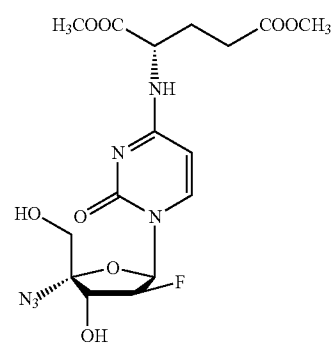 | 28.0 |

The invention claimed is:

1. A compound having the following structure:

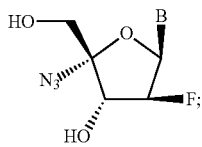

or a pharmaceutically acceptable salt thereof, wherein B is

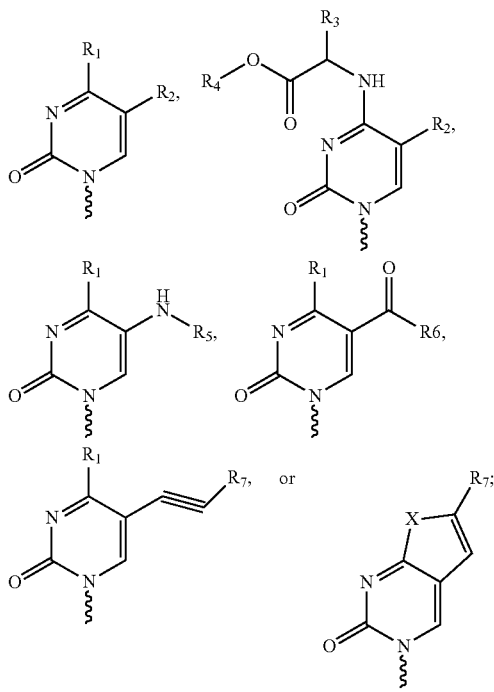

$R_1$ is selected from OH, NHOH, NHOCH$_3$, NHOEt, NHOR, NROH, NROR, NHR, NRR, NH(CH$_2$)$_n$OH, NH(CH$_2$)$_n$OR, NHCH$_2$Ar, NHCH$_2$-Het, CN, COOH, CONH$_2$, COOR, CSNH$_2$, C(=NH)NH$_2$, C(=NH)OR, C(=NH)OH, NHNH$_2$, NHNHR, NRNH$_2$, NRNHR, NRNRR, NHNHC(=O)NH$_2$, NHNHC(=S)NH$_2$, NHNHC(=O)NHR, NHNHC(=S)NR, NHC(=O)NHR, NHC(=S)NHR, NHCH$_2$CONH$_2$, NHCH$_2$CONHR;

alternatively, two of the R groups on NRR, NRNHR, or NRNRR may join together to form a 3- to 10-membered cyclic group in which the heteroatoms are N, O or S;

wherein, n=2-8;

each R is independently C$_1$-C$_8$ alkyl, C$_2$-C$_8$ alkenyl, C$_2$-C$_8$ alkalkenyl, C$_2$-C$_8$ alkenylalkyl, C$_2$-C$_8$ alkynyl, C$_2$-C$_8$ alkalkynyl, C$_2$-C$_8$ alkynylalkyl, C$_3$-C$_8$ cycloalkyl, C$_3$-C$_8$ cycloalkenyl, amino acid residue, substituted amino acid residue, C$_1$-C$_8$ hydroxyalkyl, C$_2$-C$_8$ sulfanylalkyl, C$_1$-C$_8$ cyanoalkyl, C$_1$-C$_8$ aminoalkyl, C$_1$-C$_8$ carboxyalkyl, methoxy, methylsulfanyl, C$_2$-C$_8$ alkoxy, C$_2$-C$_8$ alkylsulfanyl, C$_6$-C$_{12}$ aralkyl, or C$_3$-C$_6$ heterocycloalkyl; or, each R is independently H, CF$_3$, OCF$_3$, O—C$_6$-C$_{12}$ aryl or a O—C$_3$-C$_6$ heterocyclic group;

wherein Ar is conjugated C$_5$-C$_{10}$ monocyclic or bicyclic aryl; and Het is conjugated C$_5$-C$_{10}$ monocyclic or bicyclic aryl containing 1-3 heteroatoms selected from N, O and S;

$R_2$ is selected from H, OH, NH$_2$, methyl, ethyl, C$_3$-C$_{10}$ alkyl, methoxy, methylsulfanyl, C$_2$-C$_{10}$ alkoxy, C$_2$-C$_{10}$ alkylsulfanyl, CH$_2$NH$_2$, CH$_2$OH, CH$_2$OR, a conjugated C$_5$-C$_{10}$ aromatic cyclic group with or without a R substituent as defined above on the ring thereof, and a C$_3$-C$_6$ heterocycloalkyl group with or without a R substituent as defined above on the ring thereof;

$R_3$ is selected from H, CH$_3$, CH$_2$CH$_3$, CH$_2$CH$_2$CH$_3$, CHMe$_2$, CH$_2$SH, CH$_2$CH$_2$SH, CH$_2$OH, CH$_2$C$_6$H$_5$, CH$_2$CONH$_2$, CH$_2$COOH, CH$_2$COOR, CH$_2$CH$_2$CONH$_2$, CH$_2$CH$_2$COOH, CH$_2$CH$_2$COOR, CH$_2$CH$_2$CH$_2$NHC(=NH)NH$_2$, CHMeCH$_2$CH$_3$, CH$_2$CHMe$_2$, CH$_2$CH$_2$CH$_2$CH$_2$NH$_2$, CH$_2$CH$_2$SCH$_3$, CH(OH)CH$_3$, CH$_2$C$_6$H$_4$OH-p, CH$_2$-imidazolyl, CH$_2$-indolyl, C$_6$-C$_{10}$ alkyl, C$_2$-C$_{10}$ hydroxyalkyl, C$_4$-C$_{10}$ sulfanylalkyl, Ar, CH$_2$Ar and CH$_2$-Het, wherein there may or may not be a R substituent as defined above on the ring of said Ar and Het groups; and the Ar, Het and R groups have the same meanings as defined above;

$R_4$ is H, methyl, ethyl, C$_3$-C$_{10}$ alkyl, C$_6$-C$_{12}$ aralkyl or C$_3$-C$_6$ heterocycloalkyl;

$R_5$ is C$_1$-C$_{10}$ alkyl, C$_2$-C$_{10}$ alkenyl, C$_2$-C$_{10}$ alkalkenyl, C$_2$-C$_{10}$ alkenylalkyl, C$_2$-C$_{10}$ alkynyl, C$_2$-C$_{10}$ alkalkynyl, C$_2$-C$_{10}$ alkynylalkyl, C$_1$-C$_{10}$ cyanoalkyl, C$_1$-C$_{10}$ aminoalkyl, C$_1$-C$_{10}$ carboxyalkyl, (CH$_2$)$_n$OH, (CH$_2$)$_n$OR, (CH$_2$)$_n$SR, CH$_2$Ar, CH$_2$CH$_2$Ar, CH$_2$-Het or CH$_2$CH$_2$-Het, wherein there may or may not be a R substituent as defined above on the ring of said Ar and Het groups, and the Ar, Het and R groups have the same meanings as defined above and wherein n=2-8;

$R_6$ is NHR, NRR, NH(CH$_2$)$_n$OH, NH(CH$_2$)$_n$OR, NH(CH$_2$)$_n$SR, N[(CH$_2$)$_n$OH]$_2$, NHCH$_2$Ar, NHAr, N(CH$_2$Ar)$_2$, NAr$_2$, NHCH$_2$-Het, or cyclic amino groups having 3-8 carbon atoms with or without 1-2 carbon atoms in the ring thereof being substituted with O, S, NH, NR, PO or P(O)(OH)$_2$; wherein each R is independently C$_1$-C$_{15}$ alkyl, C$_2$-C$_{15}$ alkenyl, C$_2$-C$_{15}$ alkalkenyl, C$_2$-C$_{15}$ alkenylalkyl, C$_2$-C$_{15}$ alkynyl, C$_2$-C$_{15}$ alkalkynyl, C$_2$-C$_{15}$ alkynylalkyl, C$_3$-C$_{15}$ cycloalkyl, C$_3$-C$_{15}$ cycloalkenyl, C$_6$-C$_{12}$ aralkyl, C$_3$-C$_6$ heterocycloalkyl, hydroxyalkyl, sulfanylalkyl, cyanoalkyl, aminoalkyl or carboxyalkyl, or is defined as above; and wherein the Ar and Het groups have the same meanings as defined above;

$R_7$ is C$_1$-C$_{18}$ alkyl, hydroxymethyl, hydroxyethyl, hydroxypropyl, C$_4$-C$_{10}$ hydroxyalkyl, CH$_2$OR, CH$_2$SR, Ar, Het, (CH$_2$)$_{1-12}$—Ar, (CH$_2$)$_{1-12}$-Het, or a C$_1$-C$_{18}$ alkyl with 1-3 double bonds or triple bonds or 1-3 O or S atoms in the alkyl chain; wherein the Ar and Het groups are as defined above; and X is NH, O, S, or NR;

provided that when B is

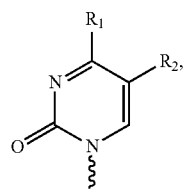

$R_1$ is not NH$_2$ or OH.

2. The compound of claim 1, or a pharmaceutically acceptable salt thereof, wherein $R_5$ is selected from the group consisting of:

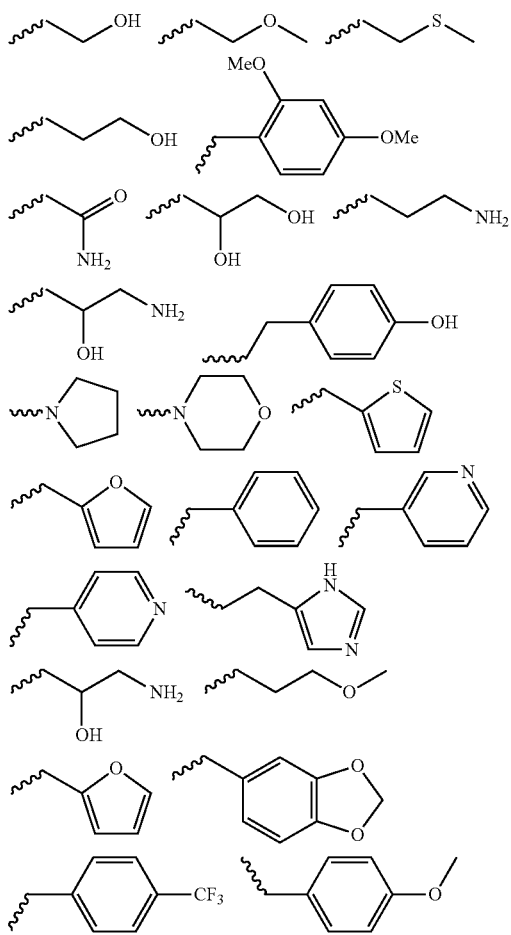

3. The compound of claim 1, or a pharmaceutically acceptable salt thereof, wherein when B is

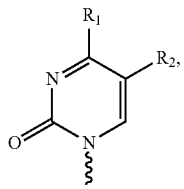

$R_2$ is H and $R_1$ is selected from the group consisting of:
EtNH, NHCH$_2$CH$_2$NH$_2$,

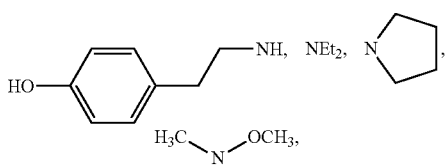

NHOCH$_3$, NHOEt,

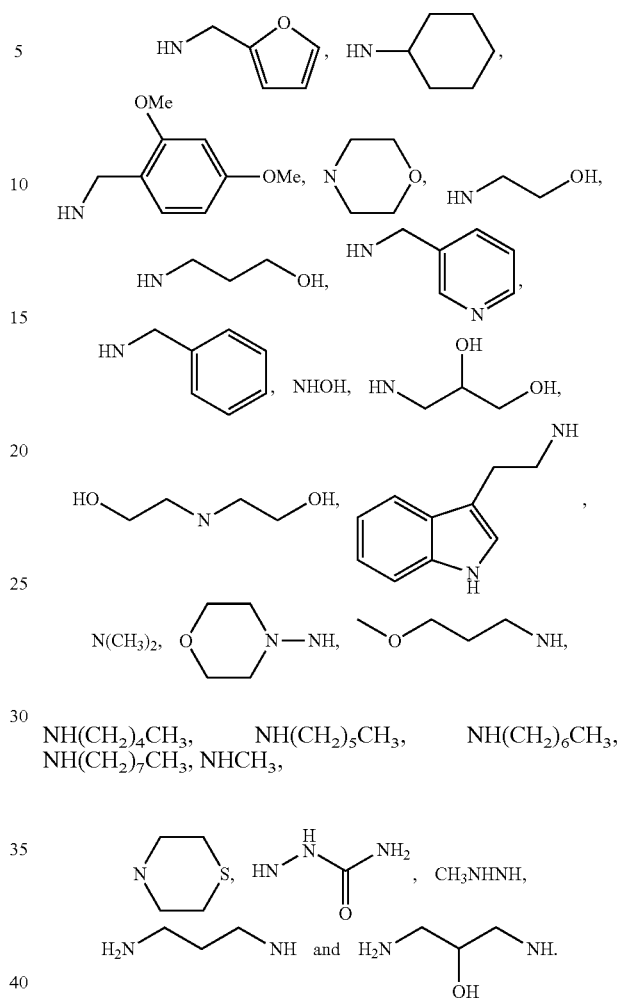

NH(CH$_2$)$_4$CH$_3$, NH(CH$_2$)$_5$CH$_3$, NH(CH$_2$)$_6$CH$_3$, NH(CH$_2$)$_7$CH$_3$, NHCH$_3$,

4. A method of synthesizing the compound of claim 1 wherein the basic group B is

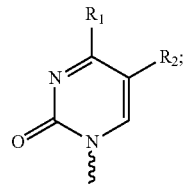

wherein $R_2$ is H and $R_1$ is as previously defined, comprising the following steps:
  adding successively dry N,N-dimethylformamide, DMAP, N-ethyldiisopropylamine and a selected amine as a building block to compound 4 in a reaction vessel;
  stirring the reaction mixture at room temperature under the protection of N$_2$;
  adding ethyl acetate to the mixture which is then washed with water and dried over anhydrous sodium sulfate;
  removing solvent under reduced pressure;
  stirring a mixture of the crude product and methanol solution saturated with ammonia gas in a sealed reaction vessel at room temperature;

removing solvent under reduced pressure and purifying the crude product;
wherein compound 4 is of the structure:

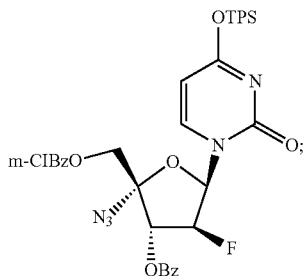

and
wherein TPS is

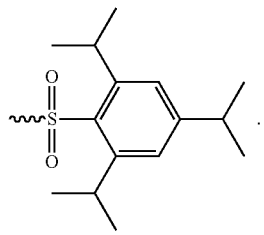

5. The compound of claim 1, wherein the compound is of the formula (1):

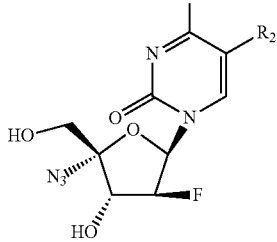
(1)

or a pharmaceutically acceptable salt thereof.

6. The compound of claim 1, wherein the compound is of the formula (2):

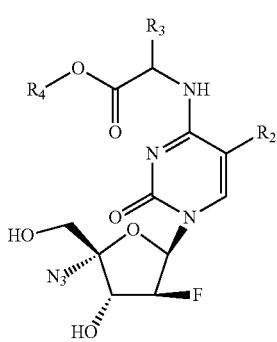
(2)

or a pharmaceutically acceptable salt thereof.

7. The compound of claim 1, wherein the compound is of the formula (3) or (4):

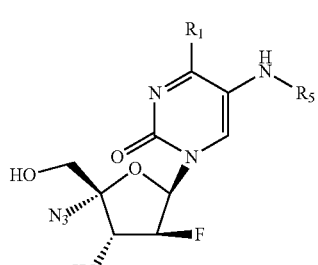
(3)

or

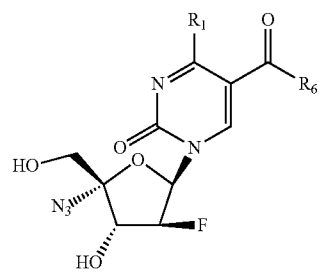
(4)

or a pharmaceutically acceptable salt thereof.

8. The compound of claim 1, wherein the compound is of the formula (5) or (6):

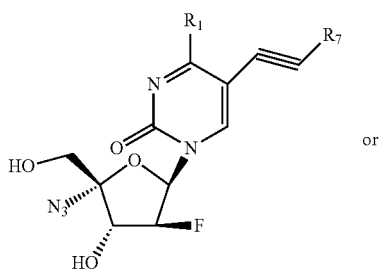
(5)

or

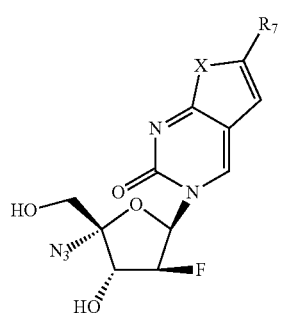
(6)

or a pharmaceutically acceptable salt thereof.

9. A compound having the following structure:

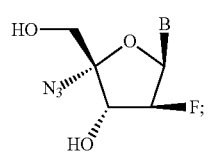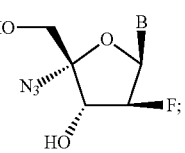

or a pharmaceutically acceptable salt thereof, wherein B is

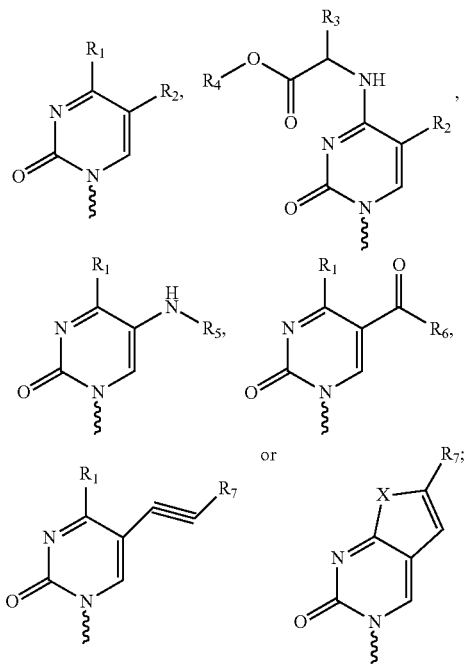

$R_1$, $R_2$ and $R_3$ are each independently selected from the group consisting of:

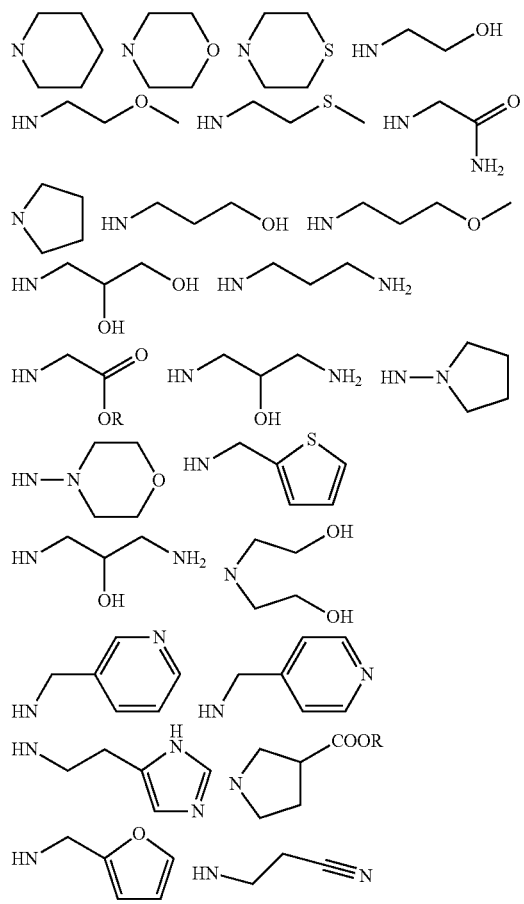

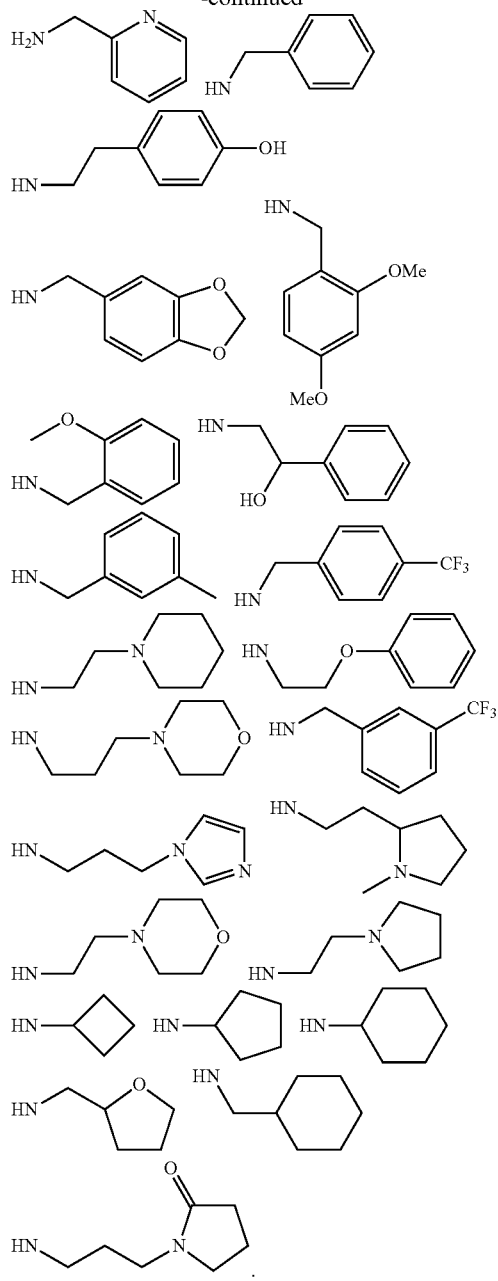

$R_4$ is H, methyl, ethyl, $C_3$-$C_{10}$ alkyl, $C_6$-$C_{12}$ aralkyl or $C_3$-$C_6$ heterocycloalkyl;

$R_5$ is $C_1$-$C_{10}$ alkyl, $C_2$-$C_{10}$ alkenyl, $C_2$-$C_{10}$ alkalkenyl, $C_2$-$C_{10}$ alkenylalkyl, $C_2$-$C_{10}$ alkynyl, $C_2$-$C_{10}$ alkalkynyl, $C_2$-$C_{10}$ alkynylalkyl, $C_1$-$C_{10}$ cyanoalkyl, $C_1$-$C_{10}$ aminoalkyl, $C_1$-$C_{10}$ carboxyalkyl, $(CH_2)_n OH$, $(CH_2)_n OR$, $(CH_2)_n SR$, $CH_2Ar$, $CH_2CH_2Ar$, $CH_2$-Het or $CH_2CH_2$-Het;

wherein n=2-8; each R is independently $C_1$-$C_8$ alkyl, $C_2$-$C_8$ alkenyl, $C_2$-$C_8$ alkalkenyl, $C_2$-$C_8$ alkenylalkyl, $C_2$-$C_8$ alkynyl, $C_2$-$C_8$ alkalkynyl, $C_2$-$C_8$ alkynylalkyl, $C_3$-$C_8$ cycloalkyl, $C_3$-$C_8$ cycloalkenyl, $C_1$-$C_8$ hydroxyalkyl, $C_2$-$C_8$ sulfanylalkyl, $C_1$-$C_8$ cyanoalkyl, $C_1$-$C_8$ aminoalkyl, $C_1$-$C_8$ carboxyalkyl, methoxy, methylsulfanyl, $C_2$-$C_8$ alkoxy, $C_2$-$C_8$ alkylsulfanyl, $C_6$-$C_{12}$ aralkyl, or $C_3$-$C_6$ heterocycloalkyl; or each R is independently H, $CF_3$, $OCF_3$, O—$C_6$-$C_{12}$ aryl or a O—$C_3$-$C_6$ heterocyclic group; each Ar is independently a conjugated $C_5$-$C_{10}$ monocyclic or bicyclic aryl; and each Het is independently a conjugated $C_5$-$C_{10}$ monocyclic or bicyclic aryl containing 1-3 heteroatoms selected from N, O and S;

$R_6$ is NHR, NRR, NH($CH_2$)$_n$OH, NH($CH_2$)$_n$OR, NH($CH_2$)$_n$SR, N[($CH_2$)$_n$OH]$_2$, NHCH$_2$Ar, NHAr, N(CH$_2$Ar)$_2$, NAr$_2$, NHCH$_2$-Het, or cyclic amino groups having 3-8 carbon atoms with or without 1-2 carbon atoms in the ring thereof being substituted with O, S, NH, NR, PO or P(O)(OH)$_2$; wherein each R is independently $C_1$-$C_{15}$ alkyl, $C_2$-$C_{15}$ alkenyl, $C_2$-$C_{15}$ alkalkenyl, $C_2$-$C_{15}$ alkenylalkyl, $C_2$-$C_{15}$ alkynyl, $C_2$-$C_{15}$ alkalkynyl, $C_2$-$C_{15}$ alkynylalkyl, $C_3$-$C_{15}$ cycloalkyl, $C_3$-$C_{15}$ cycloalkenyl, $C_6$-$C_{12}$ aralkyl, $C_3$-$C_6$ heterocycloalkyl, hydroxyalkyl, sulfanylalkyl, cyanoalkyl, aminoalkyl or carboxyalkyl, or is defined as above; and wherein the Ar and Het groups have the same meanings as defined above;

$R_7$ is $C_1$-$C_{18}$ alkyl, hydroxymethyl, hydroxyethyl, hydroxypropyl, $C_4$-$C_{10}$ hydroxyalkyl, CH$_2$OR, CH$_2$SR, Ar, Het, (CH$_2$)$_{1-12}$—Ar, (CH$_2$)$_{1-12}$-Het, or a $C_1$-$C_{18}$ alkyl with 1-3 double bonds or triple bonds or 1-3 O or S atoms in the alkyl chain; wherein the Ar and Het groups are as defined above; and X is NH, O, S, or NR.

10. A compound selected from the group consisting of:

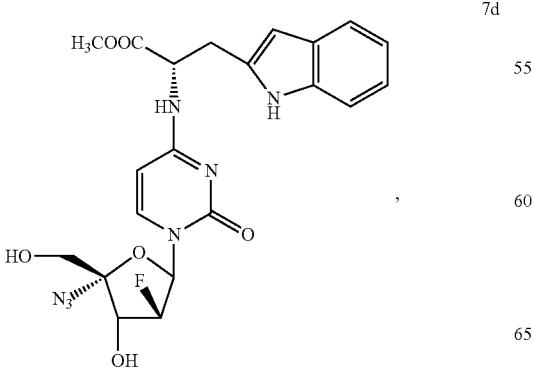

8a

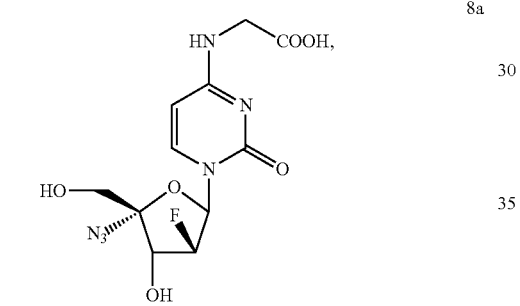

7b

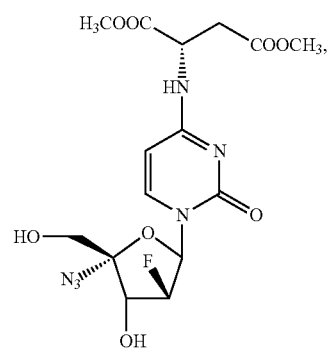

7d

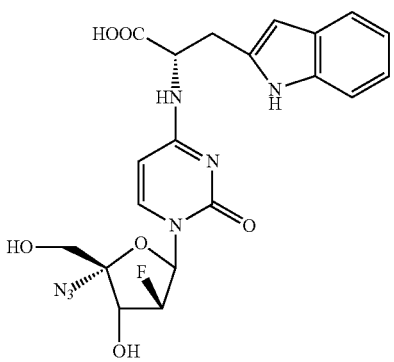

8d

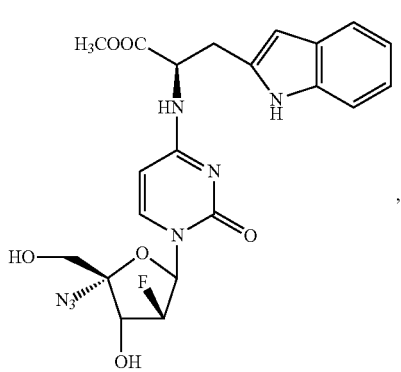

7c

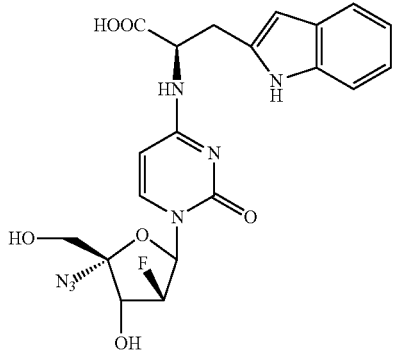

8c

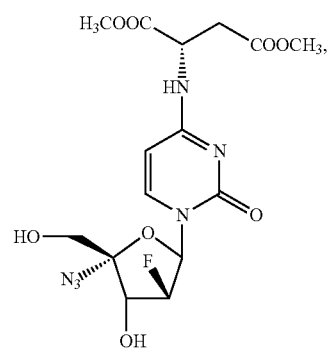

7e

-continued
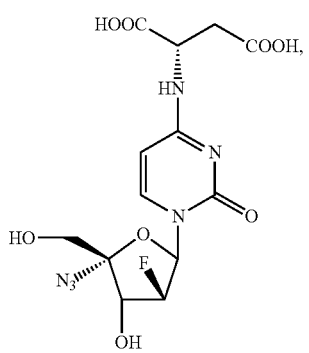  8e
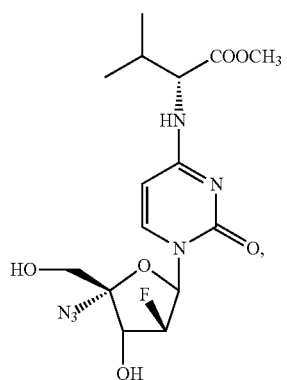  7f
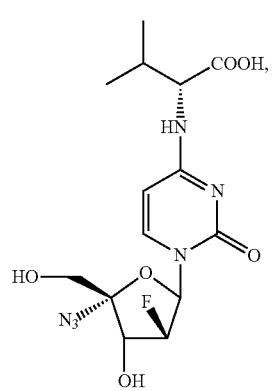  8f
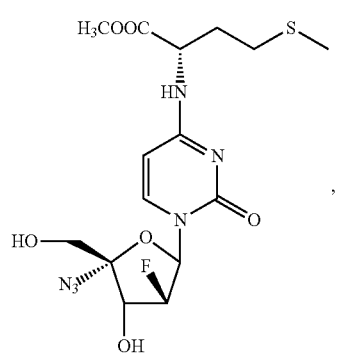  7g
-continued
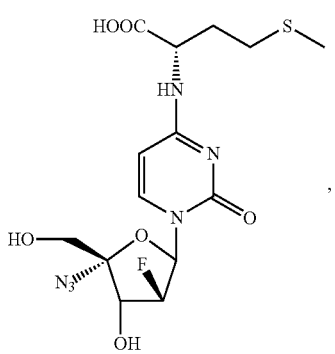  8g
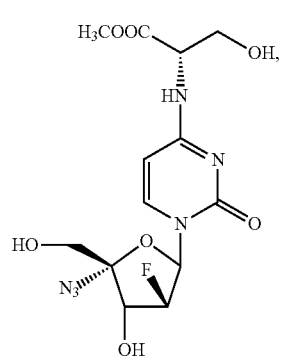  7h
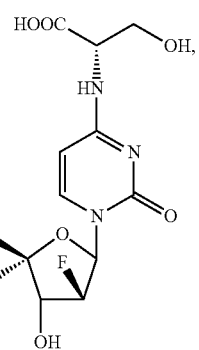  8h
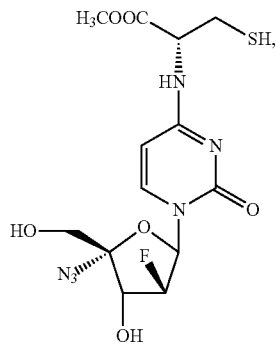  7i 97
-continued
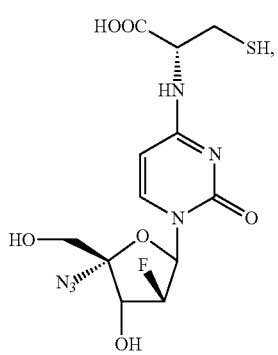
8i
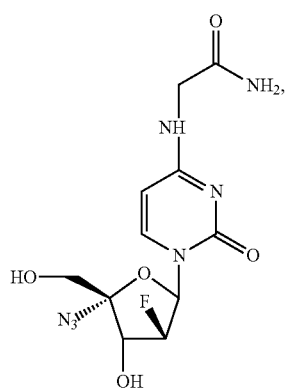
7j
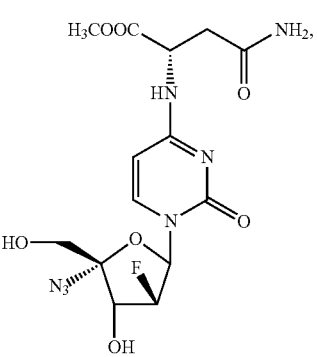
7k
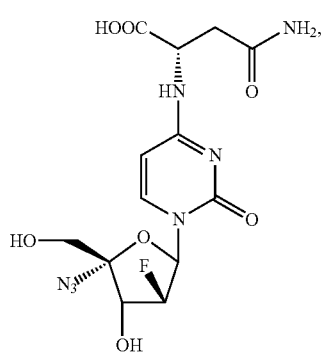
8k
98
-continued
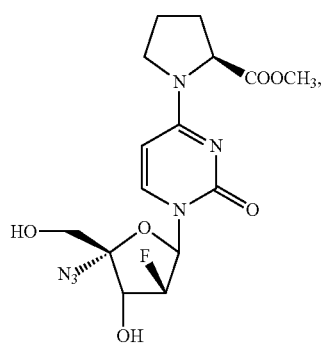
7L
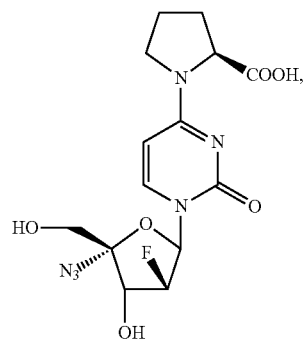
8L
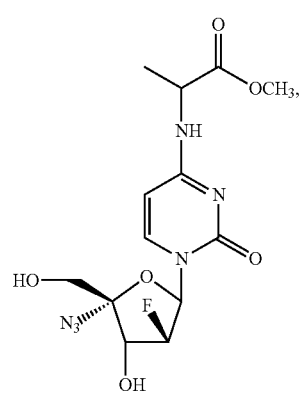
7m
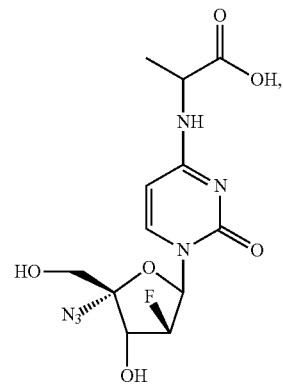
8m

19

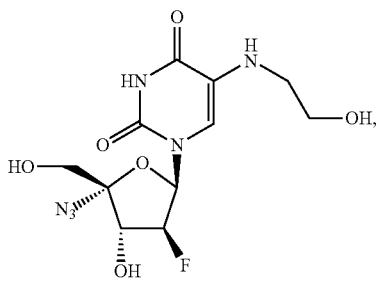

20

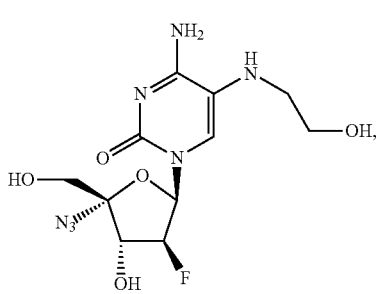

22

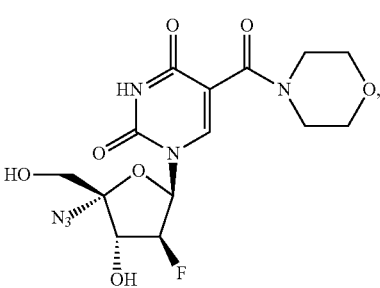

23

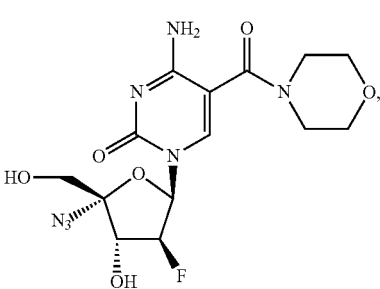

25

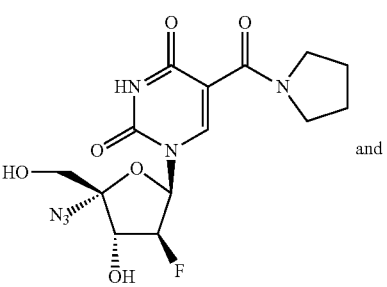

and

26

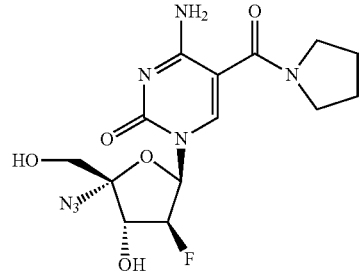

or a pharmaceutically acceptable salt thereof.

11. A method of synthesizing the compound of claim 1 wherein the basic group B is

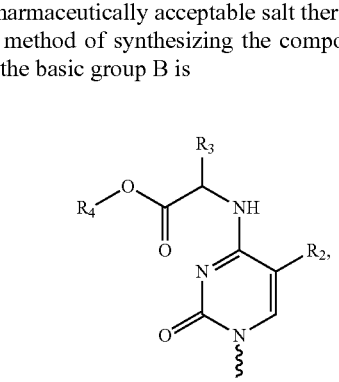

wherein $R_2$ is H, and $R_3$ and $R_4$ are as previously defined, comprising the following steps:

adding amino acid methyl ester hydrochloride, diisopropylethylamine and catalytic amount of DMAP to compound 4 dissolved in dry DMF and stirring the mixture to react at room temperature; monitoring the reaction process by TLC; adding water to the reaction upon its completion; performing extraction, organic phase drying and filtration; removing solvent;

wherein compound 4 is of the structure:

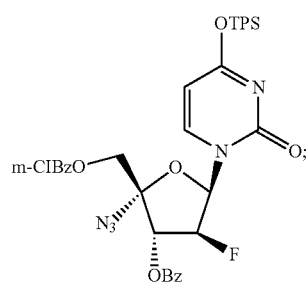

and wherein TPS is

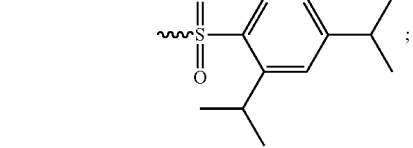

purifying the crude product to give intermediate A:

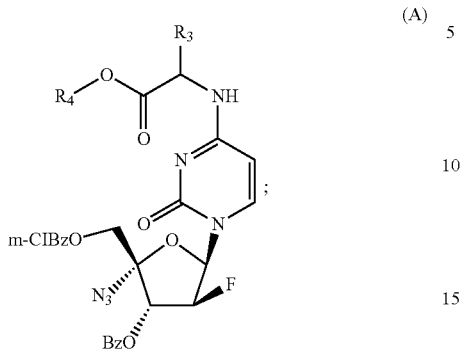

(A)

dissolving intermediate A in THF and $C_{1-5}$ alkyl alcohol to form a solution;

adding lithium hydroxide thereto;

stirring the mixture to react then directly evaporating the mixture to dryness; purifying the crude product on TLC plate to give intermediate B:

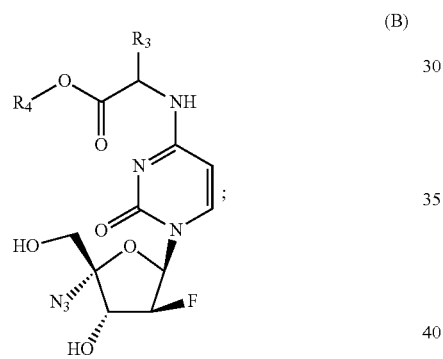

(B)

and hydrolyzing intermediate B with potassium hydroxide to give the compound of claim 1 with N-amino acid substitution at position 4.

12. A method of synthesizing the compound of claim 1 wherein the basic group B is

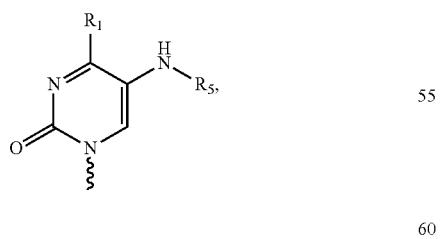

wherein $R_1$=$NH_2$, and $R_5$ is as previously defined, comprising the following steps:

heating an ethanol solution of compound 9 or compound 9' and 2-aminoethanol to react;

wherein compound 9 is of the structure:

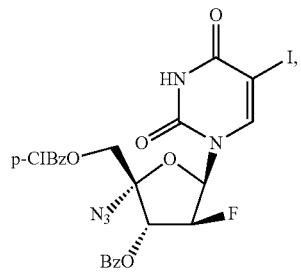

and compound 9' is of the structure:

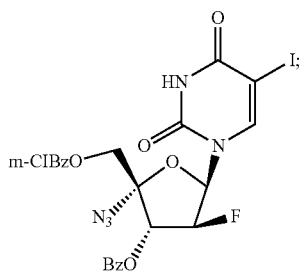

removing solvent under reduced pressure;

adding pyridine and acetic anhydride to form a mixture that is stirred to react at room temperature and subjected to extraction, washing, drying and filtration to afford the intermediate:

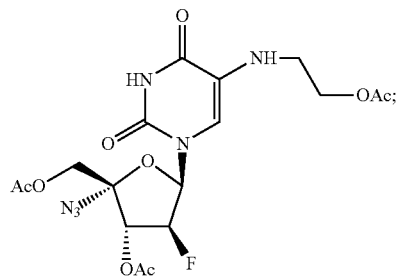 [SMILES: CC(=O)OCCNc1cn([C@@H]2O[C@@](COC(C)=O)(N=[N+]=[N-])[C@@H](OC(C)=O)[C@@H]2F)c(=O)[nH]c1=O]

adding anhydrous dichloromethane to the intermediate to form a solution that is added with triazole and pyridine successively with stirring;

cooling the solution in an ice bath and adding $POCl_3$ thereto;

stirring the solution and further adding additional triazole and $POCl_3$ thereto;

quenching the reaction with water after overnight stirring;

performing extraction, organic phase drying and solvent evaporation;

adding THF and aqueous ammonia to the residue to react with stirring;

evaporating the solution to dryness and adding ammonia methanol solution;

stirring overnight; and performing extraction to obtain the product.

13. A method of synthesizing the compound of claim 1 wherein the basic group B is

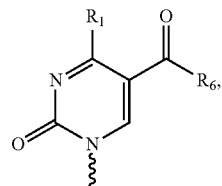

wherein $R_1$ is $NH_2$, and $R_6$ is as previously defined, comprising the following steps:

adding an amine building block-containing compound and carbon dioxide into a solution of compound 9' dissolved in THF;

wherein compound 9' is of the structure:

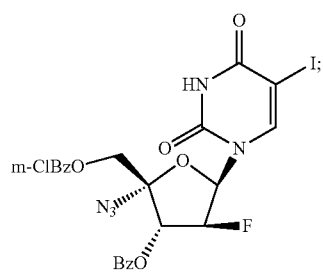

adding $Pd(PPh_3)_4$ under $N_2$ protection to the solution to react;

monitoring the reaction process by TLC;

performing filtration upon completion of the reaction;

concentrating the filtrate;

purifying the concentrate on silica column to afford a 5-substituted pyrimidine nucleoside intermediate III as an intermediate:

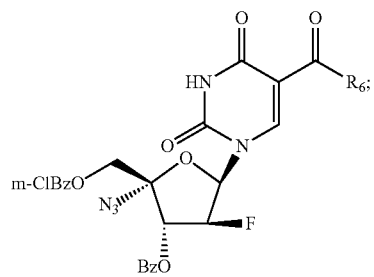

adding anhydrous dichloromethane to the intermediate to form a solution that is added with triazole and pyridine successively with stirring;

cooling the solution in an ice bath and adding dropwise $POCl_3$ thereto slowly;

stirring the solution and further adding additional triazole and $POCl_3$ thereto;

quenching the reaction with water after overnight stirring;

performing extraction and drying;

adding $NH_3/CH_3OH$ to the residue to react under sealed conditions with stirring; and performing purification process on silica column after complete consumption of the starting material as determined by TLC, to afford the compound of claim 1 with amidation at position 5.

14. A method of synthesizing the compound of claim 1, comprising the following steps:

adding $Et_3N$, 3-butyn-1-ol, $Pd_2(dba)_4$, CuI and $PPh_3$ successively into a solution of compound 9 or compound 9' dissolved in dry DMF to react under $N_2$ protection:

wherein compound 9 is of the structure:

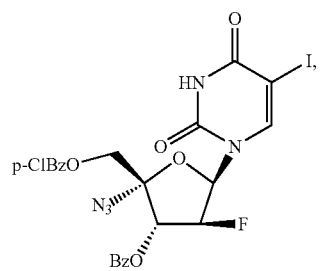

and compound 9' is of the structure:

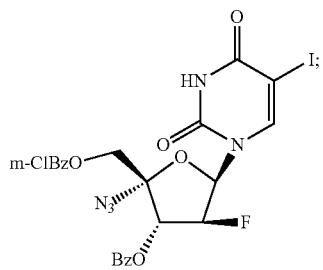

evaporating the solution to dryness and loading the residue on a column with dry method; and running the column with ethyl acetate/petroleum ether to afford a 5-substituted pyrimidine nucleoside intermediate of the structure:

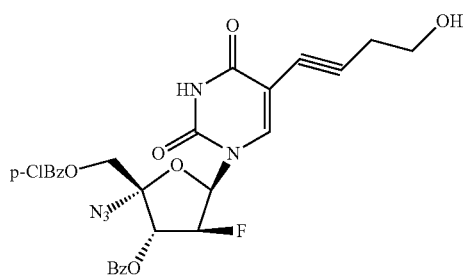

or of the structure:

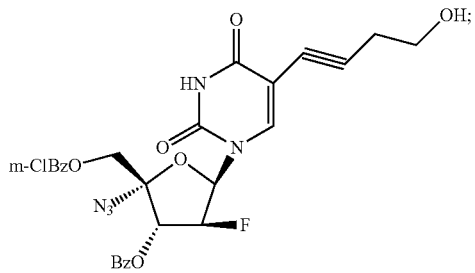

adding saturated ammonia/methanol to the intermediate and stirring the solution formed at room temperature;
loading sample on a column with dry method;
running the column with dichloromethane/methanol to afford an intermediate of the structure:

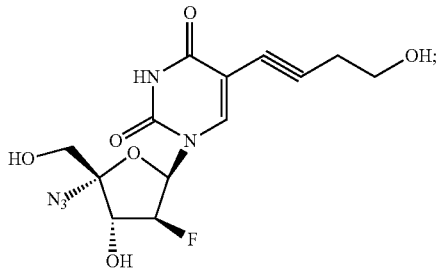 [SMILES: [N-]=[N+]=N[C@]1(CO)O[C@@H](n2cc(C#CCCO)c(=O)[nH]c2=O)[C@@H](F)[C@@H]1O]

performing a cyclization reaction on the intermediate to afford the compound of claim 1 wherein B is

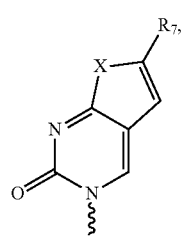

wherein X=O and $R_7$=2-hydroxyethyl.

15. A method for treating a cancer or a viral disease comprising administering to a subject in need thereof a compound of claim 1, or a pharmaceutically acceptable salt thereof, wherein the cancer is a lymphoma; and the viral disease is selected from hepatitis B, hepatitis C and HIV-1.

16. The method according to claim 15, wherein the compound, or a pharmaceutically acceptable salt thereof, is administrated orally, parenterally, or through an implantable drug pump.

17. The method according to claim 16, wherein the method is for treating a lymphoma.

18. The method according to claim 16, wherein the method is for treating a viral disease selected from the group consisting of hepatitis B, hepatitis C and HIV-1.

19. The method according to claim 15, wherein the method is for treating a lymphoma.

20. The method according to claim 15, wherein the method is for treating a viral disease selected from the group consisting of hepatitis B, hepatitis C and HIV-1.

* * * * *